(12) United States Patent
Terreux et al.

(10) Patent No.: US 8,158,586 B2
(45) Date of Patent: Apr. 17, 2012

(54) INHIBITORS OF PROTEIN KINASES AND USES THEREOF

(75) Inventors: Raphael Terreux, Lyons (FR); Jenny Phipps, Chelsea (CA)

(73) Assignee: Pharmagap Inc., Ottawa (CA)

( * ) Notice: Subject to any disclaimer, the term of this patent is extended or adjusted under 35 U.S.C. 154(b) by 585 days.

(21) Appl. No.: 11/911,319

(22) PCT Filed: Apr. 11, 2006

(86) PCT No.: PCT/CA2006/000521
§ 371 (c)(1),
(2), (4) Date: Sep. 2, 2008

(87) PCT Pub. No.: WO2006/108270
PCT Pub. Date: Oct. 19, 2006

(65) Prior Publication Data
US 2009/0042803 A1    Feb. 12, 2009

Related U.S. Application Data

(60) Provisional application No. 60/669,898, filed on Apr. 11, 2005.

(51) Int. Cl.
*A61K 38/08* (2006.01)
*A61K 38/10* (2006.01)
*A61K 38/55* (2006.01)
*C07K 7/06* (2006.01)
*C07K 7/08* (2006.01)

(52) U.S. Cl. ............... 514/19.3; 514/21.5; 514/21.6; 514/21.7; 514/21.8; 530/327; 530/328; 530/329; 530/345

(58) Field of Classification Search .................. None
See application file for complete search history.

(56) References Cited

U.S. PATENT DOCUMENTS

| | | |
|---|---|---|
| 4,582,821 A | 4/1986 | Kettner et al. |
| 4,923,802 A | 5/1990 | Gallis et al. |
| 5,141,957 A | 8/1992 | Jiang et al. |
| 5,204,370 A | 4/1993 | Jiang et al. |
| 5,216,014 A | 6/1993 | Jiang et al. |
| 5,270,310 A | 12/1993 | Bell et al. |
| 5,292,737 A | 3/1994 | Defauw et al. |
| 5,344,841 A | 9/1994 | Jiang et al. |
| 5,360,818 A | 11/1994 | Jiang et al. |
| 5,432,198 A | 7/1995 | Jagdmann et al. |
| 5,481,003 A | 1/1996 | Gillig et al. |
| 5,491,242 A | 2/1996 | Gillig et al. |
| 5,501,959 A | 3/1996 | Lancaster et al. |
| 5,545,636 A | 8/1996 | Heath et al. |
| 5,552,396 A | 9/1996 | Heath et al. |
| 5,559,209 A * | 9/1996 | Nishimoto ............ 530/326 |
| 5,616,577 A | 4/1997 | Nambi et al. |
| 5,624,949 A | 4/1997 | Heath et al. |
| 5,661,173 A | 8/1997 | Heath et al. |
| 5,668,152 A | 9/1997 | Heath et al. |
| 5,672,618 A | 9/1997 | Heath et al. |
| 5,696,108 A | 12/1997 | Heath et al. |
| 5,698,578 A | 12/1997 | Heath et al. |
| 5,710,145 A | 1/1998 | Engel et al. |
| 5,719,175 A | 2/1998 | Heath et al. |
| 5,750,555 A | 5/1998 | Trostmann et al. |
| 5,783,405 A | 7/1998 | Mochly-Rosen et al. |
| 5,821,072 A | 10/1998 | Schwartz et al. |
| 5,936,084 A | 8/1999 | Jirousek et al. |
| 6,015,807 A | 1/2000 | Engel et al. |
| 6,090,929 A | 7/2000 | Scott et al. |
| 6,117,861 A | 9/2000 | Engel et al. |
| 6,165,977 A | 12/2000 | Mochly-Rosen et al. |
| 6,174,993 B1 | 1/2001 | Ben-Sasson et al. |
| 6,218,113 B1 | 4/2001 | Yue et al. |
| 6,232,299 B1 | 5/2001 | Jirousek et al. |
| 6,376,467 B1 | 4/2002 | Messing et al. |
| 6,387,641 B1 | 5/2002 | Bellon et al. |
| 6,444,638 B2 | 9/2002 | Schwartz et al. |
| 6,518,397 B1 * | 2/2003 | Dedhar ................ 530/300 |
| 2002/0031820 A1 | 3/2002 | Cole et al. |
| 2002/0049301 A1 | 4/2002 | Ben-Sasson et al. |
| 2002/0115173 A1 | 8/2002 | Ben-Sasson et al. |
| 2002/0137141 A1 | 9/2002 | Ben-Sasson et al. |
| 2002/0160478 A1 | 10/2002 | Ben-Sasson et al. |
| 2003/0143656 A1 | 7/2003 | Dundee et al. |
| 2003/0223981 A1 | 12/2003 | Mochly-Rosen et al. |
| 2004/0014082 A1 | 1/2004 | Tadayoni-Rebek et al. |
| 2004/0014207 A1 | 1/2004 | Pease et al. |
| 2005/0026840 A1 | 2/2005 | Livnah et al. |
| 2006/0003431 A1 | 1/2006 | Xu et al. |
| 2007/0173437 A1 * | 7/2007 | Parang et al. ............ 514/7 |
| 2010/0041597 A1 | 2/2010 | Phipps et al. |
| 2011/0039770 A1 | 2/2011 | Phipps et al. |

FOREIGN PATENT DOCUMENTS

| | | |
|---|---|---|
| EP | 0045665 A1 | 2/1982 |
| EP | 0666270 A2 | 8/1995 |
| WO | WO 93/20101 | 10/1993 |
| WO | WO 98/07835 | 2/1998 |
| WO | WO 99/57305 | 11/1999 |
| WO | WO 00/18895 | 4/2000 |
| WO | WO 00/42213 | 7/2000 |
| WO | WO 00/70030 | 11/2000 |
| WO | WO 01/42243 | 6/2001 |
| WO | WO 01/42280 | 6/2001 |
| WO | WO 01/44497 | 6/2001 |
| WO | WO 01/70770 | 9/2001 |
| WO | WO 03/004050 | 1/2003 |
| WO | WO 03/010185 | 2/2003 |
| WO | WO 03/012122 | 2/2003 |
| WO | WO 03/059943 | 7/2003 |
| WO | WO 2004/062475 | 7/2004 |
| WO | WO 2006/108270 | 10/2006 |
| WO | WO 2007/016763 | 2/2007 |
| WO | WO 2007/016777 | 2/2007 |

OTHER PUBLICATIONS

International Search Report and Written Opinion dated Aug. 10, 2006 issued in PCT/CA2006/000521(WO/2006/108270).

International Search Report and Written Opinion dated Dec. 18, 2006 issued in PCT/CA2006/001298 (WO/2007/016777).

International Search Report dated Nov. 17, 2006 issued in PCT/CA2006/001259 (WO/2007/016763).

European Extended Search Report dated Sep. 1, 2010 issued in EP06721775.2.

European Extended Search Report dated Jul. 1, 2011 issued in EP06775080.2.

European Extended Search Report dated Feb. 4, 2010 issued in EP06804620.0.

Almquist et al. (1980) "Synthesis and Biological Activity of a Ketomethylene Analogue of a Tripeptide Inhibitor of Angiotensin Converting Enzyme" *J. Med. Chem.* 23:1392-1398.

Arnould et al. (1998) "The Polycystic Kidney Disease 1 Gene Product Mediates Protein Kinase C α-dependent and c-Jun N-terminal Kinase-dependent Activation of the Transcription Factor AP-1" *J. Biol. Chem.* 13:6013-6018.

Barany-Wallje et al. (2005) "A Critical Reassessment of Penetratin Translocation Across Lipid Membranes" *Biophys. J.* 89:2513-2521 (E-pub Jul. 22, 2005).

Barton et al. (2004) "Association of protein kinase C alpha (PRKCA) gene with multiple sclerosis in a UK population" *Brain* 127:1717-1722.

Brooks et al. (1989) "Tumour-promoting and hyperplastic effects of phorbol and daphnane esters in CD-1 mouse skin and a synergistic effect of calcium ionophore with the non-promoting activator of protein kinase C, sapintoxin A" *Carcinogenesis* 10(2):283-288.

Carter (2000) "Protein Kinase C as a Drug Target: Implications for Drug or Diet Prevention and Treatment of Cancer" *Current Drug Targets* 1(2): 163-183.

Chapline et al. (1993) "Interaction Cloning of Protein Kinase C Substrates" *The Journal of Biological Chemistry* 268(10):6858-6861.

Chapline et al. (1996) "Identification of a Major Protein Kinase C-binding Protein and Substrate in Rat Embryo Fibroblasts" *The Journal of Biological Chemistry* 271(11):6417-6422.

Clark et al. (2003) "Altered Protein Kinase C (PKC) Isoforms in Non-Small Cell Lung Cancer Cells: PKCδ Promotes Cellular Survival and Chemotherapeutic Resistance" *Cancer Research* 63:780-786.

Dada et al. (2003) "Hypoxia-induced endocytosis of Na,K-ATPase in alveolar epithelial cells is mediated by mitochondrial reactive oxygen species and PKC-ζ" *The Journal of Clinical Investigation* 111: 1057-1064.

Dancey et al. (2003) "Issues and Progress with Protein Kinase Inhibitors for Cancer Treatment" *Nat Rev Drug Discovery* 2:296-313.

Detjen et al. (2000) "Activation of protein kinase Cα inhibits growth of pancreatic cancer cells via p21cip-mediated $G_1$ arrest" *J. Cell Sci.* 113:3025-3035.

Diaz-Meco et al. (1996) "Lambda-Interacting Protein, a Novel Protein That Specifically Interacts with the Zinc Finger Domain of the Atypical Protein Kinase C Isotype A./L and Stimulates Its Kinase Activity In Vitro and In Vivo" *Mol. Cell. Biol.* 16(1):105-114.

Dutil et al. (2000) "Dual Role of Pseudosubstrate in the Coordinated Regulation of Protein Kinase C by Phosphorylation and Diacylglycerol" *J. Biol. Chem.* 275 (14): 10697-10701.

Fields et al. (1993) "Dual-attribute continuous monitoring of cell proliferation/cytotoxicity" *Am. Biotechnol. Lab.* 11:48-50.

Fuchs et al. (2003) "Pathway for Polyarginine Entry into Mammalian Cells" *Biochemistry* 43:2438-44.

Goekjian et al. (1999) "Protein kinase C in the treatment of disease: signal transduction pathways, inhibitors, and agents in development." *Curr. Med. Chem.* 6: 877-903.

Goekjian et al. (2001) "Protein kinase C inhibitors as novel anticancer drugs" *Expert Opin. Invest. Drugs* 10: 2117-2140.

Hanauske et al. (2004) "The Role of Protein Kinase C-alpha (PKC-α) in Cancer and its Modulation by the Novel PKC-α-Specific Inhibitor Aprinocarsen" *Curr. Pharm. Design* 10:1923-1936.

Hann et al. (1982) "On the Double Bond Isostere of the Peptide Bond: Preparation of an Enkephalin Analogue" *Chem. Soc. Perkin Trans. I* 307-314.

Hofman (2004) "Protein Kinase C Isozymes as Potential Targets for Anticancer Therapy" *Curr. Cancer Drug Targets* 4(2):125-146.

Holladay et al. (1983) "Synthesis of Hydroxyethylene and Ketomethylene Dipeptide Isosteres" *Tetrahedron Lett.* 24(41):4401-4404.

Hruby (1982) "Conformational Restrictions of Biologically Active Peptides via Amino Acid Side Chain Groups" *Life Sci.* 31:189-199.

Hudson et al. (1979) "Methionine Enkephalin and Isosteric Analogues" *Int. J. Pept. Prot. Res.* 14:177-185.

Isaji et al. (1997) "Tranilast inhibits the proliferation, chemotaxis and tube formation of human microvascular endothelial cells in vitro and angiogenesis in vivo" *Brit. J. Pharmacol.* 122:1061-1066.

Jennings-White et al. (1982) "Synthesis of Ketomethylene Analogs of Dipeptides" *Tetrahedron Lett.* 23(25):2533-34.

Johnson et al. (1996) "A Protein Kinase C Translocation Inhibitor as an Isozyme-selective Antagonist of Cardiac Function" *The Journal of Biological Chemistry* 271(40):24962-24966.

Kitano et al. (1991) "Suppression of proliferation of human epidermal keratinocytes by 1, 25-dihydroxyvitamin $D_3$" *Euro. J. Clin. Investig.* 21:53-58.

Koivunen et al. (2004) "Protein Kinase C α/β Inhibitor Go6976 Promotes Formation of Cell Junctions and Inhibits Invasion of Urinary Bladder Carcinoma Cells" *Cancer Research* 64:5693-5701.

Kubo et al. (1992) "Effects of Long-Term Administration of (4S)-1-Methy1-3-{(2S)-2[N-((1S)-1-ethoxycarbonyl-3-phenylpropyl)amino]propionyl}-2-oxoimidazolidine-4-carboxylic Acid Hydrochloride (TA-6366), a New Angiotensin I Converting Enzyme (ACE) Inhibitor, from the Pre-hypertensive Stage on Morphological Change and Mechanical Property Related to Sodium Ion Permeability in Aorta of Spontaneously Hypertensive Rats (SHRs)" J.Pharmacobio-Dyn. 15:657-65.

Lahn et al. (2006) "The Role of Protein Kinase C-Alpha in Hematologic Malignancies" *Acta-Haematol.* 115:1-8.

Mashhoon et al. (2001) "Structure of the Unliganded cAMP-Dependent Protein Kinase Catalytic Subunit from *Saccharomyces cerevisiae*" *Arch. Biochem. Biophys.* 387: 11-19.

Medzihradszky et al. (1994) "Solid-Phase Synthesis of Adenosine Phosphopeptides as Potential Bisubstrate Inhibitors of Protein Kinases" *J. Am. Chem.Soc.* 116:9413-9419.

Mochly-Rosen et al. (1991) "Identification of intracellular receptor proteins for activated protein kinase C" *Proc. Acad. Natl. Sci. USA* 88:3997-4000.

Morley (1980) "Modulation of the action of regulatory peptides by structural modification" *Trends Pharm. Sci.* pp. 463-468.

Nakabayashi et al. (1990) "Phosphorylation of magainin-2 by protein kinase C and inhibition of protein kinase C isozymes by a synthetic analogue of magainin-2-amide" *FEBS Lett.* 267(1): 135-138.

Newton (1996) "Protein kinase C: Ports of anchor in the cell" *Current Biology* 6(7):806-809.
Niesman et al. (1997) "Therapeutic Effect of Liposomal Superoxide Dismutase in an Animal Model of Retinopathy of Prematurity" *Neurochem Res*. 22(5):597-605.
O'Brien et al. (2000) "Investigation of the Alamar Blue (resazurin) fluorescent dye for the assessment of mammalian cell cytotoxicity" *Eur. J. Biochem*. 267:5421-5426.
Parang et al. (2001) "Mechanism-based design of a protein kinase inhibitor" *Nature Struc. Biol*. 8:37-41.
PharmaGap (Feb. 2006) Non-confidential licensing dossier "PhGα (an Inhibitor of PKCalpha): Pre-clinical Drug Candidate for Use in Treating Drug-Resistant Cancer" pp.
PharmaGap (Retrieved on Apr. 28, 2006) "Cancer Drug" pp. 1-2, Retreived from the Internet : URL: http://www.pharmagap.com/cancer.html.
PharmaGap (Retrieved on Apr. 28, 2006) "PKC-alpha Inhibition" pp. 1-2, Retreived from the Internet : URL:http://www.pharmagap.com/techplat.html.
PharmaGap Annual General Meeting Presentation of Jun. 15, 2006 pp. 1-42.
PharmaGap presentation (Mar. 2005) "Science Platform." pp. 1-20.
PharmaGap Press Release dated Apr. 26, 2005 "Pharmagapreports Breastcancerand Multi-Drug Resistance Results in Bench Tests" pp. 1-2.
PharmaGap press release dated Aug. 11, 2005 "Pharmagap Announces Licensing Discussions, Funding Program, and Commencement of Efficacy Testing on Human Cancers in Mice" pp. 1-2.
PharmaGap Press Release dated Jan. 25, 2006 "Pharmagap Releases Pre-Clinical Animal Efficacy Data for Lead Drug Compound for Oncology" pp. 1-4.
PharmaGap Press Release dated Nov. 23, 2005 "Pharmagap Announces Collaboration With Leading Cancer Research Institute" pp. 1-2.
PharmaGap Press Release of Jun. 22, 2005 "PharmaGap Update at Annual Meeting" pp. 1-2.
PharmaGap Press Release of Mar. 23, 2005 "Pharmagap Success Reported in Demonstrating Effectiveness of Drug Compound on Non Small Cell Lung Cancer Cells in Laboratory Testing" pp. 1-2.
PharmaGap Press Release of Mar. 30, 2005 "Pharmagap Approved by the National Research Council to Begin Small Animal Testing Program" pp. 1-2.
Powell et al. (1996) "Persistent Membrane Translocation of Protein Kinase C α during 12-O-Tetradecanoylphorbol-13-acetate-induced Apoptosis of LNCaP Human Prostate Cancer Cells" *Cell Growth and Differentiation* 7:419-428.
Price et al. (1999) "Epidermal Growth Factor Promotes MDA-MB-231 Breast Cancer Cell Migration through a Phosphatidylinositol 3'-Kinase and Phospholipase C-dependent Mechanism" *Cancer Research* 59:5475-5478.
Puls et al. (1997) "Interaction of protein kinase C ζ with ZIP, a novel protein kinase C-binding protein" *Proc. Acad. Natl. Sci. USA* 94:6191-6196.
Reuveni et al. (2002) "Toward a PKB Inhibitor: Modification of a Selective PKA Inhibitor by Rational Design" *Biochemistry* 41:10304-14.
Romanova et al. (1998) "Cross-Talk between Protein Kinase C-α (PKC-α) and -δ (PKC-δ): PKC-α Elevates the PKC-δ Protein Level, Altering Its mRNA Transcription and Degradation" *Biochemistry* 37(16): 5558-5565.
Ron et al. "An autoregulatory region in protein kinase C: The pseudoanchoring site" *PNAS* (1995) 92:492-496.
Rosenzweig et al. (2002) "Differential Effects of Tumor Necrosis Factor-α on Protein Kinase C Isoforms α and δ Mediate Inhibition of Insulin Receptor Signaling" *Diabetes* 51:1921-1930.
Rotenberg et al. (1998) "Photoinduced Inactivation of Protein Kinase C by Dequalinium Identifies the RACK-1-binding Domain as a Recognition Site" *J. Biol. Chem*. 273(4): 2390-2395.
Rubinstein et al. (1990) "Comparison of In Vitro Anticancer-Drug-Screening Data Generated With a Tetrazolium Assay Versus a Protein Assay Against a Diverse Panel of Human Tumor Cell Lines" *J. Natl. Cancer Inst*. 82(13):1113-1118.

Sachsenmaier (2001) "Targeting Protein Kinases for Tumor Therapy." *Onkologie* 24: 346-355.
Shen (2003) "Selective Protein Kinase C Inhibitors and their Applications" *Curr. Drug Targets Cardiovasc. Haematol. Disord*. 3(4):301-307.
Smith et al. (1993) "In Vitro and In Vivo Immunopharmacological Profile of SCH 40120" *Immunopharmacol. Immunotoxicol*. 15(1):13-44.
Spatola (1983) "Peptide Backbone Modifications: A Structure-Activity Analysis of Peptides Containing Amide Bond Surrogates. Conformational Constraints and Rela." Chemistry and Biochemistry of Amino Acids Peptides and Proteins. Weinstein ed., Marcel Dekker, New York p. 267-357.
Spatola et al. (1986) "Structure-Activity Relationships of Enkephalins Containing Serially Replaced Thiomethylene Amide Bond Surrogates" *Life Sci*. 38:1243-1249.
Spatola (1983) "Peptide Backbone Modifications: A Structure-Activity Analysis of Peptides Containing Amide Bond Surrogates", *Chemistry and Biochemistry of Amino Acids, Peptides, and Proteins: A Survey of Recent Developments* 7(5):267-357.
Staudinger et al. (1995) "PICK1: A Perinuclear Binding Protein and Substrate for Protein Kinase C Isolated by the Yeast Two-hybrid System" *The Journal of Cell Biology* 128(3): 263-271.
Staudinger et al. (1997) "Specific Interaction of the PDZ Domain Protein PICK1 with the COOH Terminus of Protein Kinase C-α" *The Journal of Biological Chemistry* 272(51):32019-32024.
Swannie et al. (2002) "Protein Kinase C Inhibitors" *Curr. Oncol. Rep*. 4(1):37-46.
Tonetti et al. (2003) "Elevated protein kinase C alpha expression may be predictive of tamoxifen treatment failure" *British J. Cancer*, 88:1400-1402.
Trosko et al. (2002) "Gap Junctions as Targets for Cancer Chemoprevention and Chemotherapy" *Current Drug Targets* 3: 465-82.
Ungvari et al. (2003) "High Pressure Induces Superoxide Production in Isolated Arteries Via Protein Kinase C—Dependent Activation of NAD(P)H Oxidase" *Circulation* 108:1253-1258.
Vives et al. (2002) "The Tat-Derived Cell-Penetrating Peptide" *Cell-Penetrating Peptides: Processes and Applications* 1: 3-21.
Wang et al. (2003) "PICK1, an Anchoring Protein That Specifically Targets Protein Kinase Cα to Mitochondria Selectively upon Serum Stimulation in NIH 3T3 Cells" *J. Biol. Chem*. 278(39): 37705-37712.
Wang et al. (2004) "The V5 Domain of Protein Kinase C Plays a Critical Role in Determining the Isoform-Specific Localization, Translocation, and Biological Function of Protein Kinase C-δ and -ε" *Molecular Cancer Research* 2: 129-140.
Ward et al. (1995) "Irreversible Inactivation of Protein Kinase C by a Peptide-Substrate Analog" *J. Biol.Chem*. 270(14):8056-8060.
Ward et al. (1999) "A Peptide Substrate-Based Affinity Label Blocks Protein Kinase C-Catalyzed ATP Hydrolysis and Peptide-Substrate" *Arch. Biochem. Biophys*. 365(2):248-253.
Wasniowska et al. (2004) "The $Fy^a$, Fy6 and Fy3 epitopes of the Duffy blood group system recognized by new monoclonal antibodies: identification of a linear Fy3 epitope" *British Journal of Haematology* 124:118-122.
Wei et al. (2004) "Connexins and Cell Signalling in Development and Disease" *Annu. Rev. Cell Dev. Biol*. 20: 811-38.
West et al. (1992) "Simple Assays of Retinoid Activity as Potential Screens for Compounds That May be Useful in treatment of Psoriasis" *J. Investigative Derm*. 99:95-100.
Wright et al. (2002) "Phospholipid synthesis, diacylglycerol compartmentation, and apoptosis." *Biol. Res*., 35, 223-229.
Xu et al. (2004) "Catalytic Domain Crystal Structure of Protein Kinase C-Θ (PKC Θ)" *J. Biol. Chem*., 279 (48), 50401-50409.
Yao et al. (1994) "Protective Effects of Benidipine against Myocardial Damage Following Ischemia and Reperfusion in the Isolated Perfused Rat Heart" *Biol. Pharm. Bull*. 17(4):517-521.
Zhang et al. (2003) "Increased invasive capacity of connexin43-overexpressing malignant glioma cells" *J. Neurosurgery* 99(6):1039-46.
Zhu et al. (2006) "The very C-terminus of protein kinase Cε is critical for the full catalytic competence but its hydrophobic motif is dispensable for the interaction with 3-phosphoinositide-dependent kinase-$1^B$" *Cellular Signalling* 18: 807-818.

* cited by examiner

*Primary Examiner* — Jeffrey E Russel
(74) *Attorney, Agent, or Firm* — Weaver Austin Villeneuve & Sampson LLP; Tom Hunter

(57) ABSTRACT

Compounds that are capable of inhibiting the activity of one or more protein kinases are provided. The compounds are short, predominantly basic peptidic compounds comprising between about 5 and about 20 amino acids, and can optionally comprise an ATP mimetic moiety. The protein kinase inhibiting compounds can be used to inhibit the activity of one or more protein kinases in vitro or in vivo. Also provided are methods of inhibiting a protein kinase in a subject by administration of an effective amount of a protein kinase inhibiting compound and the use of the protein kinase inhibiting compounds, alone or in combination with other chemotherapeutic agents, in the treatment of protein kinase mediated diseases and disorders.

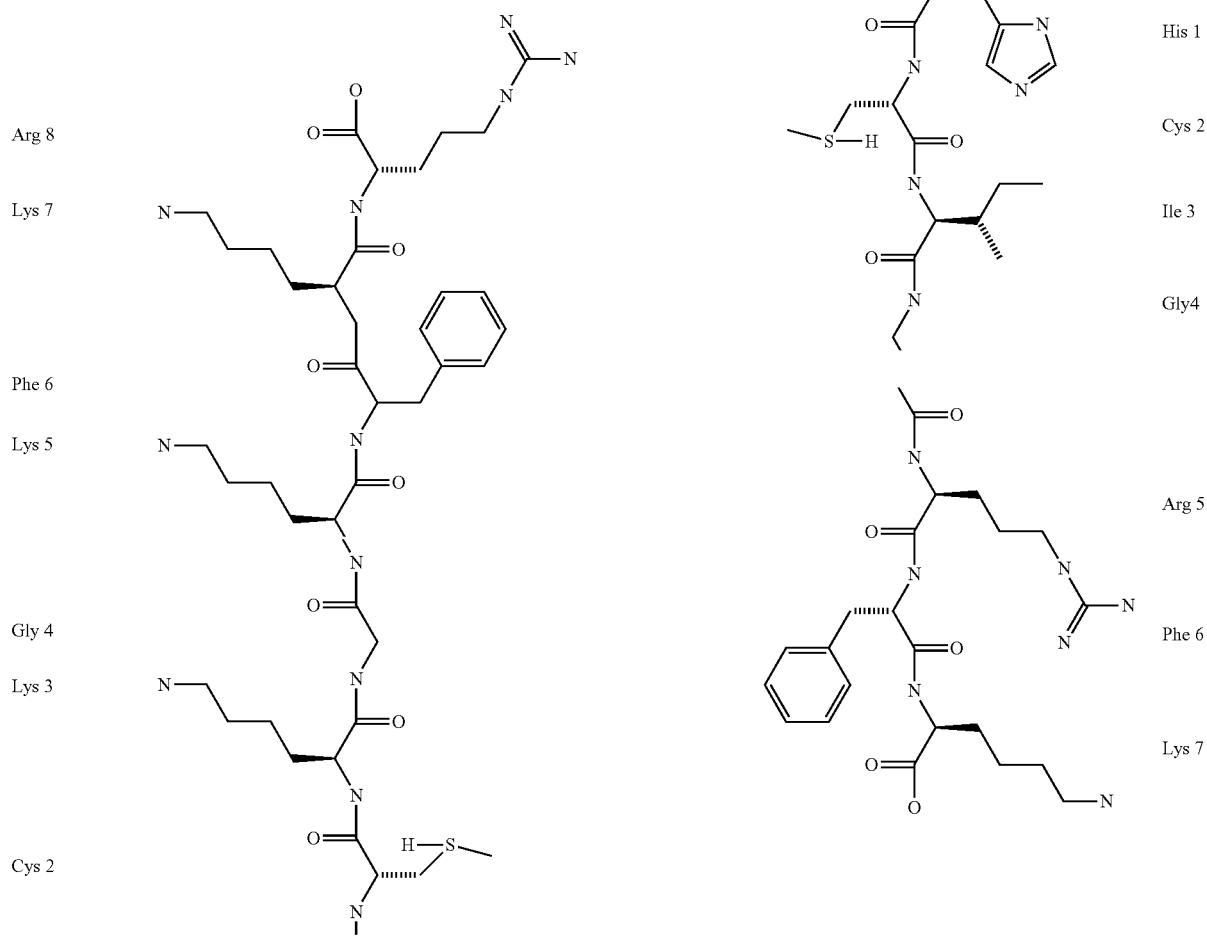
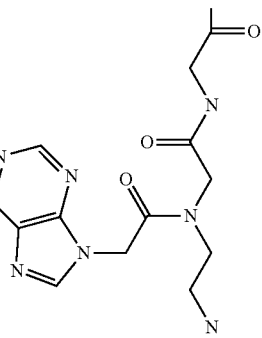
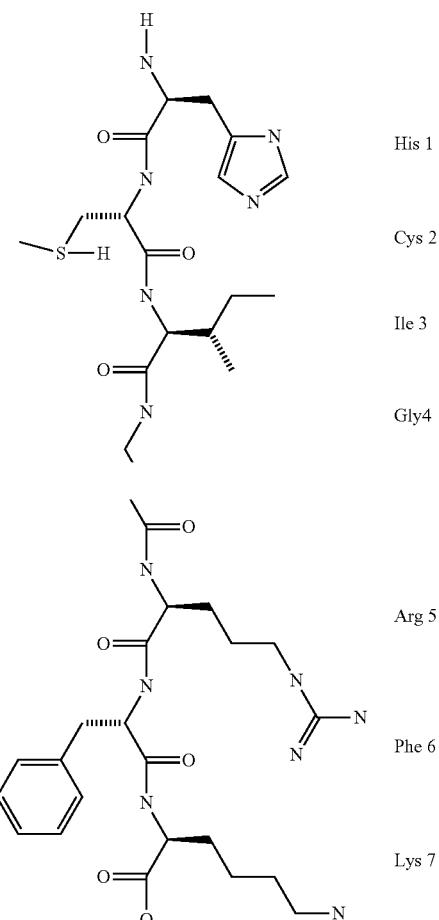

57 Claims, 48 Drawing Sheets

A.

B.

C.

D.

E.

F.

G.

H.

A.

B.

C.

D.

E.

F.

G.

H.

A.

B.

A.

B.

A.

B.

C.

A.

B.

A.

B.

A.

B.

A.

B.

INHIBITORS OF PROTEIN KINASES AND USES THEREOF

CROSS-REFERENCE TO RELATED APPLICATIONS

This application is a 371 of PCT/CA2006/000521, filed on Apr. 11, 2006, which claims priority to and benefit of U.S. Ser. No. 60/669,898, filed on Apr. 11, 2005, both of which are incorporated herein by reference in their entirety for all purposes.

FIELD OF THE INVENTION

The present invention relates to the field of protein kinases and, in particular, to inhibitors of protein kinases.

BACKGROUND OF THE INVENTION

Protein kinases (PKs) are a large class of enzymes that catalyse the transfer of the γ-phosphate from adenosine triphosphate (ATP) to the hydroxyl group on the side-chain of a serine, threonine or tyrosine residue in a substrate protein or peptide. PKs are intimately involved in the control of various important cell functions, including signal transduction, differentiation, proliferation and apoptosis. Due to their role in critical cellular functions, PKs are logical targets for now therapeutics. Inhibitors of PKs have a variety of potential therapeutic applications including in the treatment of cancer, inflammatory conditions, autoimmune disorders, neurological disorders, diabetes and cardiac diseases.

Individual PKs within the PK superfamily can be classified as either serine/threonine-specific PKs or tyrosine-specific PKs according to the residue in the substrate protein/peptide that the PK phosphorylates. Both serine/threonine and tyrosine PKs have been the target of therapeutic strategies, particularly with regard to the development of new anti-cancer therapeutics, and, as a result, a number of PK inhibitors are currently in clinical development (see reviews by Goekjian & Jirousek, *Curr. Med. Chem.* (1999) 6:877-903; Goekjian & Jirousek, *Expert Opin. Investig. Drugs* (2001) 10:2117-2140; Sachsenmaier, *Onkologie* (2001) 24:346-355; Swannie & Kaye, *Curr. Oncology Rep.* (2002) 4:37-46, and Dancey & Sausville, *Nat Rev Drug Discov.* (2003) 2:296-313). Most of the PK inhibitors in clinical development are natural product analogues (for example, staurosporin or bryostatin analogues), small molecule inhibitors, monoclonal antibodies or antisense oligonucleotides.

A number of peptide-based PK inhibitors have also been described. For example, U.S. Pat. No. 4,582,821 describes peptide and amino acid halomethyl ketones that inhibit the activity of cAMP-independent serine or tyrosine PKs. U.S. Pat. No. 6,090,929 describes protein-binding fragments of gravin that can be used as inhibitors of cAMP-dependent protein kinase (protein kinase A or PKA) or protein kinase C (PKC). International Patent Application No. PCT/US99/22106 (WO 00/18895) and U.S. Patent Application No. 2002/0160478 describe peptide inhibitors of PKs that are derived from the sequence of the αD region of a PK. U.S. Patent Application Nos. 2002/0137141 and 2002/0115173 describe peptide inhibitors of PKs that are derived from the sequence of the A region of a PK. U.S. Patent Application No. 2002/0049301 and U.S. Pat. No. 6,174,993 describe peptide inhibitors of serine/threonine PKs that are derived from the sequence of the HJ loop of a serine/threonine PK, and International Patent Application No. PCT/US00/32852 (WO 01/42280) describes peptide inhibitors of PKs that are derived from the sequence of the B4-5 region of a PK. International Patent Application No. PCT/EP93/00816 (WO 93/20101) describes peptide inhibitors that specifically target PKC isotype zeta.

Peptide inhibitors that spontaneously form intermolecular disulphide bridges with the active site region of PKC isoforms have also been described (Ward et al., (1995) *J. Biol. Chem.* 270:8056-8060; Ward et al., *Arch. Biochem. Biophys.* (1999) 365:248-253). The peptides have the sequences RKRCLRRL (SEQ ID NO:27) and RRRCLRRL (SEQ ID NO:28) and, due to the nature of their interaction with the PKC enzyme, their inhibition of these enzymes is sensitive to reducing agents, such as dithiothreitol.

Various methods of identifying or optimising PK inhibitors have also been described. U.S. Patent Application No. 2003/0143656, for example, describes a method of identifying compounds that modulate PK activity based on the identification of a small hydrophobic pocket on the small lobe of PKA and the observation that compounds that interact with this hydrophobic pocket can modulate the activity and/or stability of a PK. International Patent Application No. PCT/US00/00803 (WO 00/42213) describes a modular strategy for developing non-peptidic PK inhibitors, which comprise a first module (M1) having functional groups that bind catalytic residues of the PK and a second module (M2) that provides a non-peptide scaffold.

The strategy involves a first step to identify suitable M1 modules that comprises binding candidate modules to a pentapeptide scaffold. Subsequent steps replace the pentapeptide with a non-peptide scaffold.

Other PK inhibitors have been described that include a peptide linked to ATP, or a derivative thereof. Medzihradszky et al. (*J. Am. Chem. Soc.* (1994) 116:9413-9419) describe potential cAMP-dependent protein kinase inhibitors that comprise ATP, ADP or adenosine tetraphosphate linked to the oxygen atom in the side-chain of the serine residue in kemptide, a known peptide substrate for cAMP-dependent protein kinase having the sequence LRRASLG (SEQ ID NO:29). U.S. Patent Application No. 2002/0031820 and Parang et al. (*Nature Struc. Biol.* (2001) 8:37-41) describe a similar type of inhibitor for inhibition of the insulin receptor tyrosine kinase or PKA that comprises ATPγS linked to a peptide substrate analogue by a two-carbon linker. U.S. Patent Application No. 2005/0026840 describes inhibitors of PKB that comprise small molecules having affinity for the ATP binding site of PKB, specifically small molecules comprising an isoquinoline, dansyl, quinoline or napthalene ring, conjugated to a peptide that mimics a PKB substrate.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide inhibitors of protein kinases and uses thereof. In accordance with one aspect of the present invention, there is provided a peptidic compound comprising between about 5 and about 20 amino acids and having the general Formula (I):

$$(C1)J(M)\text{-}N_yB_zA_xB_yN_yB_x \quad \text{(I)}$$

wherein:
  C1 is $N_xB_y(A/N)_xB_yN_y$ and is attached to J by a peptide bond from the N- or C-terminus of C1;

J is 1-4 amino acid residues selected from the group of: Cys, Lys and His;

M is absent or an ATP mimetic moiety optionally linked to an amino acid selected from the group of Ile, Leu, Val or Gly and is attached to J via the side chain or the N-terminus of one of the Lys residues of J or the N-terminus of one of the Cys residues of J;

each N is independently Ala, Ile, Leu, Val or Gly;
each B is independently Arg, Lys or Tyr, and
each A is independently Phe, His or Trp;
each x is independently 0-1;
each y is independently 0-2;
z=0-3, and
the sequence $N_yB_zA_xB_yN_yB_x$ is 2 or more amino acids in length, wherein:
when J comprises one or no Cys residues, the compound of Formula (I) comprises a single peptide chain and C1 is attached to the N-terminal amino acid of J via a peptide bond from the C-terminus of C1, and when J comprises two or more Cys residues, at least two of the Cys residues are linked by a disulphide bond and the compound of Formula (I) thereby comprises a first peptide chain comprising a first of said at least two Cys residues and C1, and a second peptide chain comprising a second of said at least two Cys residues and the sequence -$N_yB_zA_xB_yN_yB_x$, wherein if M is absent, the sequence -$N_yB_zA_xB_yN_yB_x$ contains at least one of Phe or Trp, and wherein said peptidic compound is capable of inhibiting one or more protein kinases.

In accordance with another aspect of the present invention, the peptidic compound of Formula (I) is of Formula (II):

$$(C1)J(M)-N_yB_zA_xB_yN_y \qquad (II)$$

wherein:
C1 is $N_xB_y(A/N)_xB_yN_y$ and is attached to J by a peptide bond from the N- or C-terminus of C1;

J is 1-4 amino acid residues selected from the group of: Cys, Lys and His;

M is absent or an ATP mimetic moiety optionally linked to an amino acid selected from the group of Ile, Leu, Val or Gly and is attached to J via the side chain or the N-terminus of one of the Lys residues of J or the N-terminus of one of the Cys residues of J;

each N is independently Ala, Ile, Leu, Val or Gly;
each B is independently Arg, Lys or Tyr; and
each A is independently Phe, His or Trp;
each x is independently 0-1;
each y is independently 0-2;
z=0-3, and
the sequence $N_yB_zA_xB_yN_y$ is 2 or more amino acids in length, and wherein:
when J comprises one or no Cys residues, the compound of Formula (I) comprises a single peptide chain and C1 is attached to the N-terminal amino acid of J via a peptide bond from the C-terminus of C1, and when J comprises two or more Cys residues, at least two of the Cys residues are linked by a disulphide bond and the compound of Formula (I) thereby comprises a first peptide chain comprising a first of said at least two Cys residues and C1, and a second peptide chain comprising a second of said at least two Cys residues and the sequence -$N_yB_zA_xB_yN_yB_x$.

In accordance with another aspect of the present invention, the peptidic compound of Formula (I) is of Formula (III):

$$(C2)J(M)-N_yB_zA_xB_yN_y \qquad (III)$$

wherein:
C2 is $B_y(A/N)_xB_yN_y$ and is attached to J by a peptide bond from the N- or C-terminus of C2;

J comprises two Cys residues and optionally 1-2 residues selected from His and Lys, the Cys residues are linked by a disulphide bond and the compound of Formula (I) thereby comprises a first peptide chain comprising a first of said two Cys residues and C2, and a second peptide chain comprising a second of said two Cys residues and the sequence -$N_yB_zA_x$-$B_yN_yB_x$, M is an ATP mimetic moiety optionally linked to an amino acid selected from the group of Ile, Leu, Val or Gly and is attached to J via the N-terminus of one of the Cys residues;

each N is independently Ala, Ile, Leu, Val or Gly;
each B is independently Arg, Lys or Tyr; and
each A is independently Phe, His or Trp;
each x is independently 0-1;
each y is independently 0-2, and
z=0-3.

In accordance with another aspect of the present invention, the peptidic compound of Formula (I) is of Formula (IV):

$$N_xB_y(A/N)_xB_yN_y-J(M)-N_yB_zA_xB_yN_yB_x \qquad (IV)$$

wherein:
J is 1-2 Lys residues or a Cys residue;
M is absent or is an ATP mimetic moiety attached to J via the side chain of one of the Lys residues or the N-terminus of the cysteine residue;

each N is independently Ala, Ile, Leu, Val or Gly;
each B is independently Arg, Lys or Tyr; and
each A is independently Phe, His or Trp;
each x is independently 0-1;
each y is independently 0-2, and
z=0-3.

In accordance with another aspect of the present invention, the peptidic compound of Formula (I) is selected from the group of:

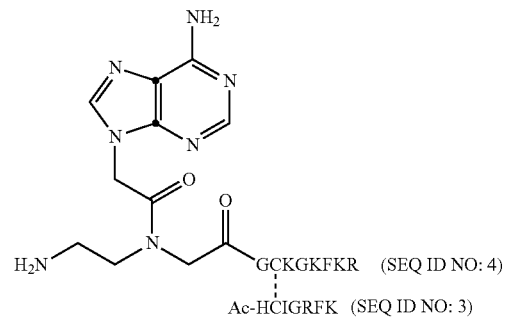

Ac-HCIGRFK  (SEQ ID NO: 3)
GCKGKFKR  (SEQ ID NO: 4)

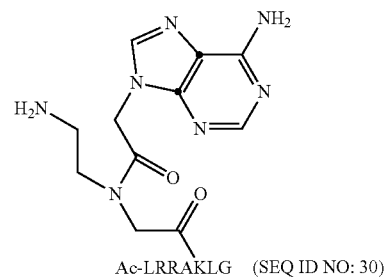

Ac-LRRAKLG  (SEQ ID NO: 30)

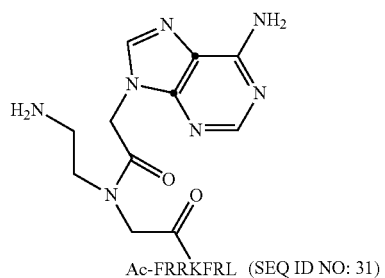
Ac-FRRKFRL (SEQ ID NO: 31)
Ac-FRRCFRL (SEQ ID NO: 32)
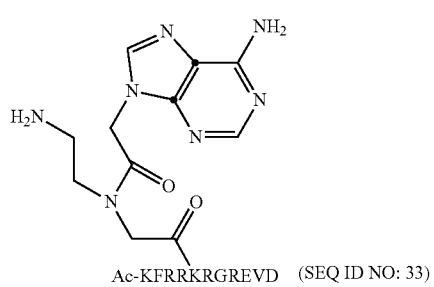
Ac-KFRRKRGREVD (SEQ ID NO: 33)
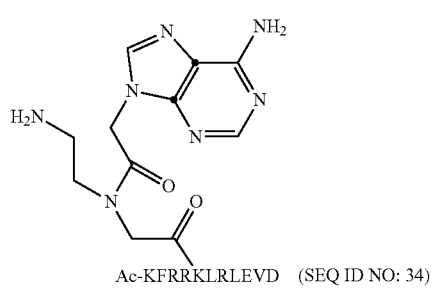
Ac-KFRRKLRLEVD (SEQ ID NO: 34)
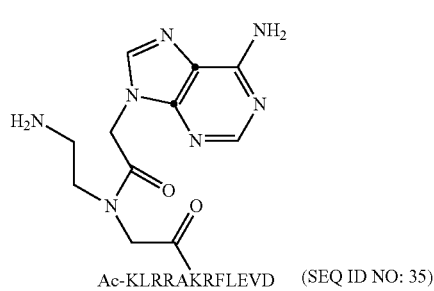
Ac-KLRRAKRFLEVD (SEQ ID NO: 35)
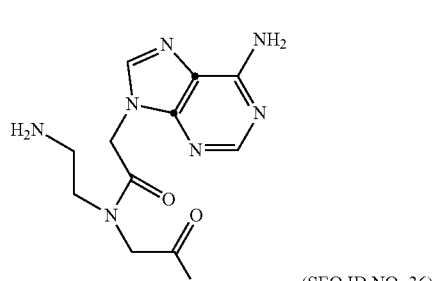
Ac-KLRRAKLGLGDD (SEQ ID NO: 36)
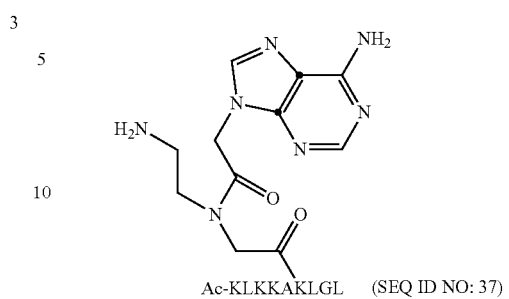
Ac-KLKKAKLGL (SEQ ID NO: 37)
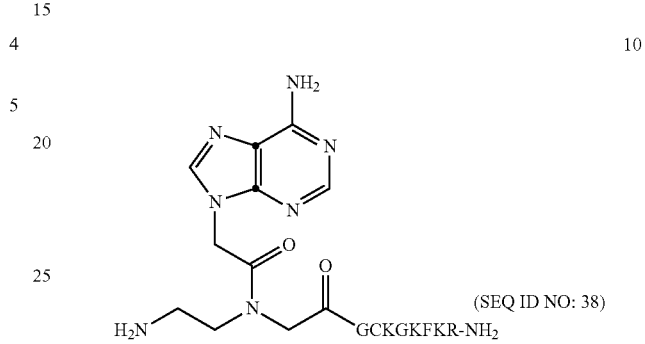
GCKGKFKR-NH$_2$ (SEQ ID NO: 38)
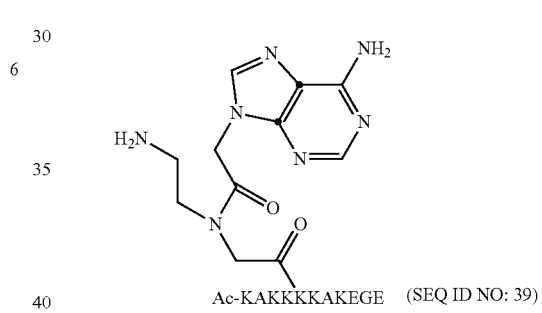
Ac-KAKKKKAKEGE (SEQ ID NO: 39)
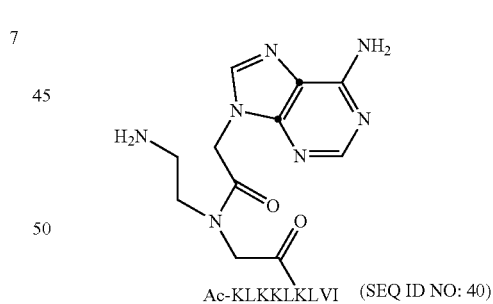
Ac-KLKKLKLVI (SEQ ID NO: 40)
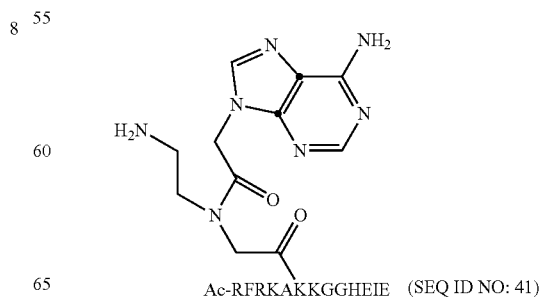
Ac-RFRKAKKGGHEIE (SEQ ID NO: 41)

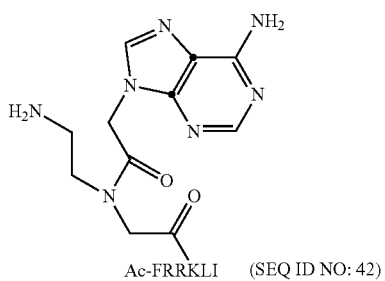

Ac-FRRKLI (SEQ ID NO: 42)

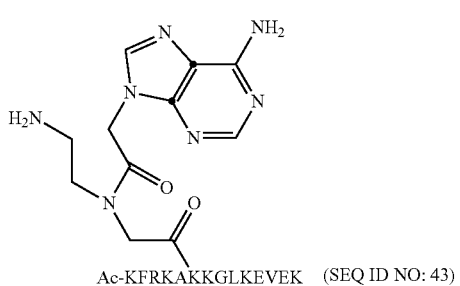

Ac-KFRKAKKGLKEVEK (SEQ ID NO: 43)

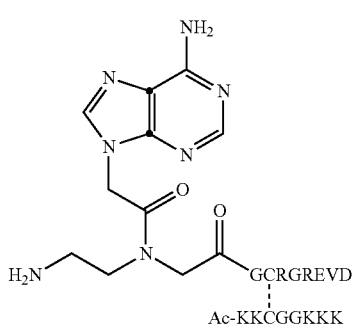

Ac-KKCGGKKK

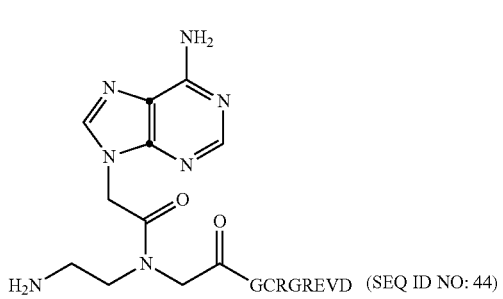

GCRGREVD (SEQ ID NO: 44)

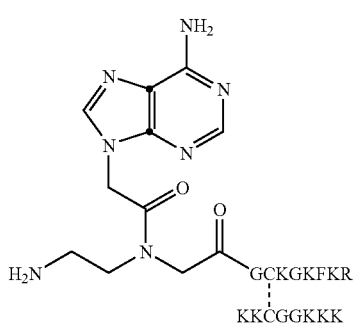

and

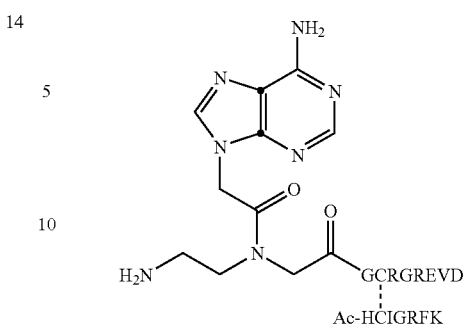

Ac-HCIGRFK

In accordance with another aspect of the present invention, there is provided a composition comprising the peptidic compound of Formula (I).

In accordance with another aspect of the present invention, there is provided a peptidic compound of Formula (I) for use to inhibit a protein kinase.

In accordance with another aspect of the present invention, there is provided a peptidic compound of Formula (I), for use in the treatment of a protein kinase mediated disease or disorder.

In accordance with another aspect of the present invention, there is provided a peptidic compound of Formula (I), for use to inhibit the proliferation of cancer cells.

In accordance with another aspect of the present invention, there is provided a use of the peptidic compound of Formula (I) for the manufacture of a medicament.

In accordance with another aspect of the present invention, there is provided a method of inhibiting a protein kinase in a subject comprising administering to said subject an effective amount of the peptidic compound of Formula (I).

In accordance with another aspect of the present invention, there is provided a method of inhibiting the proliferation of cancer cells comprising contacting said cancer cells with an effective amount of the peptidic compound of Formula (I).

In accordance with another aspect of the present invention, there is provided a method of treating a protein kinase mediated disease or disorder in a subject comprising administering to said subject an effective amount of the peptidic compound of Formula (I).

BRIEF DESCRIPTION OF THE DRAWINGS

These and other features of the invention will become more apparent in the following detailed description in which reference is made to the appended drawings.

DETAILED DESCRIPTION OF THE INVENTION

Figure 1:
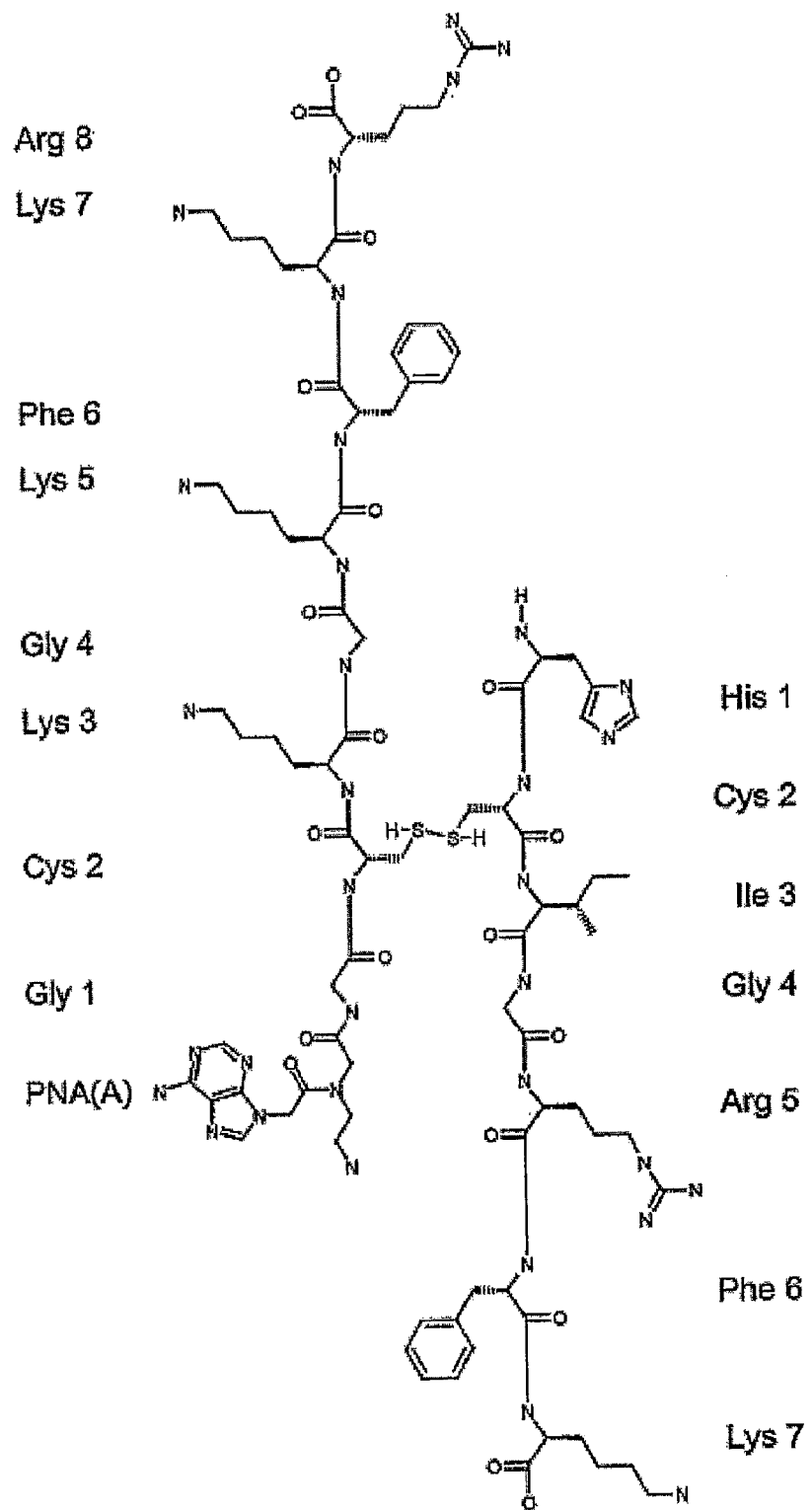
FIG. 1 presents a schematic diagram of the structure of a protein kinase inhibiting compound in accordance with one embodiment of the present invention (H atoms omitted) (GCKGKFKR (SEQ ID NO:4), HCIGRFK (SEQ ID NO:3).

The present invention provides for compounds that are capable of inhibiting the activity of one or more protein kinases. The compounds of the present invention are short, predominantly basic peptidic compounds comprising between about 5 and about 20 amino acids, which can optionally comprise an ATP mimetic moiety. In the context of the present invention, the "ATP mimetic moiety" requires only the presence of the adenine portion of ATP, or a derivative of adenine, without the sugar or its triphosphate side group.

The compounds of the present invention are capable of inhibiting the activity of protein kinase C alpha (PKCα) and at least one other protein kinase. While the present invention is not limited to any particular theory or mechanism, it is believed that the protein kinase inhibiting compounds of the present invention interact with key amino acid residues in the catalytic domain of the target protein kinase, which would normally interact with the substrate/pseudosubstrate and/or the ATP co-substrate, and thereby interfere with the catalytic activity of the target protein kinase. Accordingly, in one embodiment, the compounds of the present invention are capable of inhibiting protein kinases having a similar catalytic site structure to PKCα. In another embodiment, the compounds of the present invention are capable of inhibiting the activity of PKCα and one or both of protein kinase A (PKA) and MAPKp38.

The present invention provides for the use of the protein kinase inhibiting compounds to inhibit the activity of one or more protein kinases in vitro or in vivo. The present invention further provides for methods of inhibiting one or more protein kinases in a subject by administration of an effective amount of a protein kinase inhibiting compound of the invention. Protein kinases have been implicated in a variety of diseases and disorders. Accordingly, the present invention contemplates the use of the protein kinase inhibiting compounds, alone or in combination with other chemotherapeutic agents, in the treatment of protein kinase mediated diseases and disorders such as, cancer, psoriasis, angiogenesis, restenosis, atherosclerosis, cardiovascular disease, hypertension, diabetes, neurological disorders, rheumatoid arthritis, kidney disorders, inflammatory disorders and autoimmune disorders.

In accordance with one embodiment of the present invention, the protein kinase inhibiting compounds are capable of inhibiting cancer cell proliferation and can be used, alone or in combination with other chemotherapeutic agents, in the treatment of cancer.

DEFINITIONS

Unless defined otherwise, all technical and scientific terms used herein have the same meaning as commonly understood by one of ordinary skill in the art to which this invention pertains.

The term "inhibit," as used herein, means to slow-down, reduce, delay or prevent.

The terms "therapy" and "treatment," as used interchangeably herein, refer to an intervention performed with the intention of improving a subject's status. The improvement can be subjective or objective and is related to ameliorating the symptoms associated with, preventing the development of, or altering the pathology of a disease or disorder being treated. Thus, the terms therapy and treatment are used in the broadest sense, and include the prevention (prophylaxis), moderation, reduction, and curing of a disease or disorder at various stages. Preventing deterioration of a subject's status is also encompassed by the term. Subjects in need of therapy/treatment thus include those already having the disease or disorder as well as those prone to, or at risk of developing, the disease or disorder and those in whom the disease or disorder is to be prevented.

The term "ameliorate" includes the arrest, prevention, decrease, or improvement in one or more the symptoms, signs, and features of the disease or disorder being treated, both temporary and long-term.

The term "subject" or "patient" as used herein refers to an animal in need of treatment.

The term "animal," as used herein, refers to both human and non-human animals, including, but not limited to, mammals, birds and fish.

The term "naturally-occurring," as used herein with reference to an object, such as a protein, peptide or amino acid, indicates that the object can be found in nature. For example, a protein, peptide or amino acid that is present in an organism or that can be isolated from a source in nature and which has not been intentionally modified by man in the laboratory is considered to be naturally-occurring.

The term "retro sequence" as used herein, refers to a sequence of amino acids that has been altered with respect to a reference amino acid sequence by a reversal of the direction of the reference amino acid sequence. For example, for a reference sequence "ATPKL" (SEQ ID NO:45), the retro sequence would be "LKPTA" (SEQ ID NO:46).

As used herein, the term "about" refers to a +/−10% variation from the nominal value. It is to be understood that such a variation is always included in any given value provided herein, whether or not it is specifically referred to.

The term "alkyl," as used herein, refers to a straight chain or branched hydrocarbon of one to ten carbon atoms or a cyclic hydrocarbon group of three to ten carbon atoms. Said alkyl group is optionally substituted with one or more substituents independently selected from the group of: alkyl, alkenyl, alkynyl, aryl, heteroalkyl, aralkyl, hydroxy, alkoxy, aralkyloxy, aryloxy, carboxy, acyl, aroyl, halo, nitro, trihalomethyl, cyano, alkoxycarbonyl, aryloxycarbonyl, aralkoxycarbonyl, acylamino, aroylamino, dialkylamino, carbamoyl, alkylcarbamoyl, dialkylcarbamoyl, alkylthio, aralkylthio, arylthio, alkylene and $NZ_1Z_2$ where $Z_1$ and $Z_2$ are independently hydrogen, alkyl, aryl, and aralkyl. This term is exemplified by such groups as methyl, ethyl, n-propyl, i-propyl, n-butyl, t-butyl, l-butyl (or 2-methylpropyl), cyclopropylmethyl, i-amyl, n-amyl, hexyl, cyclopropyl, cyclobutyl, cyclopentyl, and the like.

The term "alkenyl" refers to a straight chain or branched hydrocarbon of two to ten carbon atoms having at least one carbon to carbon double bond. Said alkenyl group can be optionally substituted with one or more substituents as defined above. Exemplary groups include allyl and vinyl.

The term "alkynyl" refers to a straight chain or branched hydrocarbon of two to ten carbon atoms having at least one carbon to carbon triple bond. Said alkynyl group can be optionally substituted with one or more substituents as defined above. Exemplary groups include ethynyl and propargyl.

The term "heteroalkyl," as used herein, refers to an alkyl group of 2 to 10 carbon atoms, wherein at least one carbon is replaced with a hetero atom, such as N, O or S.

The term "aryl" (or "Ar"), as used herein, refers to an aromatic carbocyclic group containing about 6 to about 10 carbon atoms or multiple condensed rings in which at least one ring is aromatic carbocyclic group containing 6 to about 10 carbon atoms. Said aryl or Ar group can be optionally substituted with one or more substituents as defined above. Exemplary aryl groups include phenyl, tolyl, xylyl, biphenyl, naphthyl, 1,2,3,4-tetrahydronaphthyl, anthryl, phenanthryl, 9-fluorenyl, and the like.

The term "aralkyl," as used herein, refers to a straight or branched chain alkyl, alkenyl or alkynyl group, wherein at least one of the hydrogen atoms is replaced with an aryl group, wherein the aryl group can be optionally substituted with one or more substituents as defined above. Exemplary aralkyl group include benzyl, 4-phenylbutyl, 3,3-diphenylpropyl and the like.

The term "alkoxy," as used herein, refers to RO—, wherein R is alkyl, alkenyl or alkynyl in which the alkyl, alkenyl and alkynyl groups are as previously described. Exemplary alkoxy groups include methoxy, ethoxy, n-propoxy, I-propoxy, n-butoxy, and heptoxy.

The term "aryloxy" as used herein, refers to an "aryl-O—" group in which the aryl group is as previously described. Exemplary aryloxy groups include phenoxy and naphthoxy.

The term "alkylthio," as used herein, refers to RS—, wherein R is alkyl, alkenyl or alkynyl in which the alkyl, alkenyl and alkynyl groups are as previously described. Exemplary alkylthio groups include methylthio, ethylthio, I-propylthio and heptylthio.

The term "arylthio," as used herein, refers to an "aryl-S—" group in which the aryl group is as previously described. Exemplary arylthio groups include phenylthio and naphthylthio.

The term "aralkyloxy," as used herein, refers to an "aralkyl-O—" group in which the aralkyl group is as previously described. Exemplary aralkyloxy groups include benzyloxy.

The term "aralkylthio," as used herein, refers to an "aralkyl-S—" group in which the aralkyl group is as previously described. Exemplary aralkylthio groups include benzylthio.

The term "dialkylamino," as used herein, refers to an —$NZ_1Z_2$ group wherein $Z_1$ and $Z_2$ are independently selected from alkyl, alkenyl or alkynyl, wherein alkyl, alkenyl and alkynyl are as previously described. Exemplary dialkylamino groups include ethylmethylamino, dimethylamino and diethylamino.

The term "alkoxycarbonyl," as used herein, refers to R—O—CO—, wherein R is alkyl, alkenyl or alkynyl, wherein alkyl, alkenyl and alkynyl are as previously described. Exemplary alkoxycarbonyl groups include methoxy-carbonyl and ethoxy-carbonyl.

The term "aryloxycarbonyl," as used herein, refers to an "aryl-O—CO—", wherein aryl is as defined previously. Exemplary aryloxycarbonyl groups include phenoxy-carbonyl and naphthoxy-carbonyl.

The term "aralkoxycarbonyl," as used herein, refers to an "aralkyl-O—CO—," wherein aralkyl is as defined previously. Exemplary aralkoxycarbonyl groups include benzyloxycarbonyl.

The term "acyl" as used herein, refers to RC(O)—, wherein R is alkyl, alkenyl, alkynyl, heteroalkyl, a heterocyclic ring, or a heteroaromatic ring, wherein alkyl, alkenyl, alkynyl, heteroalkyl, heterocyclic, and heteroaromatic are as defined previously.

The term "aroyl" as used herein, refers to an ARC(O)— group, wherein Ar is as defined previously.

The term "carboxy" as used herein, refers to ROC(O)—, wherein R is H, alkyl, alkenyl or alkynyl, and wherein alkyl, alkenyl or alkynyl are as defined previously.

The term "carbamoyl," as used herein, refers to a $H_2N$—CO— group.

The term "alkylcarbamoyl," as used herein, refers to an "$Z_1Z_2N$—CO—" group wherein one of the $Z_1$ and $Z_2$ is hydrogen and the other of $Z_1$ and $Z_2$ is independently selected from alkyl, alkenyl or alkynyl and wherein alkyl, alkenyl and alkynyl are as defined previously.

The term "dialkylcarbamoyl," as used herein, refers to a "$Z_1Z_2N$—CO—" group wherein $Z_1$ and $Z_2$ are independently selected from allyl, alkenyl or alkynyl and wherein alkyl, alkenyl and alkynyl are as defined previously.

The term "acylamino", as used herein, refers to an "acyl-NH—" group, wherein acyl is as defined previously.

The term "halo" as used herein, refers to fluoro, chloro, bromo or iodo. In one embodiment, "halo" refers to fluoro, chloro or bromo.

Other chemistry terms herein are used according to conventional usage in the art, as exemplified by The McGraw-Hill Dictionary of Chemical Terms (ed. Parker, S., 1985), McGraw-Hill, San Francisco).

Naturally-occurring amino acids are identified throughout by the conventional three-letter or one-letter abbreviations indicated below, which are generally accepted in the peptide art and recommended by the IUPAC-IUB commission in biochemical nomenclature:

TABLE 1

Amino acid codes

| Name | 3-letter code | 1-letter code |
|---|---|---|
| Alanine | Ala | A |
| Arginine | Arg | R |
| Asparagine | Asn | N |
| Aspartic | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The peptide sequences set out herein are written according to the generally accepted convention whereby the N-terminal amino acid is on the left and the C-terminal amino acid is on the right. By convention, L-amino acids are represented by upper case letters and D-amino acids by lower case letters.

Protein Kinase Inhibiting (PKI) Compounds

The protein kinase inhibiting (PKI) compounds of the present invention are short, predominantly basic peptidic compounds. In one embodiment, the PKI compounds comprise an ATP mimetic moiety attached to a peptide sequence. The PKI inhibitors of the present invention are designed such that they are able to interact with and inhibit protein kinase C alpha (PKCα). The PKI compounds can also inhibit one or more other protein kinases due to the structural similarities between the catalytic sites of various protein kinases. Thus, in accordance with one aspect of the invention, the PKI compounds are broad-spectrum inhibitors that are capable of inhibiting various classes of protein kinases, including tyrosine-specific protein kinases and serine/threonine-specific protein kinases. In one embodiment of the invention, the compounds are capable of inhibiting the activity of PKCα and one or more other serine/threonine-specific protein kinases. Examples of serine/threonine-specific protein kinases include, but not limited to, protein kinase A, protein kinase B (Akt), various protein kinase C isoforms, and MAPKp38. In another embodiment, the PKI compounds are capable of inhibiting the activity of one or more protein kinase C isoforms.

Protein kinases are ubiquitous enzymes and can be found in plants, algae, viruses, bacteria and animals, including higher animals, such as mammals. In one embodiment of the invention, the compounds are capable of inhibiting the activity of one or more mammalian protein kinases. In another embodiment, the compounds are capable of inhibiting the activity of one or more human protein kinases.

The protein kinase inhibiting (PKI) compounds of the present invention are peptidic compounds comprising between about 5 and about 20 amino acids and have the general Formula (I):

wherein:
C1 is $N_xB_y(A/N)_xB_yN_y$, and is attached to J by a peptide bond from the N- or C-terminus of C1;
J is 1-4 amino acid residues selected from the group of: Cys, Lys and Ilis;
M is absent or an ATP mimetic moiety optionally linked to an amino acid selected from the group of Ile, Leu, Val or Gly and is attached to J via the side chain or the N-terminus of one of the Lys residues of J or the N-terminus of one of the Cys residues of J;
each N is independently Ala, Ile, Leu, Val or Gly;
each B is independently Arg, Lys or Tyr, and
each A is independently Phe, His or Trp;
each x is independently 0-1;
each y is independently 0-2;
z=0-3, and
the sequence $N_yB_zA_xB_yN_yB_x$ is 2 or more amino acids in length,
wherein:
when J comprises one or no Cys residues, the compound of Formula (I) comprises a single peptide chain and C1 is attached to the N-terminal amino acid of J via a peptide bond from the C-terminus of C1, and
when J comprises two or more Cys residues, at least two of the Cys residues are linked by a disulphide bond and the compound of Formula (I) thereby comprises a first peptide chain comprising a first of said at least two Cys residues and C1, and a second peptide chain comprising a second of said at least two Cys residues and the sequence $-N_yB_zA_xB_yN_yB_x$, and
wherein if M is absent, the sequence $-N_yB_zA_xB_yN_yB_x$ contains at least one of Phe or Trp.

One skilled in the an will appreciate that when M comprises an Ile, Leu, Val or Gly residue, the ATP moiety can be directly linked to J, or it can be attached to J via the Ile, Leu, Val or Gly residue. Similarly, when J comprises two Cys residues linked by a disulphide bond and one or two other amino acids selected from Cys, His or Lys, C1 and the sequence $-N_yB_zA_xB_yN_yB_x$ can be attached directly to the respective Cys residues making up the disulphide bond, or via one or more intervening Cys, His or Lys residues.

In one embodiment of the present invention, the PKI compounds of Formula (I) comprise a modified N-terminus and/or C-terminus.

In another embodiment of the present invention, the PKI compound of Formula (I) is modified at a C-terminus to include a "tag" of between 1 to 4 amino acids in length that comprises one or more acidic amino acid residues. Other non-acidic amino acid residues included in the tag are selected from the group of: Gly, Val, Ile, Leu and Lys. Examples of suitable tags that can be added at the C-terminus of the PKI compounds include, but are not limited to Glu-Val-Glu, Asp-Asp, Glu-Gly-Glu, Glu-Ile-Glu, Glu-Val-Glu-Lys (SEQ ID NO:47), and Glu-Val-Asp.

In another embodiment, J comprises two Cys residues linked by a disulphide bond and the compound of Formula (I) thereby comprises a first peptide chain comprising C1 attached to the N- or C-terminus of the first of said two Cys residues, and a second peptide chain comprising the sequence -$N_yB_zA_xB_yN_yB_x$ attached to the C-terminus the second of said two Cys residues.

In another embodiment, J comprises two Cys residues linked by a disulphide bond and the compound of Formula (I) thereby comprises a first peptide chain comprising C1 attached to the C-terminus of the first of said two Cys residues, and a second peptide chain comprising the sequence -$N_yB_zA_xB_yN_yB_x$ attached to the C-terminus the second of said two Cys residues.

In another embodiment of the present invention, in the PKI compounds of Formula (I), each of C1 and -$N_yB_zA_xB_yN_yB_x$ are two or more amino acid residues in length. In another embodiment of the present invention, in the PKI compounds of Formula (I), -$N_yB_zA_xB_yN_yB_x$ is 3 or more amino acid residues in length. In a further embodiment, at least one of C1 and -$N_yB_zA_xB_yN_yB_x$ is 3 or more amino acid residues in length. In another embodiment, both C1 and -$N_yB_zA_xB_yN_yB_x$ are 3 or more amino acid residues in length. In another embodiment, each of C1 and $N_yB_zA_xB_yN_y$ are 4 or more amino acid residues in length.

In another embodiment of the present invention, the PKI compounds of Formula (I) have the general Formula (II):

wherein:
C1 is $N_xB_y(A/N)_xB_yN_y$ and is attached to J by a peptide bond from the N- or C-terminus of C1;
J is 1-4 amino acid residues selected from the group of: Cys, Lys and His;
M is absent or an ATP mimetic moiety optionally linked to an amino acid selected from the group of Ile, Leu, Val or Gly and is attached to J via the side chain or the N-terminus of one of the Lys residues of J or the N-terminus of one of the Cys residues of J;
each N is independently Ala, Ile, Leu, Val or Gly;
each B is independently Arg, Lys or Tyr, and
each A is independently Phe, His or Trp;
each x is independently 0-1;
each y is independently 0-2;
z=0-3, and
the sequence $N_yB_zA_xB_yN_y$ is 2 or more amino acids in length, and
wherein:
when J comprises one or no Cys residues, the compound of Formula (I) comprises a single peptide chain and C1 is attached to the N-terminal amino acid of J via a peptide bond from the C-terminus of C1, and
when J comprises two or more Cys residues, at least two of the Cys residues are linked by a disulphide bond and the compound of Formula (I) thereby comprises a first peptide chain comprising a first of said at least two Cys residues and C1, and a second peptide chain comprising a second of said at least two Cys residues and the sequence -$N_yB_zA_xB_yN_yB_x$.

In another embodiment of the present invention, the PKI compounds of Formula (I) have the general Formula (III):

wherein:
C2 is $B_y(A/N)_xB_yN_y$ and is attached to J by a peptide bond from the N- or C-terminus of C2;

J comprises two Cys residues and optionally 1-2 residues selected from His and Lys, the Cys residues are linked by a disulphide bond and the compound of Formula (I) thereby comprises a first peptide chain comprising a first of said two Cys residues and C2, and a second peptide chain comprising a second of said two Cys residues and the sequence -$N_yB_zA_xB_yN_yB_x$,
M is an ATP mimetic moiety optionally linked to an amino acid selected from the group of Ile, Leu, Val or Gly and is attached to J via the N-terminus of one of the Cys residues of J; and
N, B, A, x, y and z are as defined for Formula (I) above.

In a further embodiment, the PKI compounds have the general Formula (III) wherein:
J comprises two Cys residues and optionally 1-2 residues selected from His and Lys, the Cys residues are linked by a disulphide bond and the compound of Formula (I) thereby comprises a first peptide chain comprising C2 attached to the C-terminus of a first of said two Cys residues, and a second peptide chain comprising the sequence -$N_yB_zA_xB_yN_yB_x$ attached to the C-terminus of a second of said two Cys residues.

In another embodiment of the present invention, the PKI compounds of Formula (I) have the general Formula (IV):

wherein:
J is 1-2 Lys residues or a Cys residue;
M is absent or is an ATP mimetic moiety attached to J via the side chain of one of the Lys residues of J or the N-terminus of the cysteine residue of J; and
N, B, A, x, y and z are as defined for Formula (I) above.

In another embodiment of the present invention, the PKI compounds of Formula (I) have the general Formula (V):

wherein:
J is 1-2 Lys residues;
M is an ATP mimetic moiety attached to J via the side chain of one of the Lys residues; and
N, B, A, x, y and z are as defined for Formula (I) above.

In another embodiment of the present invention, the PKI compounds of Formula (I) have the general Formula (VI):

wherein:
J comprises a Cys residue and optionally 1-2 residues selected from His and Lys; and
N, B, A, x, y and z are as defined for Formula (I) above.

In a further embodiment of the present invention, the PKI compounds of Formula (I) have a formula selected from the group of:

Formula (VII):

Formula (VIII):

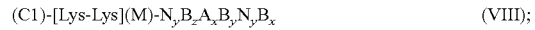

Formula (IX):

Formula (X):

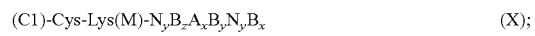

Formula (XI):

M-Cys-(Lys/His)$_y$-N$_y$B$_z$A$_x$B$_y$N$_y$B$_x$ (XI);

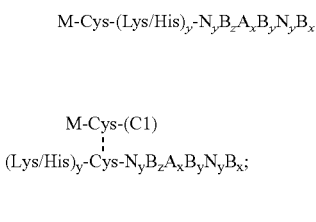 (XII)

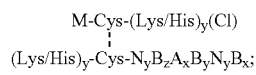 (XIII)

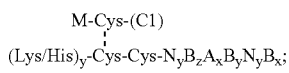 (XIV)

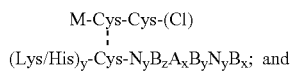 (XV)

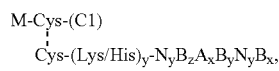 (XVI)

wherein:
--- represents a disulphide bond, and
C1, M, N, A, B, x, y and z are as defined for Formula (I) above.

In another embodiment of the present invention, the PKI compounds of Formula (I) have a formula selected from the group of:

BABBJ(M)BNB (XVI);
BABBJ(M)NBN (XVIII);
BNBBNJ(M)BAN (XIX);
ABBJABN (XX);
BNBBNJMNNNN (XXI);
BNBBNJ(M)NNN (XXII);
NBBNJ(M)NN (XXIII);
ABBJ(M)ABN (XXIV);
J(M)NBABB (XXV);
BNBBJ(M)NB (XXVI);
BNBBNJ(M)NNN (XXVII);
BABBNJ(M)NNA (XXVIII);
ABBJ(M)NN (XXIX);
BABBNJ(M)NNB (XXX);

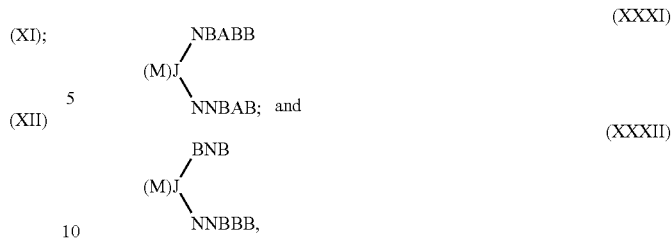

wherein:
M, J, N, A and B are as defined for Formula (I) above.

In another embodiment of the present invention, the PKI compounds of Formula (I) comprise between about 5 and about 18 amino acid residues. In a further embodiment, the PKI compounds of Formula (I) comprise between about 5 and about 16 amino acid residues. In another embodiment, the PKI compounds of Formula (I) comprise between about 6 and about 20 amino acid residues. In another embodiment, the PKI compounds of Formula (I) comprise between about 6 and about 18 amino acid residues. In another embodiment, the PKI compounds of Formula (I) comprise between about 7 and about 20 amino acid residues. In another embodiment, the PKI compounds of Formula (I) comprise between about 7 and about 18 amino acid residues.

In another embodiment of the present invention, the PKI compounds of Formula (I) comprise one or more of the amino acid sequences set forth in Table 2.

TABLE 2

| Representative Amino Acid Sequences | |
|---|---|
| Amino Acid Sequence | SEQ ID NO. |
| LRRAKLG | 1 |
| FRRKFRL | 2 |
| HCIGRFK | 3 |
| GCKGKFKR | 4 |
| KFRRKRGR | 5 |
| KFRRKLRL | 6 |
| KLRRAKRFL | 7 |
| FRRCFRL | 8 |
| KLRRAKLGLG | 9 |
| KLKKAKLGL | 10 |
| GCKGKFKR | 11 |
| KAKKKKAK | 12 |
| KLKKLKLVI | 13 |
| RFRKAKKGGH | 14 |
| FRRKLI | 15 |
| KFRKAKKGLK | 16 |
| GCRGR | 17 |
| KKCGGKKK | 18 |
| KFRRKRGREVD | 19 |

TABLE 2-continued

Representative Amino Acid Sequences

| Amino Acid Sequence | SEQ ID NO. |
|---|---|
| KFRRKLRLEVD | 20 |
| KLRRAKRFLEVD | 21 |
| KLRRAKLGLGDD | 22 |
| KAKKKKAKEGE | 23 |
| RFRKAKKGGHEIE | 24 |
| KFRKAKKGLKEVEK | 25 |
| GCRGREVD | 26 |

Compounds of the present invention include, but are not limited to, the following exemplary compounds:

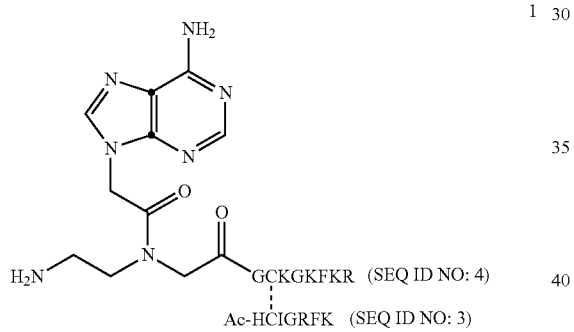

Ac-HCIGRFK (SEQ ID NO: 3) / GCKGKFKR (SEQ ID NO: 4)

1

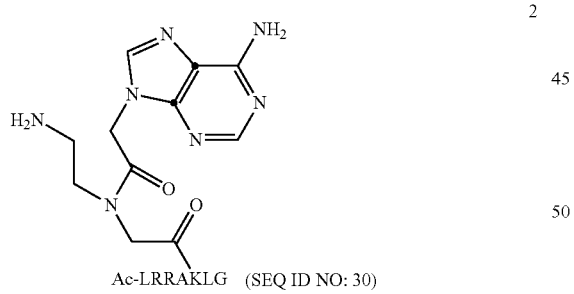

Ac-LRRAKLG (SEQ ID NO: 30)

2

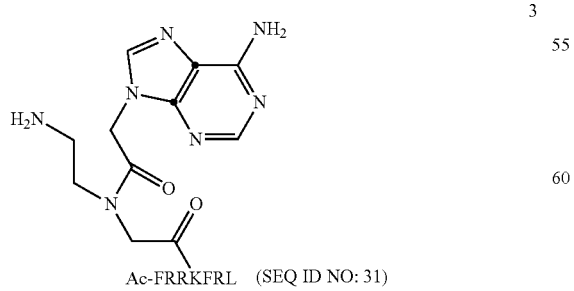

Ac-FRRKFRL (SEQ ID NO: 31)

3

Ac-FRRCFRL (SEQ ID NO: 32)

4

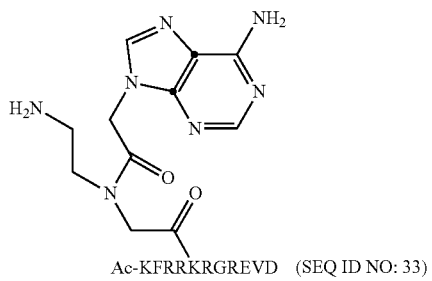

Ac-KFRRKRGREVD (SEQ ID NO: 33)

5

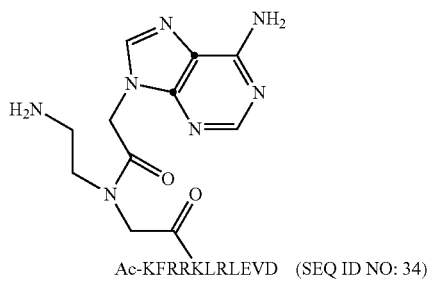

Ac-KFRRKLRLEVD (SEQ ID NO: 34)

6

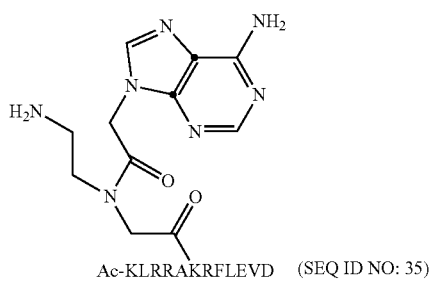

Ac-KLRRAKRFLEVD (SEQ ID NO: 35)

7

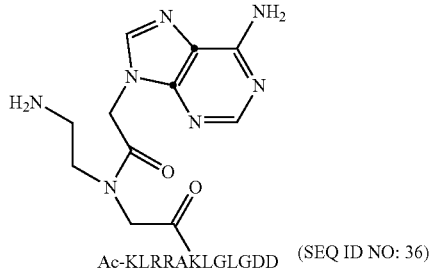

Ac-KLRRAKLGLGDD (SEQ ID NO: 36)

8

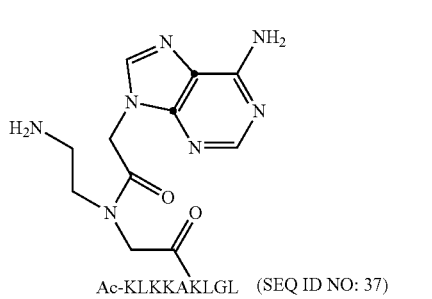

Ac-KLKKAKLGL (SEQ ID NO: 37)

9

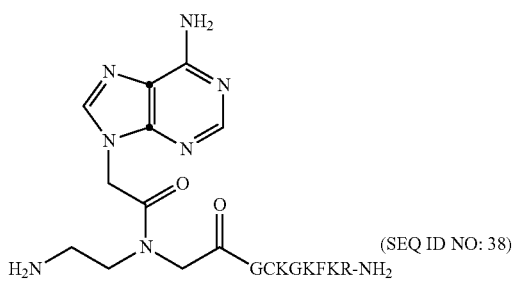
(SEQ ID NO: 38)

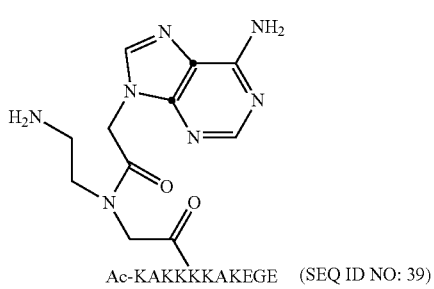
Ac-KAKKKKAKEGE (SEQ ID NO: 39)

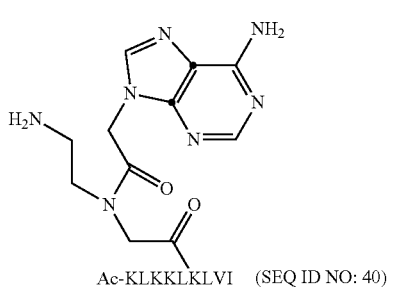
Ac-KLKKLKLVI (SEQ ID NO: 40)

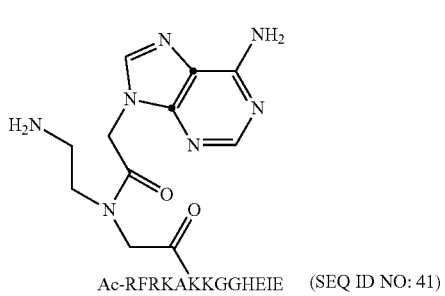
Ac-RFRKAKKGGHEIE (SEQ ID NO: 41)

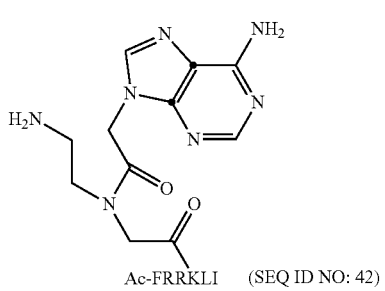
Ac-FRRKLI (SEQ ID NO: 42)

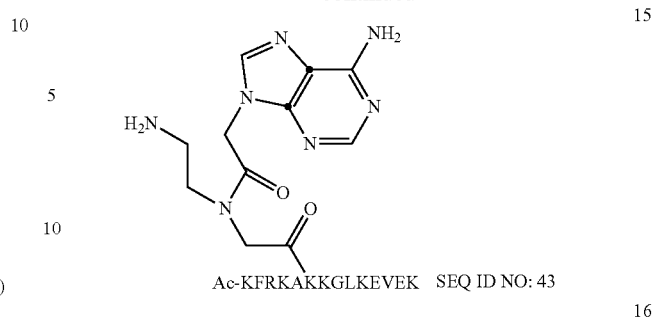
Ac-KFRKAKKGLKEVEK  SEQ ID NO: 43

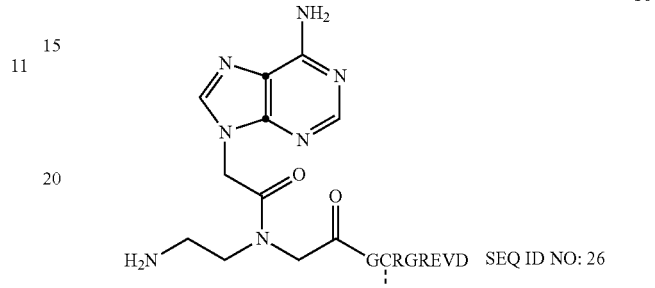
GCRGREVD  SEQ ID NO: 26
Ac-KKCGGKKK  SEQ ID NO: 18

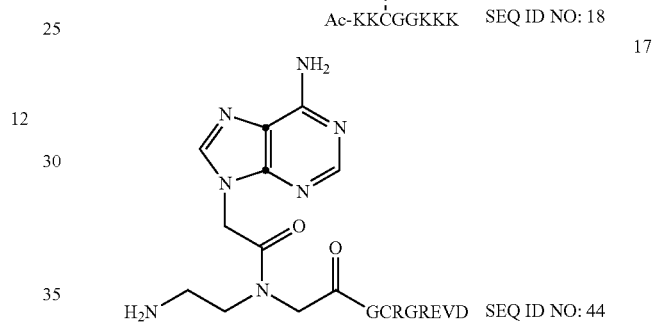
GCRGREVD  SEQ ID NO: 44

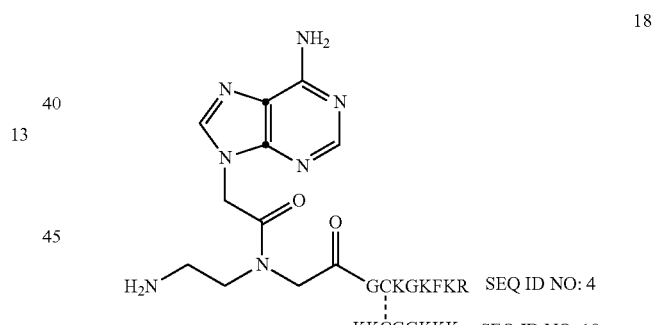
GCKGKFKR  SEQ ID NO: 4
KKCGGKKK  SEQ ID NO: 18

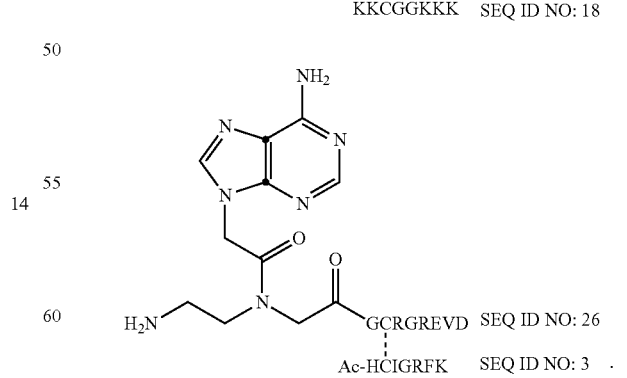
GCRGREVD  SEQ ID NO: 26
Ac-HCIGRFK  SEQ ID NO: 3 .

Peptidic Moiety

As depicted above in general Formula (I), the peptidic moiety comprised by the PKI compounds of the present invention can be in the form of a single amino acid chain, or in the form of two cross-linked amino acid chains. In the context of the present invention, an "amino acid chain" is a sequence of amino acid residues linked together by peptide bonds.

The term "amino acid residue," as used herein, encompasses both naturally-occurring amino acids and non-naturally-occurring amino acids. Examples of non-naturally occurring amino acids include, but are not limited to, D-amino acids (i.e. an amino acid of an opposite chirality to the naturally-occurring form), N-α-methyl amino acids, C-α-methyl amino acids, β-methyl amino acids and D- or L-β-amino acids. Other non-naturally occurring amino acids include, for example, β-alanine (β-Ala), norleucine (Nle), norvaline (Nva), homoarginine (Har), 4-aminobutyric acid (γ-Abu), 2-aminoisobutyric acid (Aib), 6-aminohexanoic acid (ε-Ahx), ornithine (orn), sarcosine, α-amino isobutyric acid, 3-aminopropionic acid, 2,3-diaminopropionic acid (2,3-diaP), D- or L-phenylglycine, D-(trifluoromethyl)-phenylalanine, and D-p-fluorophenylalanine.

The peptidic moiety can comprise one, or more than one, non-naturally occurring amino acids. When the peptidic moiety comprises more than one non-naturally occurring amino acids, the non-naturally occurring amino acids can be the same or different.

The peptidic moiety can comprise a free amino-terminus and/or carboxy-terminus, or a modified amino- and/or carboxy-terminus. For example, the N- and/or C-terminus of the peptidic moiety can be modified to include a chemical substituent group or other chemical modification, a blocking group or additional amino acids. Examples of chemical substituent groups suitable for modifying the amino- and/or carboxy-terminus of peptides are known in the art and include, but are not limited to, alkyl, alkenyl, alkynyl, amino, aryl, aralkyl, heteroalkyl, hydroxy, alkoxy, aralkyloxy, aryloxy, carboxy, acyl, aroyl, halo, nitro, alkoxycarbonyl, aryloxycarbonyl, aralkoxycarbonyl, acylamino, aroylamino, dialkylamino, carbamoyl, alkylcarbamoyl, dialkylcarbamoyl, alkylthio, aralkylthio, arylthio, alkylene, and $NZ_1Z_2$ where $Z_1$ and $Z_2$ are independently hydrogen, alkyl, aryl, or aralkyl, and the like. Blocking groups such as Fmoc (fluorenylmethyl-O—CO—), carbobenzoxy (benzyl-O—CO—), monomethoxysuccinyl, naphthyl-NH—CO—, acetylamino-caproyl and adamantyl-NH—CO—, can also be used. Other modifications contemplated by the present invention include C-terminal hydroxymethyl modifications, O-modifications (for example, C-terminal hydroxymethyl benzyl ether) and N-terminal modifications such as substituted amides, for example alkylamides and hydrazides.

The presence of extra amino acids to one of the termini of the peptides may be desirable, for example, to improve the stability of the peptides, to incorporate a "tag" to aid in identification, detection or purification protocols, to improve solubility or to improve pharmokinetic parameters. As noted above, in one embodiment of the present invention, the peptidic moiety is modified at the C-terminus to include a "tag" of between 1 to 4 amino acids in length that comprises one or more acidic amino acid residues. Addition of one or more acidic residues at the C-terminus of the PKI compound can help to improve the interaction of the compound with the target protein kinase. Non-acidic residues included in the tag are selected from the group of: Gly, Val, Ile, Leu and Lys. Examples of suitable tags that can be added at the C-terminal end include, but are not limited to Glu-Val-Glu, Asp-Asp, Glu-Gly-Glu, Glu-Ile-Glu, Glu-Val-Glu-Lys (SEQ ID NO:47), and Glu-Val-Asp.

In one embodiment of the present invention, the N-terminus of the peptidic moiety is modified with an acyl group. In another embodiment, the N-terminus is modified with an acetyl group. In another embodiment, the C-terminus is modified with an amino group.

In the context of the present invention, a "peptide bond" which links the amino acid residues of the peptidic moiety can be a naturally-occurring peptide bond or a non-naturally occurring peptide bond. Examples of suitable modified peptide bonds are well known in the art and include, but are not limited to, —$CH_2NH$—, —$CH_2S$—, —$CH_2CH_2$—, —$CH=CH$— (cis or trans), —$COCH_2$—, —$CH(OH)CH_2$—, $CH_2SO$—, —$CS$—$NH$— and —$NH$—$CO$— (i.e. a reversed peptide bond) (see, for example, Spatola, Vega Data Vol. 1, Issue 3, (1983); Spatola, in *Chemistry and Biochemistry of Amino Acids Peptides and Proteins*, Weinstein, ed., Marcel Dekker, New York, p. 267 (1983); Morley, J. S., *Trends Pharm. Sci.* pp. 463-468 (1980); Hudson et al., *Int. J. Pept. Prot. Res.* 14:177-185 (1979): Spatola et al., *Life Sci.* 38:1243-1249 (1986); Hann, *J. Chem. Soc. Perkin Trans. I* 307-314 (1982); Almquist et al., *J. Med. Chem.* 23:1392-1398 (1980); Jennings-White et al., *Tetrahedron Lett.* 23:2533 (1982); Szelke et al, EP 45665 (1982); Holladay et al., *Tetrahedron Lett.* 24:4401-4404 (1983); and Hruby, *Life Sci.* 31:189-199 (1982)). The peptidic moiety can comprise one, or more than one, non-naturally occurring peptide bonds. When the peptidic moiety comprises more than one non-naturally occurring peptide bonds, the non-naturally occurring peptide bonds can be the same or different.

As indicated above, the peptidic moiety can comprise a disulphide bond between two cysteine residues. The present invention also contemplates the use of a suitable chemical groups to cross-link two peptide chains comprised by a PKI compound of Formula (I). Examples of such chemical groups are well known in the art.

ATP Mimetic Moiety

As indicated above, in one embodiment of the present invention, the PKI compounds comprise an ATP mimetic moiety which includes adenine, or a derivative of adenine. A "derivative of adenine," as used herein, refers to a compound that retains the heteroaromatic ring structure of adenine (20; as shown below) but which may contain additional, fewer or different substituents attached to the ring structure and/or additional, fewer or different heteroatoms within the ring structure when compared to adenine.

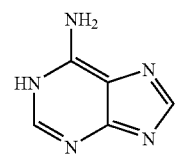

20

The term "derivative of adenine" also encompasses molecules that are isosteric with adenine. In the context of the present invention, a molecule that is isosteric with adenine (an "adenine isostere") is a molecule that has a similarity of structure and spatial orientation to adenine and a resulting similarity of properties, in particular with respect to three-dimensional space-filling properties.

Suitable adenine derivatives are known in the art and include, but are not limited to, 1-deazaadenine; 3-deazaadenine; 7-deazaadenine; 7-deaza-8-azaadenine; 1-methyladenine; 2-aminoadenine; 2-propyl and other 2-alkyl derivatives of adenine; 2-aminopropyladenine; 8-amino, 8-aza, 8-thiol, 8-thioalkyl, 8-hydroxyl and other 8-substituted adenines; 8-oxo-$N^6$-methyladenine; $N^6$-methyladenine; $N^6$-isopentenyladenine; 2-aminopurine; 2,6-diaminopurine; 2-amino-6-chloropurine; 6-thio-2-aminopurine; hypoxanthine; inosine; xanthine; 8-aza derivatives of 2-aminopurine, 2,6-diaminopurine, 2-amino-6-chloropurine, hypoxanthine, inosine and xanthine; 7-deaza-8-aza derivatives of 2-aminopurine, 2,6-diaminopurine, 2-amino-6-chloropurine, hypoxanthine, inosine and xanthine; 1-deaza derivatives of 2-aminopurine, 2,6-diaminopurine, 2-amino-6-chloropurine, hypoxanthine, inosine and xanthine; 7-deaza derivatives of 2-aminopurine, 2,6-diaminopurine, 2-amino-6-chloropurine, hypoxanthine, inosine and xanthine; and 3-deaza derivatives of 2-aminopurine, 2,6-diaminopurine, 2-amino-6-chloropurine, hypoxanthine, inosine and xanthine; and adenine isosteres, such as 4-methylindole.

In accordance with one embodiment of the present invention, the ATP mimetic moiety is an adenine peptide nucleic acid (PNA) of the general Formula (XXXIII):

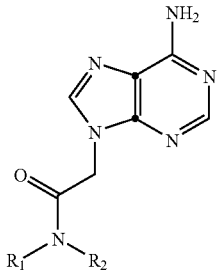

(XXXIII)

wherein:
$R_1$ and $R_2$ are independently alkyl substituted with a carboxyl, carbonyl, alcohol or primary amino (i.e. —COOH, —C(O)R, where R is alkyl or H, —OH or —NH$_2$).

In one embodiment of the present invention, in Formula (XXXIII), $R_1$ is —CH$_2$CH$_2$NH$_2$; and $R_2$ is —CH$_2$COOH.

In the PKI compounds of Formula (I), the ATP moiety (M) when present can be linked to the peptidic moiety using a number of standard linking groups known in the art. In one embodiment of the present invention, the ATP mimetic moiety is attached to the peptidic moiety via a linking group attached to a nitrogen atom in the heteroaromatic ring structure. Attachment through a substituent amino group, such as $N^6$ of adenine, is also contemplated.

In accordance with one embodiment of the present invention, in which the ATP mimetic moiety is provided as an adenine peptide nucleic acid (PNA) of general Formula (XXXIII), this moiety can be linked to the peptidic moiety by formation of a peptide bond with a N-terminal NH$_2$ group or a C-terminal CO$_2$H group of the peptidic moiety, or with an amine group in the side chain of a lysine or arginine residue in the peptidic moiety.

In one embodiment of the present invention, the PKI compounds comprise an adenine PNA of general Formula (XXXIII) as the ATP mimetic moiety, which is attached to the peptidic moiety by a peptide bond to a N-terminal NH$_2$ group. In another embodiment, the adenine PNA of general Formula (XXXIII) is attached to the peptidic moiety by a peptide bond to an amine group in the side chain of a lysine residue.

Preparation of the PKI Compounds

The peptidic moiety of the PKI compounds can be synthesized by conventional peptide chemistry techniques. The principles of solid phase chemical synthesis of peptides are well known in the art and can be found in a number of general texts such as Pennington, M. W. and Dunn, B. M., *Methods in Molecular Biology*, Vol. 35 (Humana Press, 1994); Dugas, H. and Penney, C., *Bioorganic Chemistry* (1981) Springer-Verlag, New York, pgs. 54-92; Merrifield, J. M., *J. Chem. Soc.*, 85:2149 (1962), and Stewart and Young, *Solid Phase Peptide Synthesis*, pp. 24-66, Freeman (San Francisco, 1969).

Covalent modifications of the peptide can be introduced, for example, by reacting targeted amino acid residues with an organic derivatising agent that is capable of reacting with selected side chains or terminal residues as is known in the art. Selection of appropriate derivatising agent(s) can be readily accomplished by a skilled technician.

The various ATP mimetic moieties contemplated by the present invention can be obtained commercially or can be synthesized from commercially available starting materials using standard synthetic organic chemistry techniques.

For PKI compounds of Formula (I) that comprise an ATP mimetic moiety, the ATP mimetic moiety can be attached to the peptidic moiety at the appropriate position using standard techniques. The final PKI compound can be purified using one or more standard purification techniques if necessary prior to use.

Exemplary methods of preparing the inhibitors in one embodiment of the invention are provided in the Examples.

Testing the PKI Compounds

A. Inhibition of Protein Kinase Activity

The PKI compounds of the present invention are capable of inhibiting one or more protein kinases. Accordingly, the activity of candidate PKI compounds can be tested using standard in vitro assays. Assays to determine protein kinase activity are well known in the art, see for example, *Current Protocols in Pharmacology* (Enna & Williams, Ed., J. Wiley & Sons, New York, N.Y.).

In general, the ability of a candidate compound to inhibit the activity of a selected protein kinase is assessed by adding the candidate compound to a reaction mixture comprising the target protein kinase in an appropriate buffer, together with a substrate, ATP, and any necessary co-factors (such as Mn$^{2+}$ and/or Ca$^{2+}$). After a suitable incubation time, the extent of phosphorylation of the substrate is monitored and compared to a control reaction, for example, a reaction conducted in the absence of the candidate compound, or in the presence of a known PK inhibitor. The substrate used in the assay is a protein or a peptide that is capable of being phosphorylated by the particular protein kinase being investigated. In most assays, peptide substrates are used.

The extent of substrate phosphorylation can be determined by a number of methods known in the art, for example, traditional methods employ radiolabelled ATP in the assay and determine the amount of radioactivity incorporated into the phosphorylated substrate at the end of the incubation period.

Alternative methods known in the art include those that employ a suitably labelled monoclonal antibody, which specifically binds to the phosphorylated form of the substrate. The antibody is added to the reaction mixture during or at the end of the incubation period and the amount of bound antibody is measured as an indication of the amount of substrate phosphorylation that has taken place. Other methods include the use of fluorescently labelled substrates (see, for example, PepTag® Non-Radioactive Assays, Promega, Madison, Wis.), fluorescently labelled substrates together with a quencher molecule (for example, the IQ® Assays from Pierce Biotechnology Inc., Rockford, Ill.) and luminescent detection of unreacted ATP (for example, the Kinase-Glo™ Luminescent Kinase Assays from Promega, Madison, Wis.). Methods based on fluorescence polarisation techniques that include the addition, at the end of the incubation period, of a fluorescently labelled tracer molecule and an antibody capable of binding the phosphorylated substrate and the tracer molecule (see PanVera® PolarScreen™ kits from Invitrogen, Carlsbad, Calif.).

In vitro assays such as those outlined above can be performed as high-throughput assays, which allows a number of different candidate inhibitors to be screened simultaneously against a particular protein kinase. High-throughput assays also allow a particular PKI compound to be screened for activity against a panel of different protein kinases. Many commercially available protein kinase assay kits are specifically designed to permit high-throughput screening (for example, the IQ® assays, Kinase-Glo™ assays and PanVera® PolarSreen™ kits referred to above, and the Multiscreen®$_{HTS}$-PH Phosphocellulose Filter Plate Assays from Millipore, Billerica, Mass.).

The protein kinase employed in the in vitro assays can be in the form of a purified enzyme, a semi-purified enzyme, or it can be present in a partially purified or crude cell lysate prepared from a cell line or tissue of interest. A number of protein kinases are commercially available in pure or partially pure form (for example, from Sigma-Aldrich, St Louis, Mo.; Pierce Biotechnology Inc., Rockford, Ill.; and Promega Madison, Wis.).

The PKI compounds of the present invention can also be assessed for their ability to inhibit one or more protein kinases in a cellular context if desired by contacting a cell line of interest with the PKI compound and subsequently assessing protein kinase activity in a cell lysate prepared from the cells using standard methods, such as those described above. Alternatively, a selected cell line maintained under appropriate growth conditions can be treated with a candidate compound and the extent of phosphorylation of a naturally-occurring substrate molecule present within the cells can be assessed and compared to untreated control cells, or cells treated with a known inhibitor of the target protein kinase. For example, candidate compounds can be assessed for their ability to inhibit PKB activity by determining the amount of phospho-GSK-3 present in cells treated with the compound using commercially available antibodies against phospho-GSK3α (Cell Signaling Technology, Beverly, Mass.).

Other examples of assays for screening the compounds for their ability of inhibit PKs are described in the Examples provided herein.

B. In Vitro Physiological Activity

The PKI compounds of the present invention can be assessed for their ability to inhibit one or more protein kinase mediated physiological effects either in vitro or in vivo, if desired. Examples of such physiological effects include cell proliferation, cell invasion/migration, cell differentiation, cell morphology, cell survival or apoptosis, cell response to external stimuli, gene expression, lipid metabolism, glycogen metabolism and mitosis.

In general, the ability of a candidate PKI compound to inhibit a protein kinase mediated physiological effect can be assessed by contacting cells in which the physiological effect is manifested with the candidate compound and incubating the cells under conditions suitable for assessing the physiological effect. The extent of inhibition of the physiological effect can be determined by comparison of the test cells with a suitable control, for example, untreated cells incubated under the same conditions, or cells incubated under the same conditions in the presence of a known PK inhibitor.

For example, cell proliferation can be assessed by comparing the number of cells present a given period of time after treatment with a PKI compound with the number of cells originally present. Cell migration/invasion can be assessed by standard cell migration assays in which the ability of the PKI compound to inhibit the migration of cells through a membrane coated with a suitable compound, such as collagen, gelatine or Matrigel, in response to a chemoattractant is measured. Cell differentiation can be assessed by determining the degree of differentiation in the cells a given period of time after treatment with a PKI compound and comparing this to the degree of differentiation in control cells; and metabolic activity of cells such as primary adipocytes, hepatocytes and fibroblasts, can be assessed by measuring glucose uptake, lipogenesis, or glycogen metabolism (see, for example, Weise et al., *J Biol. Chem.* 270:3442 (1995)). Gene expression, cell morphology or cellular phenotype can also be assessed using standard techniques as an indication of a protein kinase mediated physiological effect inhibited by the candidate compound.

In accordance with one embodiment of the present invention, the PKI compounds inhibit cellular proliferation. Methods of assessing the ability of a candidate compound to inhibit cellular proliferation are well known in the art. In general, for in vitro assays, cells of a specific test cell line are grown to an appropriate density (e.g. approximately $1\times10^4$) and the candidate compound is added. After an appropriate incubation time (for example, 48 to 74 hours), cell density is assessed. Methods of measuring cell density are known in the art, for example, the cell density can be assessed under a light inverted microscope by measuring the surface of the culture plate covered by the cell monolayer; or by using the resazurin reduction test (see Fields & Lancaster (1993) *Am. Biotechnol. Lab.* 11:48-50; O'Brien et al., (2000) *Eur. J. Biochem.* 267: 5421-5426 and U.S. Pat. No. 5,501,959), the sulforhodamine assay (Rubinstein et al., (1990) *J. Natl. Cancer Inst.* 82:113-118) or the neutral red dye test (Kitano et al., (1991) *Euro. J. Clin. Investig.* 21:53-58; West et al, (1992) *J. Investigative Derm.* 99:95-100). Alternatively, the cells can be detached from the plate, for example, by incubation with trypsin and then counted in an hemocytometer. Percent inhibition of proliferation of the cells can be calculated by comparison of the cell density in the treated culture with the cell density in control cultures, for example, cultures not pre-treated with the candidate compound and/or those pre-treated with a control compound known to inhibit cell proliferation. Cells may be treated with a mitogen prior to addition of the candidate compound to assess the ability of the compounds to inhibit proliferation of stimulated cells as opposed to unstimulated, or quiescent cells. The use of mitogen-stimulated cells can be useful, for example, in assessing the ability of the candidate compound to inhibit proliferation of endothelial cells.

DNA synthesis can be also assessed as an indication of cell proliferation. For example, by the uptake of [$^3$H]thymidine. Typically cells are grown to an appropriate density (generally to confluence) at which point the growth medium is replaced with a medium that renders the cells quiescent (for example, DME 0.5% serum). The quiescent cells are exposed to a mitogenic stimulus, such as diluted serum or a growth factor, at a suitable interval after the medium replacement. [$^3$H] thymidine is subsequently added to the cells, and the cells are maintained at 37° C. After an appropriate incubation time, the cells are washed, the acid-precipitable radioactivity is extracted and the amount of radioactivity determined, for example, by using a scintillation counter. Measurement of the total DNA, which relates to the number of cells, can also be used to determine the effect of the PKI compounds on cell proliferation. An exemplary protocol is provided in the Examples herein.

A variety of readily available cell-lines can be utilised in the in vitro assays described above, including endothelial cells, cancer cells and keratinocytes. Non-limiting examples of suitable endothelial cell lines include human umbilical vein endothelial cells (HUVECs), bovine aortic endothelial cells (BAECs), human coronary artery endothelial cells (HCAECs), bovine adrenal gland capillary endothelial cells (BCE) and vascular smooth muscle cells. Exemplary cancer cell lines include, but are not limited to, mesothelial cell lines MSTO-211H, NCI-H2052 and NCI-H28, ovarian cancer cell-lines OV90 and SK-OV-3, breast cancer cell-lines MCF-7 and MDA-MB-231, colon cancer cell-lines CaCo2, HCT116 and HT29, cervical cancer cell-line HeLa, non-small cell lung carcinoma cell-lines A549 and H1299, pancreatic cancer cell-lines MIA-PaCa-2 and AsPC-1, prostate cancer-cell line PC-3, bladder cancer cell-line T24, liver cancer cell-line HepG2, brain cancer cell-line U-87 MG, melanoma cell-line A2058, and lung cancer cell-line NCI-H460. Other examples of suitable cell lines include human keratinocytes (such as HaCaT cells); rheumatoid synovial fibroblasts (RSFs), and Jurkat T cells. Other suitable cell-lines are known in the art and many are commercially available (for example, from the American Type Culture Collection, Manassas, Va.).

C. In Vivo Physiological Activity

The ability of the PKI compounds of the invention to inhibit one or more protein kinase mediated physiological effects can be tested in vivo using an appropriate animal model known in the art (see, for example, *Current Protocols in Pharmacology*, Enna & Williams, Ed., J. Wiley & Sons, New York, N.Y.).

For example, the effect of the compounds on ocular diseases such as diabetic retinopathy and macular degeneration can be assessed using a newborn rat model of the retinopathy of prematurity (see, for example, Niesman, M. et al. (1997) *Neurochem. Res.* 22:597) and a mouse model of macular degeneration (see, for example, Isaji et al., (1997) *Brit. J. Pharmacol.* 122:1061). The effect of the compounds on ischemia can be assessed, for example, ex vivo using Langendorff-perfused rat heart (see, for example, Yao, et al, (1994) *Biol. Pharm. Bull* 17:517) or in vivo using rat or dog models of myocardial ischemia/reperfusion injury. The anti-atherosclerotic effect can be assessed, for example, in spontaneously hypertensive rats (see, for example, Kubo, et al., (1992) *J. Pharmacobiodyn.* 15:657). A variety of animal models are known in the art to test the anti-inflammatory activity of test compounds, for example, carrageenan-induced paw oedema, adjuvant-induced arthritis and carrageenan air pouch rat models (see *Current Protocols in Pharmacology*, Enna & Williams, Ed., J. Wiley & Sons, New York, N.Y.), and rat models of psoriasis (see, for example, Smith, S., et al. (1993) *Immunopharmacol. Immunotoxicol.* 15:13).

For assessing the ability of the PKI compounds to inhibit tumour growth or proliferation in vivo, standard animal models can be used, for example, xenograft models, in which a human tumour has been implanted into an animal. Examples of xenograft models of human cancer include, but are not limited to, human solid tumour xenografts, implanted by sub-cutaneous injection or implantation and used in tumour growth assays; human solid tumour isografts, implanted by fat pad injection and used in tumour growth assays; human solid tumour orthotopic xenografts, implanted directly into the relevant tissue and used in tumour growth assays; experimental models of lymphoma and leukaemia in mice, used in survival assays, and experimental models of lung metastasis in mice. In addition to the implanted human tumour cells, the xenograft models can further comprise transplanted human peripheral blood leukocytes, which allow for evaluation of the anti-cancer immune response.

Alternatively, murine cancer models can be used for screening anti-tumour compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models.

For example, the PKI compounds can be tested in vivo on solid tumours using mice that are subcutaneously grafted bilaterally with 30 to 60 mg of a tumour fragment, or implanted with an appropriate number of cancer cells, on day 0. The animals bearing tumours are mixed before being subjected to the various treatments and controls. In the case of treatment of advanced tumours, tumours are allowed to develop to the desired size, animals having insufficiently developed tumours being eliminated. The selected animals are distributed at random to undergo the treatments and controls. Animals not bearing tumours may also be subjected to the same treatments as the tumour-bearing animals in order to be able to dissociate the toxic effect from the specific effect on the tumour. Chemotherapy generally begins from 3 to 22 days after grafting, depending on the type of tumour, and the animals are observed every day. The PKI compounds of the present invention can be administered to the animals, for example, by intraperitoneal (i.p.) injection or bolus infusion.

The tumours are measured after a pre-determined time period, or they can be monitored continuously by measuring about 2 or 3 times a week until the tumour reaches a pre-determined size and/or weight, or until the animal dies if this occurs before the tumour reaches the pre-determined size/weight. The animals are then sacrificed and the tissue histology, size and/or proliferation of the tumour assessed.

For the study of the effect of the PKI compounds on leukaemias, the animals are grafted with a particular number of cells, and the anti-tumour activity is determined by the increase in the survival time of the treated mice relative to the controls.

To study the effect of the PKI compounds on tumour metastasis, tumour cells are typically treated with the composition ex vivo and then injected into a suitable test animal. The spread of the tumour cells from the site of injection is then monitored over a suitable period of time.

Suitable cancer cell lines for in vivo testing of the compounds are known in the art and include those listed above. Many suitable cancer cell-lines are commercially available (for example, from the American Type Culture Collection, Manassas, Va.).

In vivo toxic effects of the PKI compounds can be evaluated by measuring their effect on animal body weight during treatment and by performing haematological profiles and liver enzyme analysis after the animal has been sacrificed.

Pharmaceutical Compositions

The present invention provides for pharmaceutical compositions comprising one or more of the PKI compounds of the invention and one or more non-toxic pharmaceutically acceptable carriers, diluents, excipients and/or adjuvants. If desired, other active ingredients may be included in the compositions. As indicated below, such compositions are useful in the treatment of various protein kinase mediated conditions in animals, including humans.

The pharmaceutical compositions may comprise from about 1% to about 95% of a PKI compound of the invention.

Compositions formulated for administration in a single dose form may comprise, for example, about 20% to about 90% of the PKI compound, whereas compositions that are not in a single dose form may comprise, for example, from about 5% to about 20% of the PKI compound. Non-limiting examples of unit dose forms include dragées, tablets, ampoules, vials, suppositories and capsules.

The pharmaceutical compositions can be formulated for administration by a variety of routes. For example, the compositions can be formulated for oral, topical, rectal or parenteral administration or for administration by inhalation or spray. The term "parenteral" as used herein includes subcutaneous, intravenous, intramuscular, intrathecal, intrasternal injection, implants, or infusion techniques.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavouring agents, colouring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatine or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monosterate or glyceryl distearate may be employed.

Pharmaceutical compositions for oral use can also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium such as peanut oil, liquid paraffin or olive oil.

Pharmaceutical compositions formulated as aqueous suspensions contain the PKI compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia: dispersing or wetting agents such as a naturally-occurring phosphatide, for example, lecithin, or condensation products of an alkylene oxide with fatty acids, for example, polyoxyethylene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, one or more colouring agents, one or more flavouring agents or one or more sweetening agents, such as sucrose or saccharin.

Pharmaceutical compositions can be formulated as oily suspensions by suspending the PKI compound(s) in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and/or flavouring agents may be added to provide palatable oral preparations. These compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the PKI compound(s) in admixture with one or more dispersing or wetting agents, suspending agents and/or preservatives. Suitable dispersing or wetting agents and suspending agents are exemplified by those already mentioned above. Additional excipients, for example, sweetening, flavouring and colouring agents, can also be included in these compositions.

Pharmaceutical compositions of the invention can also be formulated as oil-in-water emulsions. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soybean, lecithin; or esters or partial esters derived from fatty acids and hexitol, anhydrides, for example, sorbitan monoleate, and condensation products of the said partial esters with ethylene oxide, for example, polyoxyethylene sorbitan monoleate. The emulsions can also optionally contain sweetening and flavouring agents.

Pharmaceutical compositions can be formulated as a syrup or elixir by combining the PKI compound(s) with one or more sweetening agents, for example glycerol, propylene glycol, sorbitol or sucrose. Such formulations can also optionally contain one or more demulcents, preservatives, flavouring agents and/or colouring agents.

The pharmaceutical compositions can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Other pharmaceutical compositions and methods of preparing pharmaceutical compositions are known in the art and are described, for example, in "*Remington: The Science and Practice of Pharmacy*" (formerly "*Remingtons Pharmaceutical Sciences*"); Gennaro, A., Lippincott, Williams & Wilkins, Philidelphia, Pa. (2000).

The one or more PKI compounds of the invention are included in the pharmaceutical compositions in an amount effective to achieve the intended purpose. Thus the term "therapeutically effective dose" refers to the amount of the PKI compound that improves the status of the subject to be treated, for example, by ameliorating the symptoms of the disease or disorder to be treated, preventing the disease or disorder, or altering the pathology of the disease. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans using standard methods known in those of ordinary skill in the art.

Therapeutic efficacy and toxicity can also be determined by standard pharmaceutical procedures such as, for example, by determination of the median effective dose, or $ED_{50}$ (i.e. the dose therapeutically effective in 50% of the population) and the median lethal dose, or $LD_{50}$ (i.e. the dose lethal to 50% of the population). The dose ratio between therapeutic and toxic effects is known as the "therapeutic index," which can be expressed as the ratio, $LD_{50}/ED_{50}$. The data obtained from cell culture assays and animal studies can be used to formulate a range of dosage for human or animal use. The dosage contained in such compositions is usually within a range of concentrations that include the $ED_{50}$ and demonstrate little or no toxicity. The dosage varies within this range depending upon the dosage form employed, sensitivity of the subject, and the route of administration and the like.

The exact dosage to be administered to a subject can be determined by the practitioner, in light of factors related to the subject requiring treatment. Dosage and administration are adjusted to provide sufficient levels of the PKI compound and/or to maintain the desired effect. Factors which may be taken into account when determining an appropriate dosage include the severity of the disease state, general health of the subject, age, weight, and gender of the subject, diet, time and frequency of administration, drug combination(s), reaction sensitivities, and tolerance/response to therapy. Dosing regimens can be designed by the practitioner depending on the above factors as well as factors such as the half-life and clearance rate of the particular formulation.

Exemplary daily doses for the PKI compounds of the invention range from about 0.0001 to about 100 mg per kilogram of body weight per day, for example, from about 0.001 to about 10 mg per kilogram, or from about 0.01 to about 1 mg per kilogram. The daily dose can be administered as a single dose or it can be divided into two, three, four, five, six or more sub-doses for separate administration at appropriate intervals throughout the day, optionally, in unit dosage forms.

Use of the PKI Compounds

The present invention provides for the use of the PKI compounds to inhibit the activity of one or more protein kinases in vitro or in vivo and for methods of inhibiting one or more protein kinases in a subject by administration of an effective amount of a PKI compound of the invention.

Protein kinases have been implicated in a variety of diseases and disorders. Accordingly, the present invention also contemplates the use of the PKI compounds, alone or in combination with other chemotherapeutic agents, in the treatment of protein kinase mediated diseases and disorders such as, cancer, psoriasis, angiogenesis, restenosis, atherosclerosis, cardiovascular disease (such as arrhythmia), hypertension, diabetes, neurological disorders, rheumatoid arthritis, kidney disorders (such as polycystic kidney), inflammatory disorders and autoimmune disorders.

One embodiment of the present invention provides for the use of the PKI compounds in the treatment of cancer. In this context, treatment with a PKI compound of the invention may result in a reduction in the size of a tumour, the slowing or prevention of an increase in the size of a tumour, an increase in the disease-free survival time between the disappearance or removal of a tumour and its reappearance, prevention of an initial or subsequent occurrence of a tumour (e.g. metastasis), an increase in the time to progression, reduction of one or more adverse symptom associated with a tumour, or an increase in the overall survival time of a subject having cancer.

The PKI compounds can be used to inhibit the growth and/or metastasis of a variety of tumours. Exemplary tumours include, but are not limited to, haematologic neoplasms, including leukaemias, myelomas and lymphomas; carcinomas, including adenocarcinomas and squamous cell carcinomas; melanomas and sarcomas. Carcinomas and sarcomas are also frequently referred to as "solid tumours." Examples of commonly occurring solid turnouts include, but are not limited to, cancer of the brain, breast, cervix, colon, head and neck, kidney, lung, ovary, pancreas, prostate, stomach and uterus, non-small cell lung cancer and colorectal cancer. Various forms of lymphoma also may result in the formation of a solid tumour and, therefore, are also often considered to be solid tumours.

Additional cancers encompassed by the present invention include, for example, multiple myeloma, neuroblastoma, rhabdomyosarcoma, primary thrombocytosis, primary macroglobulinemia, primary brain tumours, gliomas, mesothelioma and medulloblastoma.

One embodiment of the present invention provides for the use of the PKI compounds in the treatment of a solid tumour. In another embodiment, the present invention provides for the use of the PKI compounds in the treatment of a cancer of the central nervous system. In a further embodiment, the present invention provides for the use of the PKI compounds in the treatment of a neuroblastoma or glioma. In another embodiment, the present invention provides for the use of the PKI compounds in the treatment of a solid cancer selected from cancer of the brain, breast, cervix, colon, head and neck, kidney, lung, ovary, pancreas, prostate, stomach and uterus.

The cancer to be treated may be indolent or it may be aggressive. The present invention contemplates the use of the PKI compounds in the treatment of refractory cancers, advanced cancers, recurrent cancers and metastatic cancers.

"Aggressive cancer," as used herein, refers to a rapidly growing cancer. One skilled in the art will appreciate that for some cancers, such as breast cancer or prostate cancer the term "aggressive cancer" will refer to an advanced cancer that has relapsed within approximately the earlier two-thirds of the spectrum of relapse times for a given cancer, whereas for other types of cancer, such as small cell lung carcinoma (SCLC) nearly all cases present rapidly growing cancers which are considered to be aggressive. The term can thus cover a subsection of a certain cancer type or it may encompass all of another cancer type. A "refractory" cancer or tumour refers to a cancer or tumour that has not responded to treatment. "Advanced cancer," refers to overt disease in a patient, wherein such overt disease is not amenable to cure by local modalities of treatment, such as surgery or radiotherapy. Advanced disease may refer to a locally advanced cancer or it may refer to metastatic cancer. The term "metastatic cancer" refers to cancer that has spread from one part of the body to another. Advanced cancers may also be unresectable, that is, they have spread to surrounding tissue and cannot be surgically removed.

The PKI compounds can also be used to treat drug resistant cancers, including multidrug resistant (MDR) tumours. As is known in the art, the resistance of cancer cells to chemotherapy is one of the central problems in the management of cancer. Various protein kinases, including protein kinase C have been implicated in multidrug resistance of tumours. In one embodiment, therefore, the PKI compounds of the present invention can be used to increase the sensitivity of multidrug resistant tumours to known chemotherapeutics.

Certain cancers, such as prostate and breast cancers, can be treated by hormone therapy, i.e. with hormones or anti-hormone drugs that slow or stop the growth of certain cancers by blocking the body's natural hormones. Such cancers may develop resistance, or be intrinsically resistant, to hormone therapy. In another embodiment, the present invention contemplates the use of the PKI compounds in the treatment of such "hormone-resistant" or "hormone-refractory" cancers.

As noted above, the present invention also contemplates the use of the PKI compounds as "sensitizing agents." In this case, the compound alone does not have a cytotoxic effect on the cancer cells, but provides a means of weakening the cells, and thereby facilitates the benefit from conventional anti-cancer therapeutics.

The present invention further contemplates the use of the PKI compounds in other, non-therapeutic applications. For example, the PKI compounds can be utilised in assays relating to the development of other protein kinase antagonists or agonists. The PKI compounds are also useful tools in studies relating to the mechanism of action of protein kinases, as well as for the elucidation of mechanistic information relating to biological pathways in which various protein kinases are involved. Methods known in the art to determine biological pathways can be used to determine the pathway, or network of pathways affected by contacting cells with a PKI compound, for example, by analysing cellular constituents that are expressed or repressed after contact with the PKI compounds as compared to untreated, positive or negative control compounds, or analysing some other metabolic activity of the cell such as enzyme activity, nutrient uptake, or proliferation. Cellular components analysed can include gene transcripts, and protein expression. Suitable methods can include standard biochemistry techniques, radiolabelling the compounds of the invention (for example, with $^{14}$C or $^{3}$H), and observing the PKI compounds binding to protein kinases or other proteins (for example, using 2D gels), as well as gene expression profiling and the like.

The present invention also contemplates the use of the PKI compounds as part of an in vitro assay in order to determine whether a subject is likely to benefit from treatment with the compound in question and as fluorescent conjugates for the detection of micrometastases.

Kits

The present invention additionally provides for kits or packs containing one or more of the PKI compounds of the invention or a pharmaceutical composition comprising one or more PKI compounds. The kits and packs can be research kits for non-therapeutic use, diagnostic kits or pharmaceutical kits or packs for use in the treatment of protein kinase mediated diseases or disorders. Individual components of the kits can be packaged in separate containers, associated with which, when applicable, can be a notice in the form prescribed by a governmental agency regulating the manufacture, use or sale of pharmaceuticals or biological products, which notice reflects approval by the agency of manufacture, use or sale for human or animal administration. The kits may optionally contain instructions or directions outlining the method of use or dosing regimen for the PKI compounds. Pharmaceutical kits can optionally further contain one or more other therapeutic agents for use in combination with the PKI compounds of the invention.

When one or more components of the kit are provided as solutions, for example aqueous solutions, or sterile aqueous solutions, the container means may itself be an inhalant, syringe, pipette, eye dropper, or other such like apparatus, from which the solution may be administered, dispensed, or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, syringe, pipette, forceps, measured spoon, eye dropper or similar medically approved delivery vehicle.

The invention will now be described with reference to specific examples. It will be understood that the following examples are intended to describe embodiments of the invention and are not intended to limit the invention in any way.

EXAMPLES

Example 1

Preparation of Protein Kinase Inhibiting Compounds 1 to 10

Compounds 1 to 10 (shown below) were synthesized using standard procedures as represented by the following protocol for the preparation of compound 3. Compound 4, which does not contain a PNA moiety was synthesized on an Applied Biosystems Pioneer Peptide Synthesizer following the protocol provided by the manufacturer.

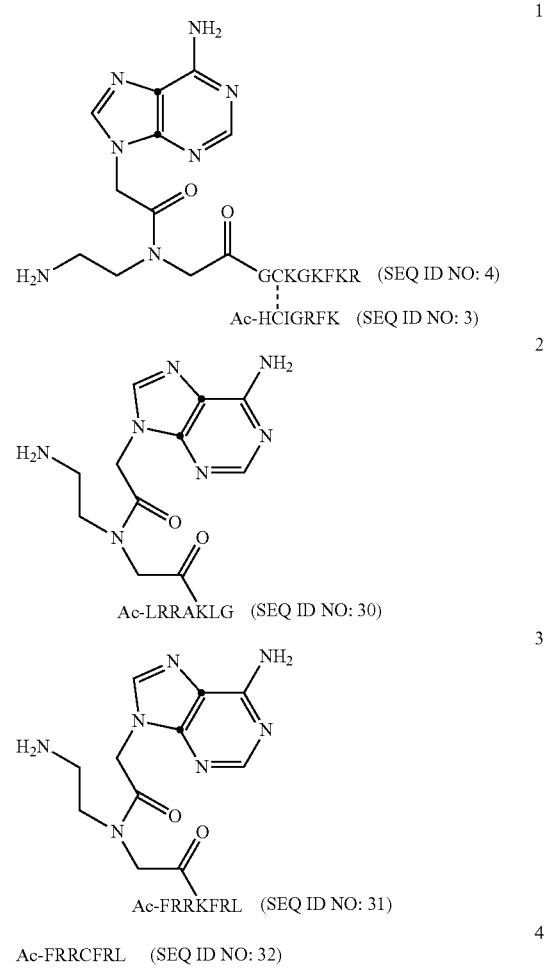

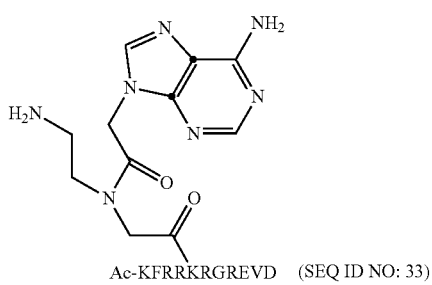

Ac-KFRRKRGREVD  (SEQ ID NO: 33)

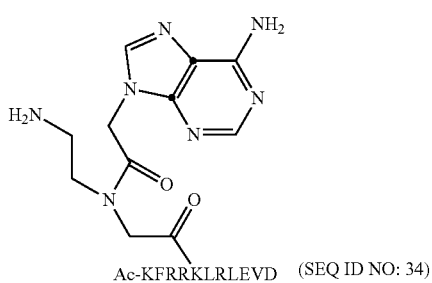

Ac-KFRRKLRLEVD  (SEQ ID NO: 34)

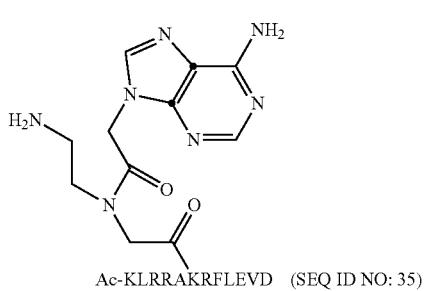

Ac-KLRRAKRFLEVD  (SEQ ID NO: 35)

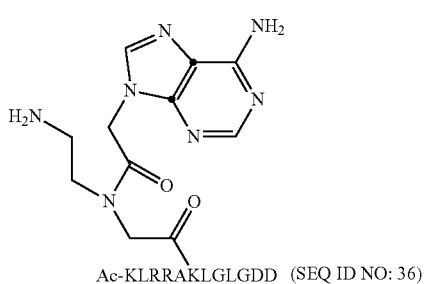

Ac-KLRRAKLGLGDD  (SEQ ID NO: 36)

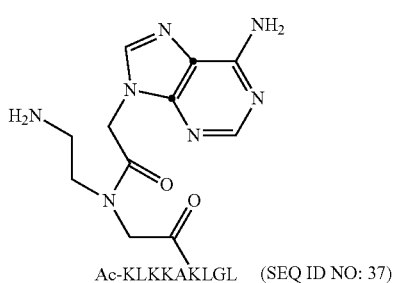

Ac-KLKKAKLGL  (SEQ ID NO: 37)

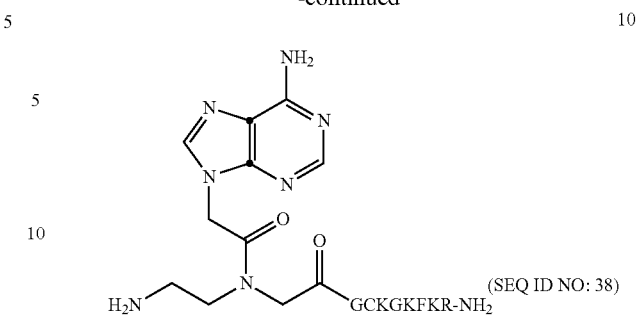

(SEQ ID NO: 38)
GCKGKFKR-NH$_2$

Preparation of Compound 3

The peptide chain FRRKFRL (SEQ ID NO:2) was synthesized on an Applied Biosystems Pioneer Peptide Synthesizer following the protocol provided by the manufacturer and employing Lys in which the side chain is protected with the amine protecting group ivDde.

After the peptide chain was synthesized, the ivDde protecting group was removed by washing the resin with DMF, isopropanol and dichloromethane, allowing the resin to dry for 20 min, then washing for 30 min with 2% Hydrazine (in DMF). The resin was then washed again with DMF, isopropanol and dichloromethane and allowed to dry.

Adenine peptide nucleic acid (PNA(Bhoc)) was coupled to the side chain of the Lys residue in the peptide chain by shaking the resin in DMF solvent with 2 eq activator HBTU/HOBt, 2 eq DIPEA and 2 eq PNA(Bhoc). After 12 hrs, the resin was washed and then submitted to a de-protection step to remove the Fmoc from the PNA by shaking the resin with 20% piperidine/DMF for 6 hrs. Finally, the peptide was cleaved from the resin using standard protocols. After filtering, the peptide was dissolved in H$_2$O (0.1% TFA) and purified by column chromatography.

Mass Spectrometry

The structure of the compounds was confirmed by electrospray mass spectrometry as follows. For compounds comprising a PNA moiety, mass spectral analysis was performed before and after addition of the PNA moiety.

Analysis by mass spectrometry was performed on a VG Quattro I (Fison, UK) mass spectrometer equipped with pneumatically-assisted electrospray ionisation source, operating in positive mode. The solvent system was 1:1 acetonitrile:water with 0.2% formic acid with a flow rate of 15 µl per minute. The source temperature was set at 85° C., an electrospray capillary was set at 3.5 kV with a cone voltage set at 20V. Data were collected in continuum mode between 200-2000 m/z with sweep time of 10 seconds. Spectra obtained for each compound were combinations of 5 consecutive scans and background subtraction. The respective mass of each compound was calculated using Transform mode in MassLynx 3.5 software.

Figure 2A:
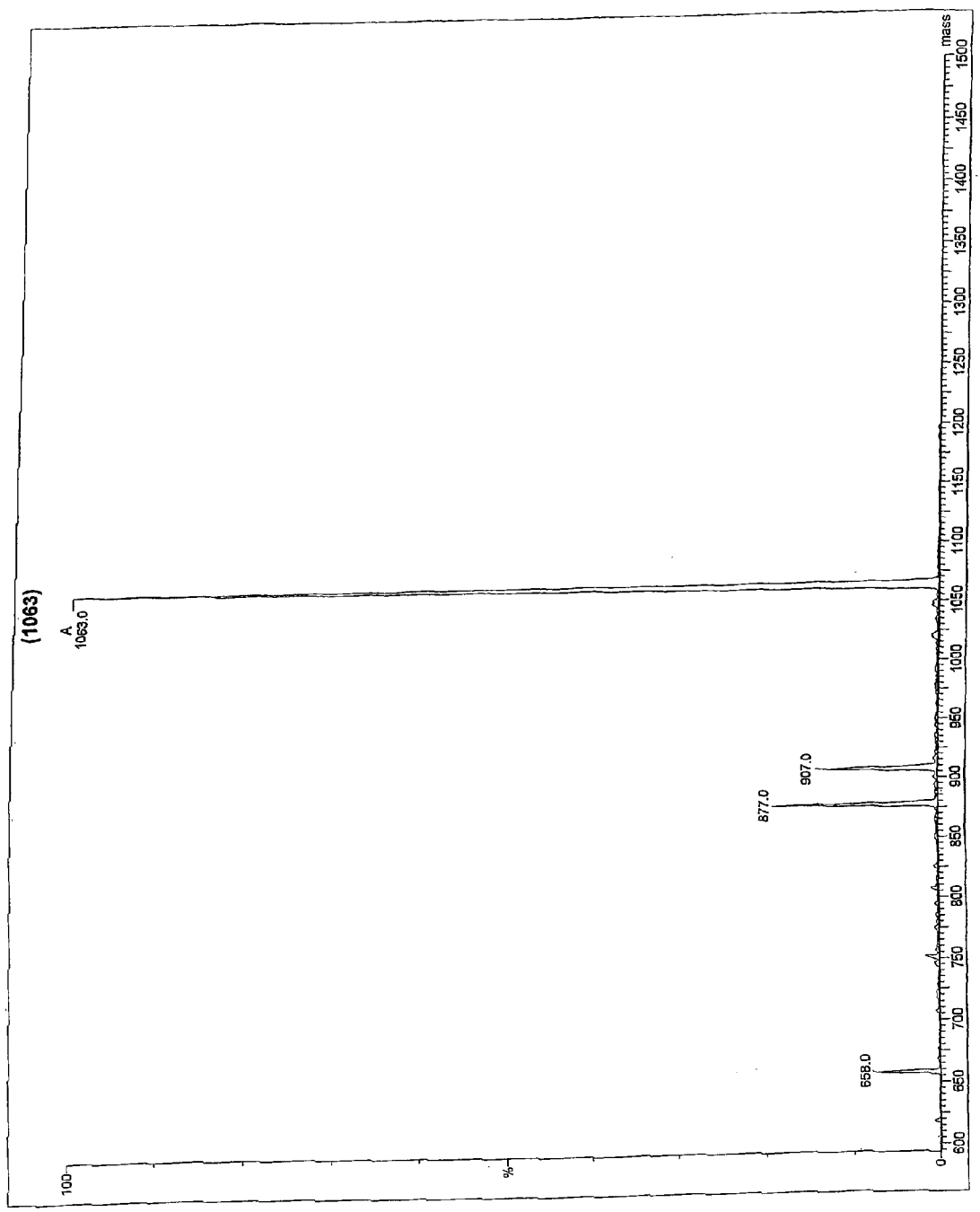
FIG. 2 depicts mass spectra for compound 3 before (A) and after (B) the addition of the adenine peptide nucleic acid (PNA) moiety.
Figure 2B:
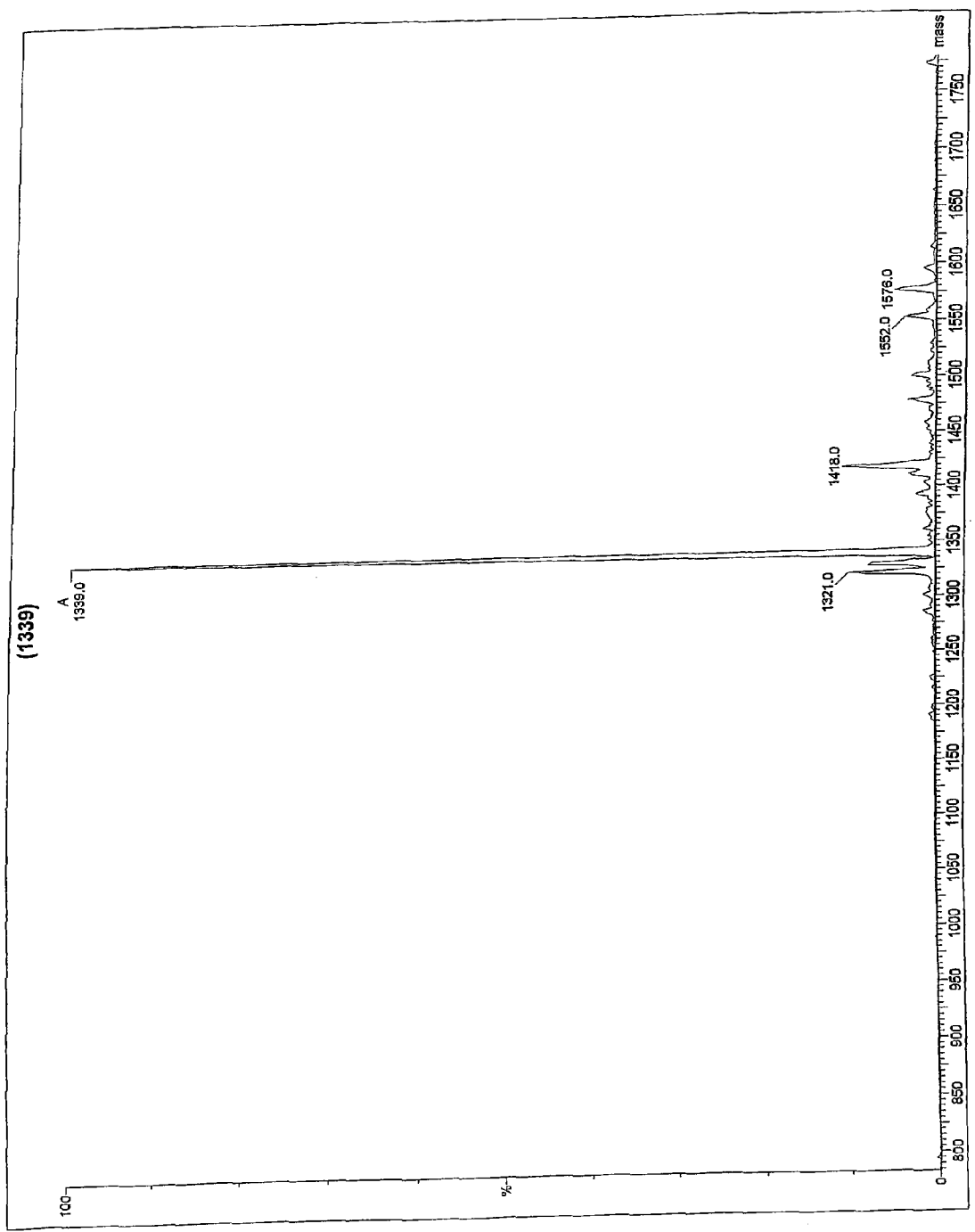

Representative spectra are shown in FIG. 2 for compound 3. FIG. 2A depicts the mass spectrum for compound 3 prior to addition of the PNA moiety and shows a peak at mass 1063. FIG. 2B depicts the mass spectrum for compound 3 after addition of the PNA moiety and shows a peak at mass 1339. The calculated mass for compound 3 without the PNA moiety is: 1063.14, and the calculated mass for compound 3 with the PNA moiety (mass 276) is: 1339.14.

The respective calculated and measured masses for compounds 1 to 10 are shown in Table 3.

TABLE 3

Calculated and Measured Mass for Compounds 1-10

| Compound | Calculated Mass | Measured Mass |
|---|---|---|
| 1 | 2138.35 | 2138 |
| 2 | 1129.15 | 1129 |
| 3 | 1339.14 | 1339 |
| 4 | 1038.16 | 1038 |
| 5 | 1762.73 | 1763 |
| 6 | 1775.81 | 1776 |
| 7 | 1846.83 | 1847 |
| 8 | 1657.58 | 1658 |
| 9 | 1314.47 | 1314 |
| 10 | 1239.15 | 1239 |

Example 2

In Vitro Inhibition of Purified PKC-Alpha with Compounds 1, 2 and 3

Figure 3:
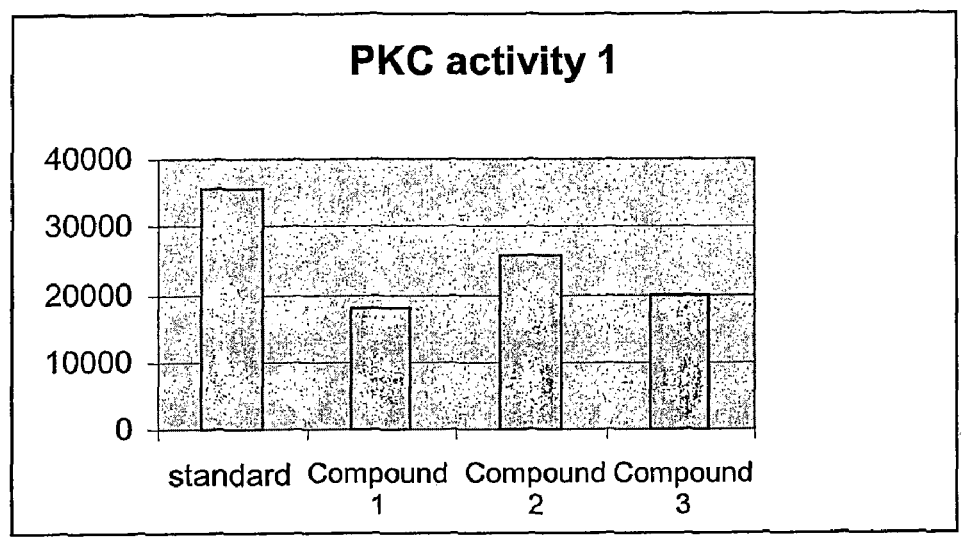
FIG. 3 depicts the in vitro inhibition of purified PKC-α with three compounds of the present invention.

The ability of each of compounds 1, 2 and 3 (shown above) to inhibit the activity of commercially purified PKC-alpha activity was tested. PKC-alpha was obtained from Upstate Cell Signalling Solutions #14-484 (Lake Placid N.Y.). The PKC-alpha activity assays were performed using the IQ TM PKC assay kit, a kit from Pierce Biotechnology (Rockford, Ill.), according to the manufacturer's instructions. Compounds 1, 2 and 3 were used at a concentration of 10 µg per assay. As shown in FIG. 3, all three compounds showed inhibitory activity. The relative activities are expressed in arbitrary fluorescence intensity units using Galaxy plate reader (BMG LabTech, GmbH, Offenburg/Germany). The assays were run in duplicate and repeated twice. The values shown in FIG. 3 are the average of 4 assays; "Standard" indicates the control reaction in the absence of any inhibitor.

Example 3

In Vitro Inhibition of PKC-Alpha in Cell Lysates with Compound 1

Figure 4:
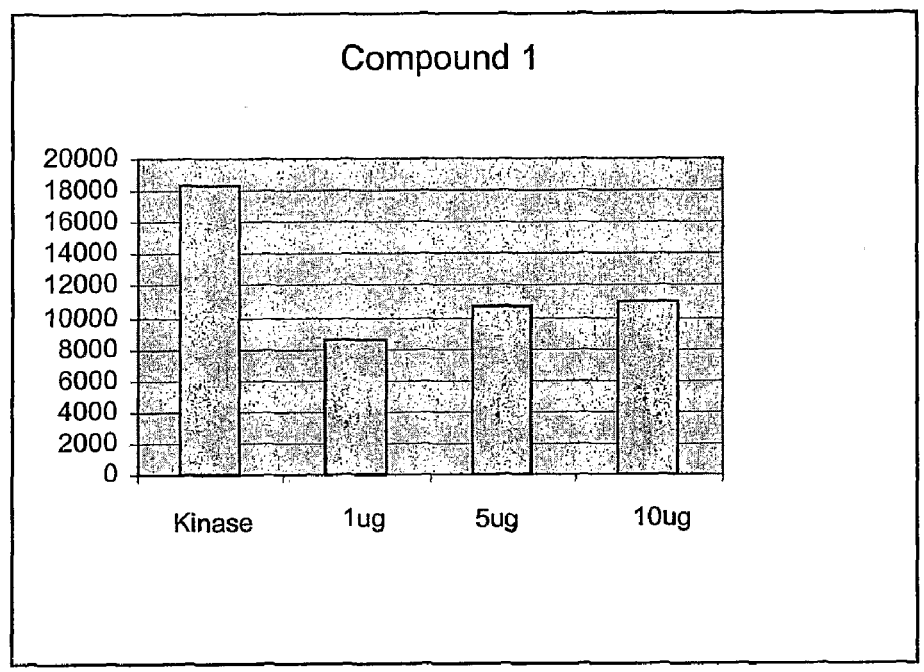
FIG. 4 depicts the in vitro inhibition of PKC-α sourced from a cell lysate with various doses of a compound of the present invention (compound 1).

Compound 1 was tested as described above (Example 2) except that the source of the PKC-alpha enzyme was a cell lysate from neuroblastoma IMR-32 cells that had been grown for 48 h. The cells ($1 \times 10^7$) were frozen at $-80°$ C. under a film (400 µl) of RIPA buffer supplemented with a cocktail of protease inhibitors and orthovanadate. The extract was thawed and centrifuged at 14,000×g for 10 min in a refrigerated centrifuge. The clear supernatant was used as the source of enzyme. The results are shown in FIG. 4; "Kinase" represents the activity of the untreated extract. Concentrations of compound 1 are as indicated. Compound 1 exhibits a good activity but no dose response was observed, suggesting that the compound may be active at lower concentration and also that other cellular kinases may compete for the compound.

Example 4

In Vitro Inhibition of PKC-Alpha in Cell Lysates with Compound 2

Figure 5:
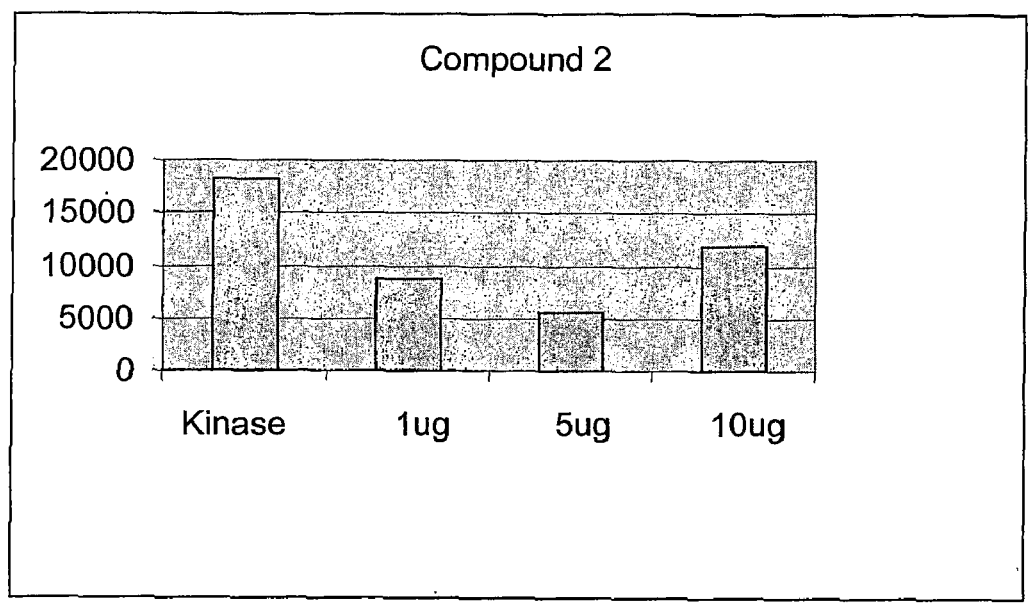
FIG. 5 depicts the in vitro inhibition of PKC-α sourced from a cell lysate with various doses of a compound of the present invention (compound 2).

Compound 2 was tested as described above (Example 3). The results are shown in FIG. 5; "Kinase" represents the activity of the untreated extract. Concentrations of compound 2 are as indicated. Compound 2 also exhibits a good activity but no dose response was observed, suggesting, as was the case with compound 1, that the compound may be active at lower concentration and also that other cellular kinases may compete for the compound. Examples 9 to 13 below confirm that the PKI compounds are capable of inhibiting protein kinases other than PKC-alpha and thus also confirms that the observed level of inhibition of PKC-alpha is affected by competition of other kinases for the PKI compound.

Example 5

In Vitro Inhibition of PKC-Alpha in Cell Lysates with Compound 3

Figure 6:
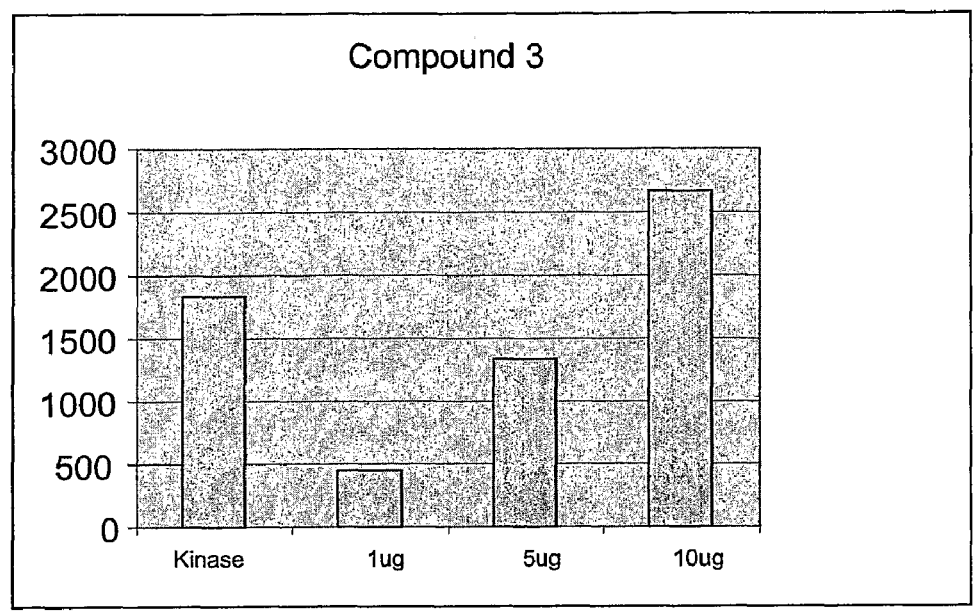
FIG. 6 depicts the in vitro inhibition of PKC-α sourced from a cell lysate with various doses of a compound of the present invention (compound 3).

Compound 3 was tested as described above (Example 3). The results are shown in FIG. 6; "Kinase" represents the activity of the untreated extract. Concentrations of compound 3 are as indicated. Compound 3 exhibits a good activity at 1 µg suggesting that it is active at lower concentration. However, compound 3 shows a "reverse dose response" when assayed against the cell lysate, which contrasts with the observation that compound 3 drastically inhibits the standard purified PKC-alpha at the dose 10 µg (FIG. 3).

Example 6

In Vitro Inhibition of Cancer Cell Proliferation with Compound 1

The ability of the compound 1 to inhibit cancer cell proliferation was tested in vitro using the human neuroblastoma cell line IMR-32. Monolayer cell cultures were trypsinized and compound 1 was added at the doses indicated in Table 4 and internalized by pinocytic endocytosis using Influx TM pinocytic cell-loading reagent, a kit from Molecular Probes; (Eugene, Oreg.) following the manufacturer's recommendations. The indicated doses refer to the concentration in the loading medium, which was used on $1 \times 10^6$ cells in a 10 µl volume, i.e. contained 10 µg to 100 ug of compound 1 that provides 10 fg to 100 fg per cell. It is worth noting, however, that only a small proportion of the compound is internalized using this technique, so the actual dose may be lower. The cells were treated on day 0 of the experiment. The cells loaded with compound 1 were cultured in 96 well plates (5,000 cells in 100 µl per well), and the proliferation was monitored over 3 consecutive days. The increase in cell population was quantified using a Hoechst reagent-based assay (modified from Rao and Otto, 1992, *Analytical Biochem.* 207:186-192) that measures the total DNA of the population. The measurements were obtained as relative fluorescence intensity, a value that is directly correlated to the total number of cells. The results are shown in Table 4. Data are expressed as a percentage of matching controls that were supplemented with culture medium alone. There was a clear dose response in the inhibition of the IMR-32 cells with compound 1. As can be seen from the results in Table 4, there is an inverse correlation between the concentration of compound 1 and the level of inhibition indicating that the compound is active at very low doses, but that once the compound saturates the cells, it may be competed for by a number of different protein kinases.

TABLE 4

Inhibition of IMR-32 Cell Proliferation with Compound 1 Treatment

|  | CT[2] | CT + MP[3] | Compound 1 (mg/ml) | | | |
|---|---|---|---|---|---|---|
|  |  |  | 1.0 | 2.5 | 5.0 | 10.0 |
| 24 h |  |  |  |  |  |  |
| Average cell no.[1] | 908 | 749 | 226 | 552 | 532 | 557 |
| % survival |  |  | 30 | 74 | 71 | 74 |
| % inhibition |  |  | 70 | 26 | 29 | 26 |
| 48 h |  |  |  |  |  |  |
| Average cell no.[1] |  | 1326 | 368 | 937 | 921 | 929 |
| % survival |  |  | 28 | 71 | 69 | 70 |
| % inhibition |  |  | 72 | 29 | 31 | 30 |
| 72 h |  |  |  |  |  |  |
| Average cell no.[1] |  | 1287 | 358 | 1104 | 999 | 1009 |
| % survival |  |  | 28 | 86 | 78 | 78 |
| % inhibition |  |  | 72 | 14 | 22 | 22 |

[1]Average of 2 × 12 replicas per assay
[2]Untreated control cells
[3]Control cells treated with pinocytic endocytosis reagent alone

Example 7

In Vitro Inhibition of Cancer Cell Proliferation with Compound 2

The ability of the compound 2 to inhibit cancer cell proliferation was tested in vitro using the human neuroblastoma cell line IMR-32 as described in Example 6. Results are shown in Table 5.

TABLE 5

Inhibition of IMR-32 Cell Proliferation with Compound 2 Treatment

|  | CT[2] | CT + MP[3] | Compound 2 (mg/ml) | | | |
|---|---|---|---|---|---|---|
|  |  |  | 1.0 | 2.5 | 5.0 | 10.0 |
| 24 h |  |  |  |  |  |  |
| Average cell no.[1] |  | 746 | 382 | 526 | 516 | 516 |
| % survival |  |  | 51 | 71 | 69 | 69 |
| % inhibition |  |  | 49 | 29 | 31 | 31 |
| 48 h |  |  |  |  |  |  |
| Average cell no.[1] |  | 1376 | 669 | 1090 | 1099 | 981 |
| % survival |  |  | 49 | 79 | 80 | 71 |
| % inhibition |  |  | 51 | 21 | 20 | 29 |
| 72 h |  |  |  |  |  |  |
| Average cell no.[1] | 1151 | 1155 | 1240 | 1023 | 1140 | 1081 |
| % survival |  |  | 90 | 74 | 83 | 79 |
| % inhibition |  |  | 10 | 26 | 17 | 21 |

[1]Average of 2 × 12 replicas per assay
[2]Untreated control cells
[3]Control cells treated with pinocytic endocytosis reagent alone

Example 8

In Vitro Inhibition of Cancer Cell Proliferation with Compound 3

The ability of the compound 3 to inhibit cancer cell proliferation was tested in vitro using the human neuroblastoma cell line IMR-32 as described in Example 6. Results are shown in Table 6.

TABLE 6

Inhibition of IMR-32 Cell Proliferation with Compound 3 Treatment

|  | CT[2] | CT + MP[3] | Compound 3 (mg/ml) | | | |
|---|---|---|---|---|---|---|
|  |  |  | 1.0 | 2.5 | 5.0 | 10.0 |
| 24 h |  |  |  |  |  |  |
| Average cell no.[1] | 998 | 740 | 340 | 475 | 654 | 683 |
| % survival |  |  | 46 | 64 | 88 | 92 |
| % inhibition |  |  | 54 | 36 | 12 | 8 |
| 48 h |  |  |  |  |  |  |
| Average cell no.[1] | 1339 | 1127 | 311 | 452 | 578 | 612 |
| % survival |  |  | 42 | 61 | 78 | 83 |
| % inhibition |  |  | 58 | 39 | 22 | 17 |
| 72 h |  |  |  |  |  |  |
| Average cell no.[1] | 1605 | 1637 | 379 | 949 | 1042 | 1540 |
| % survival |  |  | 23 | 58 | 64 | 94 |
| % inhibition |  |  | 77 | 42 | 36 | 6 |

[1]Average of 2 × 12 replicas per assay
[2]Untreated control cells
[3]Control cells treated with pinocytic endocytosis reagent alone Table 7, below, provides a summary of the data relating to the inhibition of the human neuroblastoma cell line IMR-32 with compounds 1, 2 and 3 at a single dose of 1 mg/ml. This dose refers to that of the loading medium used on $1 \times 10^6$ cells in a 10 μl volume, i.e. containing 10 μg of the respective compound. Thus, the maximum dose that each cell could receive is 0.01 ng, however, as indicated above, a small proportion only of the test compound is internalized using this technique and the actual dose may, therefore, be lower. The data in Table 7 are expressed as a percentage of control cells treated with culture medium alone.

TABLE 7

Comparison of Growth Inhibition of Neuroblastoma Cells IMR-32 by Compounds 1, 2 and 3

| Time point | Compound 1 | Compound 2 | Compound 3 |
|---|---|---|---|
| 24 h | 54% | 49% | 70% |
| 48 h | 58% | 51% | 72% |
| 72 h | 77% | 10% | 72% |

Example 9

In Vitro Inhibition of Protein Kinase C Isoforms with Compounds 1 to 10

The inhibitory effect of the PKI compounds 1 to 10 (shown above) on purified commercially available isoforms representative of the 3 classes of PKC: cPKC (alpha, betaI/II) nPKC (delta and epsilon) aPKC (zeta) was assayed using the PepTag® Non-Radioactive PKC Assay (Promega, Madison, Wis.). The zeta isoform was tested with this assay although its affinity for the substrate provided in the kit was relatively low. The amount of enzyme in the reaction mixture for the PKC zeta assays was multiplied by 2. The assay was used following the manufacturer's recommendations. The principle of the assay is based on the difference in charge of phosphorylated (negatively charged) form versus the non-phosphorylated form of a fluorescent substrate. The two forms can be separated by gel electrophoresis and the negatively charged band excised and the fluorescence measured (exc. 440 nm and em. 590 nm) in 96 well plates on a Galaxy FluoStar plate reader. The PKI compounds were added to the assay mixture at 3 doses: 150, 300 and 600 μM and an extra 75 μM when the inhibition was too high. The assay is strictly biochemical and the doses of the compounds used, therefore, are generally not correlative with in vivo situations. The results are shown in Table 8.

TABLE 8

Effect of Compounds 1-10 on PKC Isoforms (% Inhibition)

| Compound | Dose/ μM | PKC Isoform | | | | | |
|---|---|---|---|---|---|---|---|
| | | alpha | beta 1 | beta 2 | delta | epsilon | zeta |
| 5 | 150 μM | 95 | 87 | 88 | 86 | 78 | 25 |
|   | 300 μM | 94 | 90 | 79 | 91 | 81 | 71 |
|   | 600 μM | 95 | 90 | 77 | 90 | 84 | 63 |
| 6 | 150 μM | 76 | 89 | 87 | 86 | 59 | 24 |
|   | 300 μM | 91 | 91 | 91 | 83 | 85 | 36 |
|   | 600 μM | 92 | 92 | 91 | 85 | 85 | 54 |
| 7 | 150 μM | 84 | 87 | 92 | 80 | 0 | 0 |
|   | 300 μM | 94 | 87 | 95 | 83 | 67 | 15 |
|   | 600 μM | 95 | 88 | 95 | 84 | 79 | 58 |
| 4 | 150 μM | 80 | 72 | 83 | 90 | 55 | 60 |
|   | 300 μM | 80 | 72 | 83 | 90 | 55 | 60 |
|   | 600 μM | 80 | 82 | 82 | 95 | 77 | 58 |
| 8 | 150 μM | 83 | 73 | 90 | 83 | 41 | 0 |
|   | 300 μM | 87 | 81 | 94 | 86 | 77 | 28 |
|   | 600 μM | 89 | 83 | 91 | 85 | 82 | 22 |
| 1 | 150 μM | 78 | 71 | 78 | 56 | 54 | 15 |
|   | 300 μM | 84 | 92 | 90 | 61 | 58 | 10 |
|   | 600 μM | 87 | 93 | 92 | 88 | 83 | 20 |
| 9 | 150 μM | 12 | 8 | −54* | −44* | 0 | 0 |
|   | 300 μM | 70 | 88 | 58 | 9 | 0 | 0 |
|   | 600 μM | 92 | 88 | 81 | 66 | 88 | 0 |
| 2 | 150 μM | −24* | 18 | −59* | 59 | 58 | 0 |
|   | 300 μM | 35 | 52 | 61 | 79 | 67 | 6 |
|   | 600 μM | 83 | 70 | 74 | 84 | 84 | 20 |
| 3 | 150 μM | 47 | 37 | 31 | 32 | 38 | 37 |
|   | 300 μM | 51 | 76 | 83 | 41 | 53 | 40 |
|   | 600 μM | 82 | 80 | 81 | 70 | 68 | 56 |
| 10 | 150 μM | 6 | 7 | 26 | 84 | 62 | −27* |
|   | 300 μM | 73 | 82 | 64 | 92 | 84 | 0 |
|   | 600 μM | 75 | 81 | 76 | 89 | 85 | 17 |

*Negative values indicate that the compound had an activation effect on the enzyme.

As can be seen from Table 8, the PKI compounds show some specificity toward the PKC isoforms of the panel in that they are more active against the cPKCs (alpha, betaI/II), which share a similar structure for the catalytic site, and are less potent against the nPKCs (delta and epsilon) and aPKC (zeta), which are reported to have different catalytic site structures to that of the cPKCs.

Compounds 1, 4, 5, 7 and 8 are very potent inhibitors of all the PKCs isoforms except PKC epsilon and zeta. At the higher concentration of 300 μM the inhibition of the PKCs alpha to delta is almost complete with all of these compounds. In contrast, in PKC epsilon, there is a dose response up to 600 μM, a dose that is not sufficient to achieve complete inhibition. A similar pattern is observed with PKC zeta, which is less sensitive than epsilon to the compounds. Replacement of the amino acids LRL in compound 6 with RGR in compound 1 appears to confer a higher specificity of the compound toward PKC alpha.

Example 10

In Vitro Inhibition of Protein Kinases PKA, CDK2, Akt/PKB, MAPKp38 and CK2a2 with Compounds 1 to 10

The ability of the PKI compounds to inhibit PKA, CDK2, Akt/PKB, MAPKp38 and CK2a2 protein kinases was assessed using the Luminescence Kinase Glo® Kit (Promega V6711) according to the manufacturer's instructions. In brief the protocol was as follows:

All kinases were prepared in their respective 1× buffers. 20 μL of @X reaction buffer was added to each well. 10 μL of PKI compound and 10 μL of the test kinase solution were added followed by 10 μL of the Reaction Solution (containing activators, ATP and substrate). The reactions were incubated at 30° C. for 30 min and then 50 μL of Kinase-Glo® was added. Luminescence was measured after 10-15 min on a Galaxy reader. Results are shown in Table 9 below.

TABLE 9

Effect of Compounds 1-10 on Protein Kinases (% Inhibition at 150 μM concentration)

| Compound | Protein Kinase | | | | |
|---|---|---|---|---|---|
| | PKA | MAPKp38 | Akt/PKB | CDK2 | CK2a2 |
| 5 | 78 | 100 | −6* | −18* | 0 |
| 6 | 61 | 95 | −10* | −18* | 0 |
| 7 | 78 | 100 | −7* | −17* | 0 |
| 4 | 80 | 71 | 31 | −14* | 0 |
| 8 | 64 | 100 | 0 | −17* | 0 |
| 1 | 85 | 100 | −31* | −17* | 0 |
| 9 | 66 | 100 | 7 | −16* | 0 |
| 2 | 70 | 100 | 13 | −16* | 0 |
| 3 | 90 | 100 | 56 | −11* | 0 |
| 10 | 74 | 61 | 21 | −15* | 0 |

*Negative values indicate that the compound had an activation effect an the enzyme.

From Table 9, it can be seen that all of compounds 1 to 10 inhibit PKA and MAPKp38, suggesting that the catalytic site of these kinases has a conformational similarity to the catalytic site of PKCα. That all the compounds are capable of inhibiting PKA is in line with the fact that PKA and PKC are very close enzymes structurally, with the exception of their regulatory domain. The lack of activity of the compounds towards cyclin-dependent kinase 2 (CDK2) and casein kinase 2 alpha 2 (CK2a2) points to these kinases having a catalytic site structure that differs strikingly from the general kinase catalytic site configuration.

Compound 3 also demonstrates a consistent inhibitory activity toward Akt/PKB, an enzyme of importance in tumour development and proliferation.

Example 11

Effect of Compounds 1 to 10 on STAT-3

STAT-3 acts as a latent transcription factor. It can act as a transducer and as an activator of transcription. STAT-3 is phosphorylated on two sites: on a tyrosine residue (Tyr 705) and a serine residue (Ser 727). The Tyr site is phosphorylated by a tyrosine kinase of the Src kinases family (SrcFK), while the Ser residue is phosphorylated through the mTor pathway and JNK kinases. STAT-3 is only fully activated after the phosphorylation of the Ser residue. Following full activation, the STAT molecule dimerizes and translocates to the nucleus. The effect of the PKI compounds on SrcFK, mTor and/or JNK kinases was studied indirectly by examining the effect of the compounds on STAT-3.

The U-251 human glioblastoma cell line was used to test the activity of the PKI compounds on the phosphorylation of the Ser and Tyr residues in STAT-3 following treatment of the cells with IL-6 cytokine (an autocrine cytokine of glioblastoma) for 24 h at 10 ng per mL of medium. Compounds were used at a concentration of 5 mM in 10 μL medium without serum and internalised into the cells using pinocytic endocytosis according to the manufacturers instructions (Molecular Probes, Eugene, Oreg.). The immunocytochemistry experiment was performed using antibodies specifically recognising the consensus sites of phosphorylation of Ser727 and Tyr 705. The fluorescence was measured after 48 h using the appropriate antiphosphoSTAT antibodies after conventional cell fixation with 4% formaldehyde, Triton X100 permeabilization and methanol post-fixation. Note that the pSerSTAT antibody shows that the protein is located into the nucleus. The two pSTAT antibodies used in this experiment were obtained from Santa Cruz Biotechnology (rabbit polyclonal pSTAT3 Ser-727R # sc-8001-R and goat polyclonal Tyr 705# sc-7993). The secondary antibodies were Alexa Fluor 488 # A11008 and donkey anti goat # A11055. The fluorescence intensity of the fields was measured using an Olympus microscope equipped with epifluorescence and ImagePro software. The results are shown in Table 10.

TABLE 10

Effect of Compounds 1 to 10 (5 mM) on STAT-3 Phosphorylation in U-251 Glioblastoma Cells

| Compound | Anti-Serine Antibody FL Density | Anti-Tyrosine Antibody FL Density |
|---|---|---|
| Control | 70.15 | 43 |
| 5 | 97.7 | 39.1 |
| 6 | 115.77 | 42.49 |
| 7 | 97.55 | 43.66 |
| 4 | 92.46 | 37.24 |
| 8 | 77.36 | 21.11 |
| 1 | 91.2 | 31.65 |
| 9 | 89.48 | 29.67 |
| 2 | 98.83 | 30.58 |
| 3 | 90.2 | 46.56 |
| 10 | 95.07 | 30.45 |

No effect on Ser phosphorylation was observed for any of the tested compounds. Compound 8 inhibited Tyr phosphorylation by ~50% and compounds 1, 2 and 10 were inhibitory by ~30%.

Example 12

Effect of Compounds 1 to 10 on the pERK1/2 Phosphorylation and MEK1/2 Protein Kinase Activity pERK1/2 are the last kinases of the Ras/Raf cascade. The phosphorylation of ERK1/2 by its immediate upstream kinase MEK1/2 results in the translocation of the phosphorylated form into the nucleus. The effect of PKI compounds 1 to 10 on MEK1/2 kinase was thus indirectly evaluated by studying the effect of the compounds on pERK1/2 in IMR-32 neuroblastoma cells.

The IMR32 cells were starved in a medium deprived of serum for 2 hours and further stimulated for 30 minutes by addition of serum to the medium. Compounds were used at a concentration of 5 mM in 10 µL medium without serum per 1 million cells using pinocytic endocytosis according to the manufacturers instructions (Molecular Probes, Eugene, Oreg.). Serum stimulation is known to initiate the cascade that ends in the phosphorylation of ERK1/2 and further translocation of the phosphorylated forms into the nucleus. The intensity of the fluorescence obtained by labelling the pERK protein was measured using a Coulter microscope equipped with epifluorescence and ImagePro software. The antibodies used were rabbit polyclonal anti active pERK (pTEpy) # V8031 from Promega, Inc. and the secondary antibody is the Alexa Fluor 488 goat anti-rabbit (H=L) # A11008 from Molecular Probes-Invitrogen. Protocols were according to conventional fixation and immunological labelling. The results are summarised in Table 11 below.

TABLE 11

Effect of Compounds 1 to 10 (5 mM) on pERK1/2 in IMR-32 Neuroblastoma Cells

| Compound | FL Density |
|---|---|
| Control starved | 59.5 |
| Control stimulated | 105.3 |
| Control MP | 99.5 |
| 5 | 100.3 |
| 6 | 93.5 |
| 7 | 55.9 |
| 4 | 80.5 |
| 8 | 83.9 |
| 1 | 59.9 |
| 9 | 91.4 |
| 2 | 93 |
| 3 | 99.6 |
| 10 | 93.7 |

Compounds 7 and 1 showed the greatest inhibition of the translocation of pERK1/2 into the nucleus and decreased its phosphorylation (as measured by a decrease in fluorescence intensity) and thus inhibit MEK1/2.

Example 13

Effect of Compounds 1 to 10 on Bcl-2 Sublocalisation

Bcl2 is an anti-apoptotic membrane protein located in the endoplasmic reticulum (ER), the nuclear envelope, the mitochondrial membrane and in the nuclei of dividing cells. It is phosphorylated and activated by PKC alpha and MAPK ERK1/2 on multiple serine residues, the most prominent ones being Ser70 and Ser87. The phosphorylation of the Bcl2 protein alters its binding to Bax and consequently triggers or inhibits the apoptotic cascade depending on the phosphorylation state of the two proteins. Beside their antiapoptotic effects, Bcl2 species located at the ER regulates ER calcium, cellular pH and ER resident proteins.

Cells were grown in appropriate medium then fixed and labelled with a rabbit polyclonal anti Bcl-2 antibody (N-19), #sc-492 from Santa Cruz Biotechnology using conventional techniques. Secondary antibody was Alexa fluor 488 anti-rabbit IgG (H+L) # A11008 from Molecular Probes-Invitrogen. Results are shown in Table 12, in which the numbers reflect the intensity of the label in the cellular location indicated.

TABLE 12

Effect of Compounds 1 to 10 on Bcl2 Sublocalization

| Compound | Nuclear | Perinuclear | Cytoplasmic |
|---|---|---|---|
| Control | 2 | 0 | 1 |
| 5 | 1 | 2 | 2 |
| 6 | 1 | 2 | 2 |
| 7 | 1 | 2 | 4 |
| 4 | 0.5 | 2 | 1 |
| 8 | 2 | 2 | 1 |
| 1 | 2 | 1 | 1 |
| 9 | 0.5 | 0 | 1 |

TABLE 12-continued

Effect of Compounds 1 to 10 on Bcl2 Sublocalization

| Compound | Nuclear | Perinuclear | Cytoplasmic |
|---|---|---|---|
| 2 | 3 | 1 | 1 |
| 3 | 2.5 | 1 | 1 |
| 10 | 3 | 1 | 1 |

Compounds 4 and 9 showed the greatest inhibition of the expression of Bcl2 and thus could act to potentiate the effect of apoptotic drugs. Treatment of the cells with compounds 2 and 10 mediates the translocation of the Bcl2 protein in the nucleus, whereas treatment with compound 7 seems to favour the localisation of Bcl2 in the cytoplasm.

Example 14

Effect of Compounds 1 to 10 on Cancer Cell Proliferation

The induction of cell death and the alteration of cell proliferation in 10 cell lines representative of different cancers were studied following individual incorporation of compounds 1 to 10 into the cells via pinocytic influx. The compounds were used at concentrations of 5 mM and 10 mM. These concentrations do not, however, directly correlate with the amount of the compound actually received by the cells, as noted in Example 6. The cell lines employed were as follows: U-251 glioblastoma cell line; H-661 non-small cell lung cancer cell line; IMR-32 neuroblastoma cell line; LNCap and DU-145 prostate cancer cell lines; LS-180 colon cancer cell line; MCF-7 and MDA-MB-231 breast cancer cell lines; SKOV-3 ovarian cancer cell line and T-24 bladder cancer cell line. Breast cancer cell lines MCF-7 and MDA-MB-231 differ both in their expression of oestrogen receptors (MCF-7+) and aggressiveness. MDA-MB-231 is an oestrogen negative cell line expressing Her/Erb-2 and is representative of metastatic breast tumours. Similarly, of the two prostate cancer cell lines, LNCap is an androgen insensitive cell line and DU145 is an androgen positive cell line.

The methodology used was as follows. The starting cell suspension density was $1 \times 10^6$ cells/ml. Each PKI compound was incorporated to each given cell line at 5 mM and 10 mM concentration in 10 µl by pinocytic endocytosis (Invitrogen/Molecular Probe) following supplier recommendations. 5000 cells were distributed in 96 well plates in appropriate media containing 10% FBS and allowed to grow for 24, 48 and 72 hrs. Following endocytosis, the cell suspension was plated as such without elimination of the dead cells. The size of the cell populations was further assessed as total DNA (a value that directly relate to the number of cells; see Example 6).

The experimental setting outlined above allowed the primary effect of each compound on cell death to be measured over the 24 h following incorporation of the PKI compound. The difference in population size of the control untreated cells and the treated cells at the time point 24 h thus measures the death toll. During the next 48 h the proliferation patterns reflect whether the compound alters growth and also indirectly informs on the stability of the compounds. Thus, the experimental set up permits the simultaneous estimation of apoptosis, proliferation index of the resistant or unloaded cells and persistence of the PKI compound in the cells or endogenous stability.

The percentage cell death at 24 h (short term) is shown in Tables 13 and 14.

TABLE 13

Percentage Cell Death at 24 h after Treatment with Compounds 1 to 10 at 5 mM

| | Cell line | | | | | | | | | |
|---|---|---|---|---|---|---|---|---|---|---|
| Compound | H661 | MCF-7 | MDA-MB-231 | SKOV-3 | LnCAP | Du145 | T24 | IMR32 | LS180 | U251 |
| 5 | 17 | 15 | 22 | 5 | 1 | 20 | 14 | 11 | 42 | 6 |
| 6 | 21 | 19 | 3 | 29 | 15 | 22 | 35 | 2 | 30 | 6 |
| 7 | 7 | 29 | 27 | 14 | 5 | 5 | 17 | 7 | 28 | 17 |
| 4 | 16 | 48 | 48 | 8 | 70 | 11 | 23 | 11 | 51 | 70 |
| 8 | 11 | 59 | 13 | 12 | 24 | 28 | 5 | 9 | 21 | 4 |
| 1 | 46 | 18 | 1 | 1 | 16 | 17 | 1 | 2 | 1 | 7 |
| 9 | 8 | 31 | 34 | 21 | 15 | 36 | 12 | 5 | 24 | 11 |
| 2 | 6 | 3 | 8 | 2 | 13 | 1 | 3 | 0 | 48 | 31 |
| 3 | 1 | 25 | 1 | 5 | 3 | 29 | 1 | 19 | 9 | 7 |
| 10 | 13 | 26 | 21 | 1 | 11 | 6 | 3 | 23 | 13 | 10 |

TABLE 14

Percentage Cell Death at 24 h after Treatment with Compounds 1 to 10 at 10 mM

| | Cell line | | | | | | | | | |
|---|---|---|---|---|---|---|---|---|---|---|
| Compound | H661 | MCF-7 | MDA-MB-231 | SKOV-3 | LnCAP | Du145 | T24 | IMR32 | LS180 | U251 |
| 5 | 22 | 36 | 36 | 43 | 4 | 25 | 28 | 27 | 56 | 16 |
| 6 | 25 | 39 | 19 | 29 | 17 | 28 | 42 | 14 | 58 | 16 |
| 7 | 17 | 36 | 29 | 36 | 16 | 11 | 17 | 13 | 55 | 21 |

TABLE 14-continued

Percentage Cell Death at 24 h after Treatment with Compounds 1 to 10 at 10 mM

| | Cell line | | | | | | | | | |
|---|---|---|---|---|---|---|---|---|---|---|
| Compound | H661 | MCF-7 | MDA-MB-231 | SKOV-3 | LnCAP | Du145 | T24 | IMR32 | LS180 | U251 |
| 4 | 20 | 60 | 52 | 22 | 76 | 13 | 29 | 24 | 53 | 76 |
| 8 | 18 | 79 | 19 | 31 | 30 | 52 | 11 | 11 | 28 | 44 |
| 1 | 12 | 21 | 5 | 9 | 19 | 14 | 4 | 7 | 2 | 16 |
| 9 | 8 | 56 | 40 | 22 | 23 | 43 | 17 | 17 | 44 | 29 |
| 2 | 34 | 29 | 13 | 14 | 11 | 8 | 3 | 0 | 52 | 32 |
| 3 | 19 | 15 | 21 | 16 | 22 | 32 | 22 | 21 | 12 | 14 |
| 10 | 16 | 29 | 33 | 5 | 23 | 40 | 28 | 30 | 18 | 21 |

Figure 7:
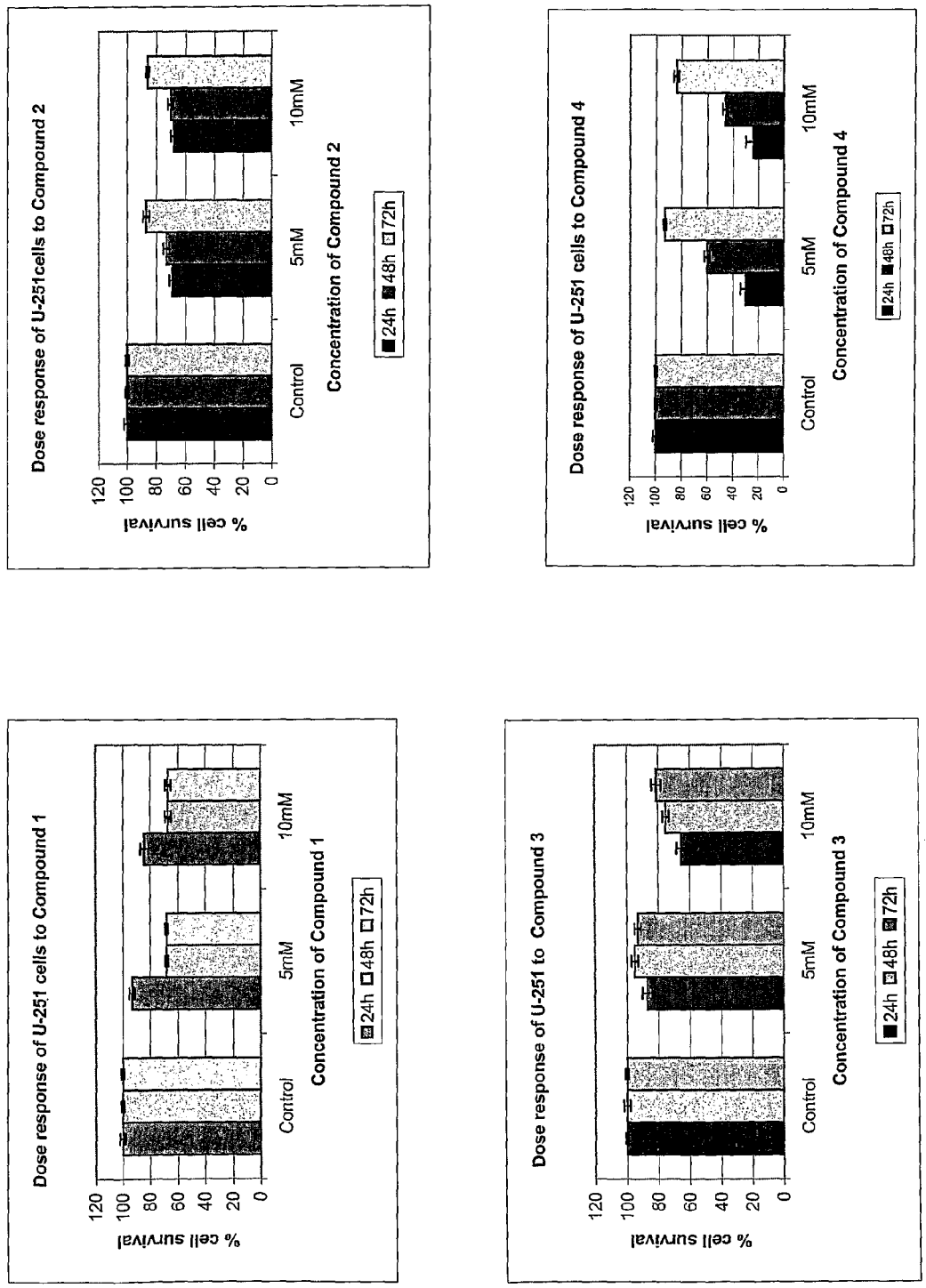
FIG. 7 depicts the effect of compounds 1 to 10 on proliferation of U-251 glioblastoma cells.
Figure 7:
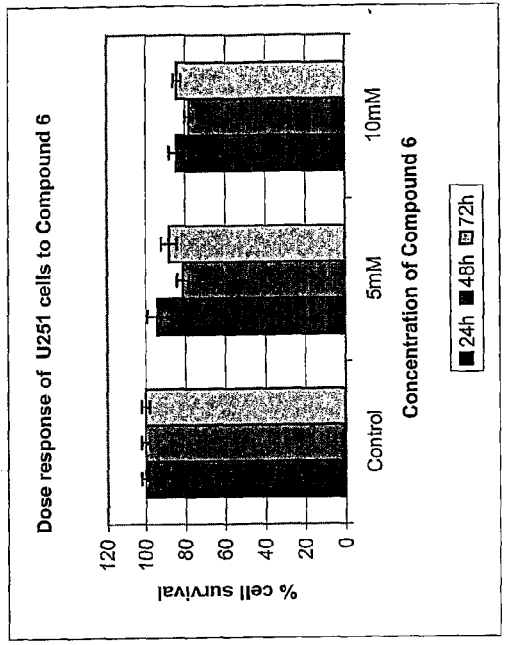
Figure 7:
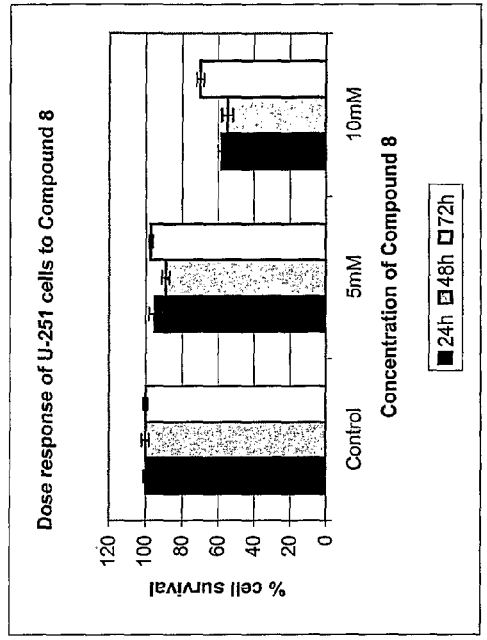
Figure 7:
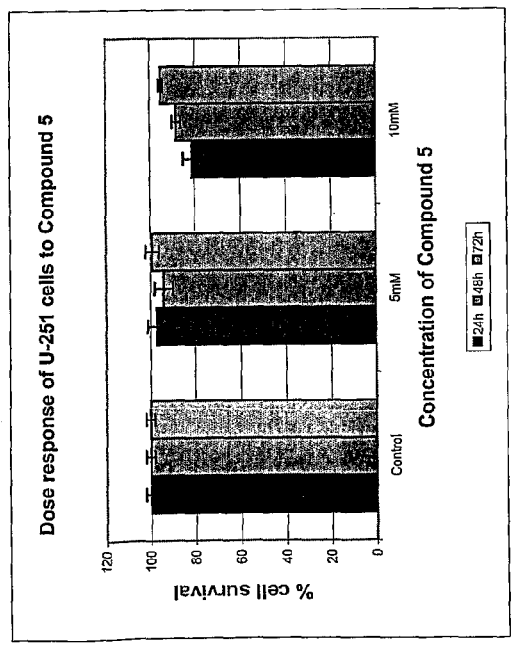
Figure 7:
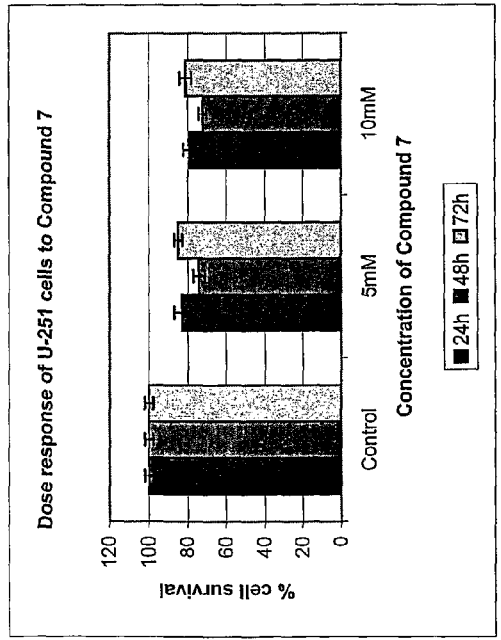
Figure 7:
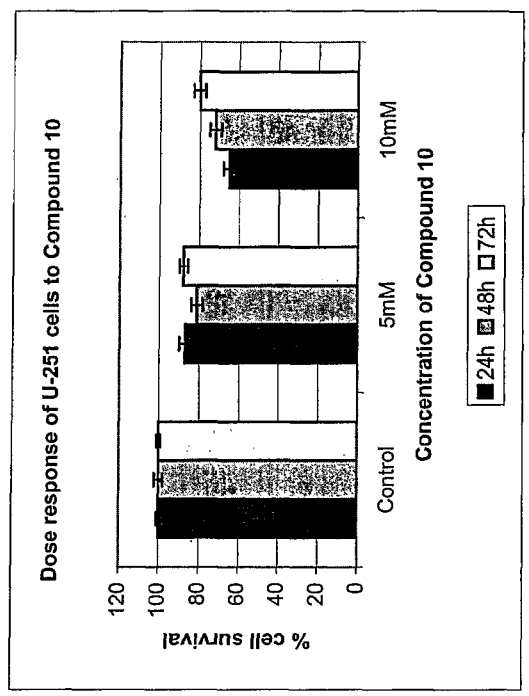
Figure 7:
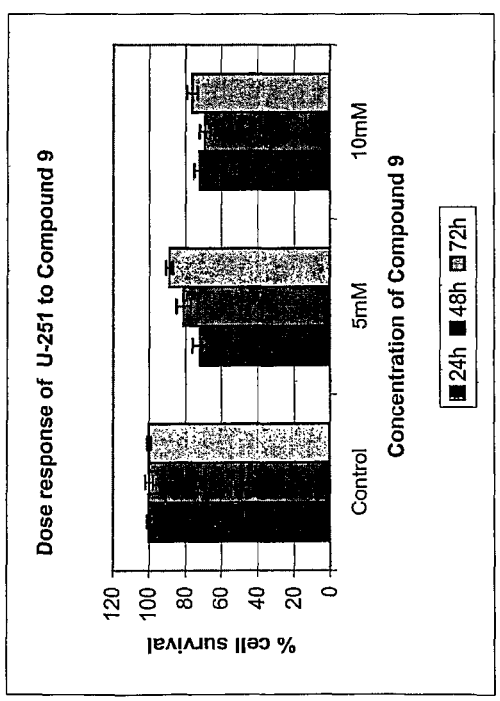
Figure 8:
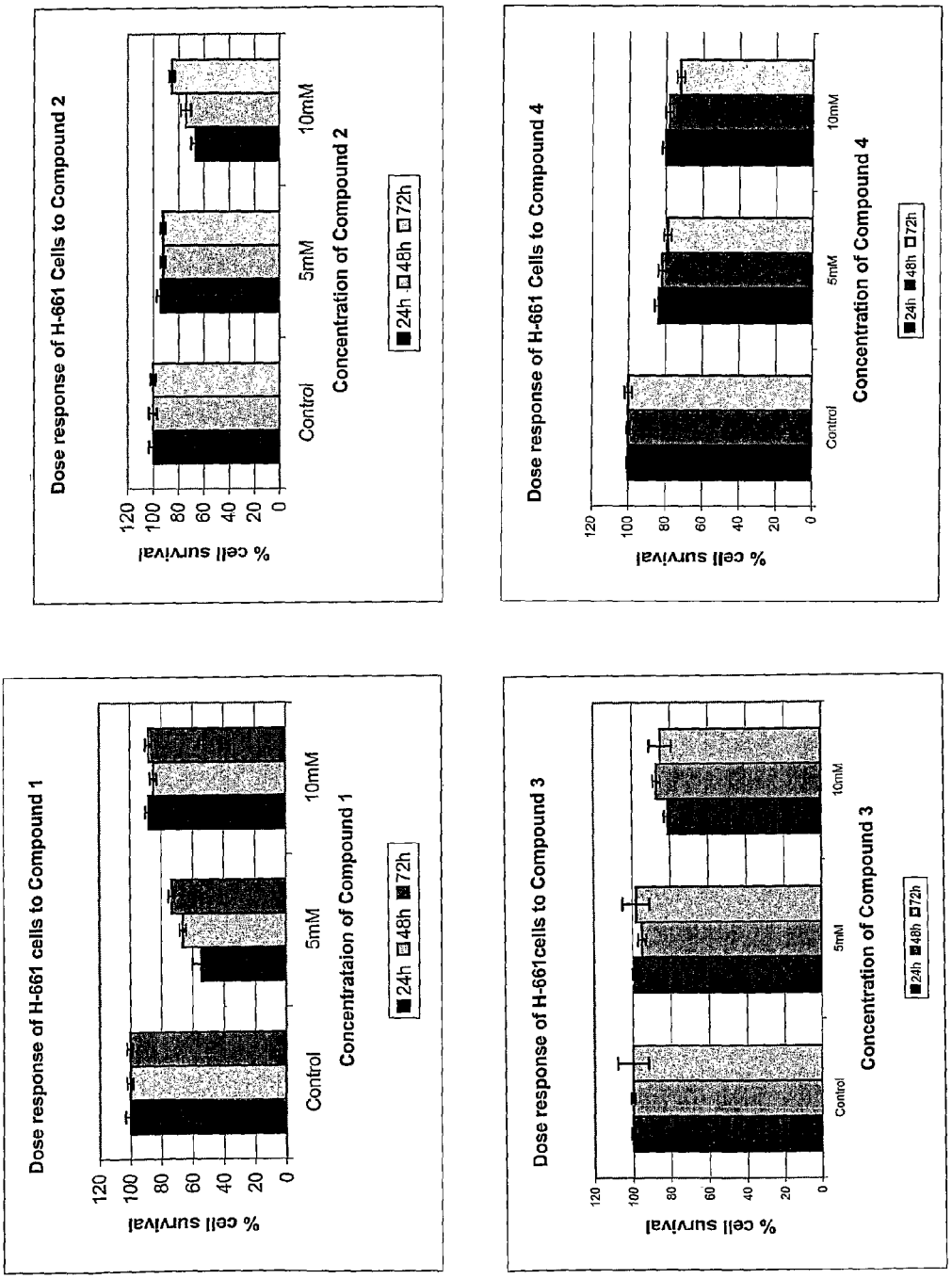
FIG. 8 depicts the effect of compounds 1 to 10 on proliferation of H-661 non-small cell lung cancer cells.
Figure 8:
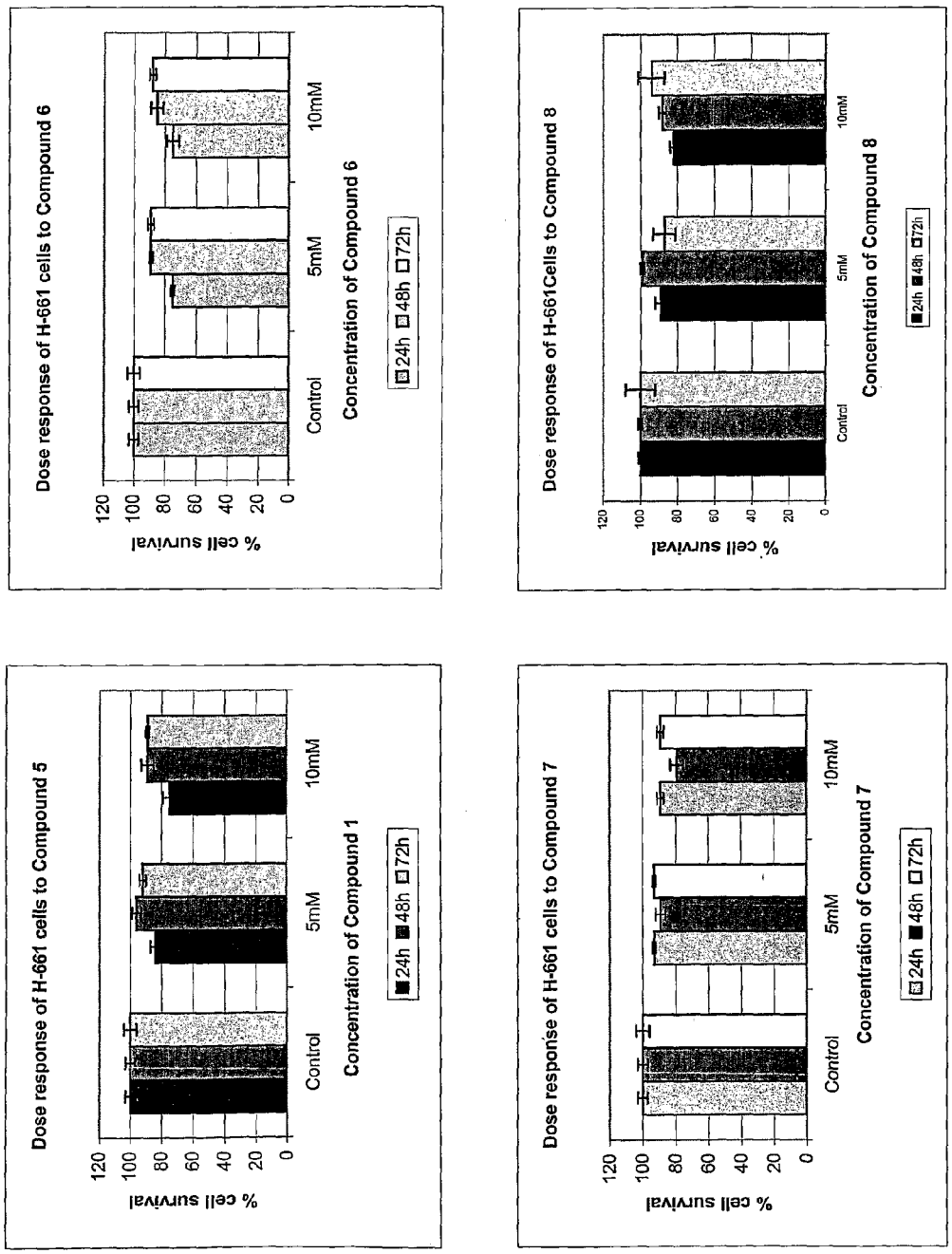
Figure 8:
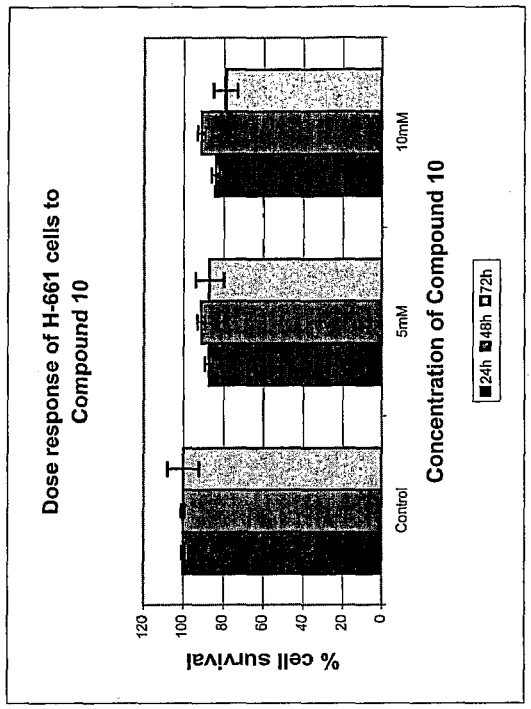
Figure 8:
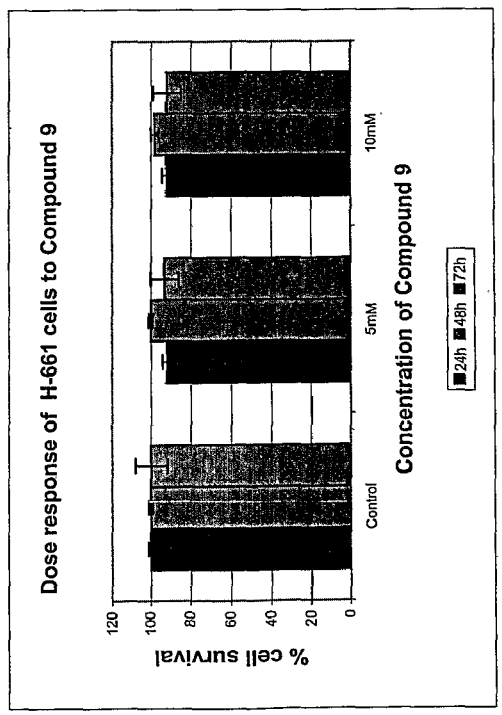
Figure 9:
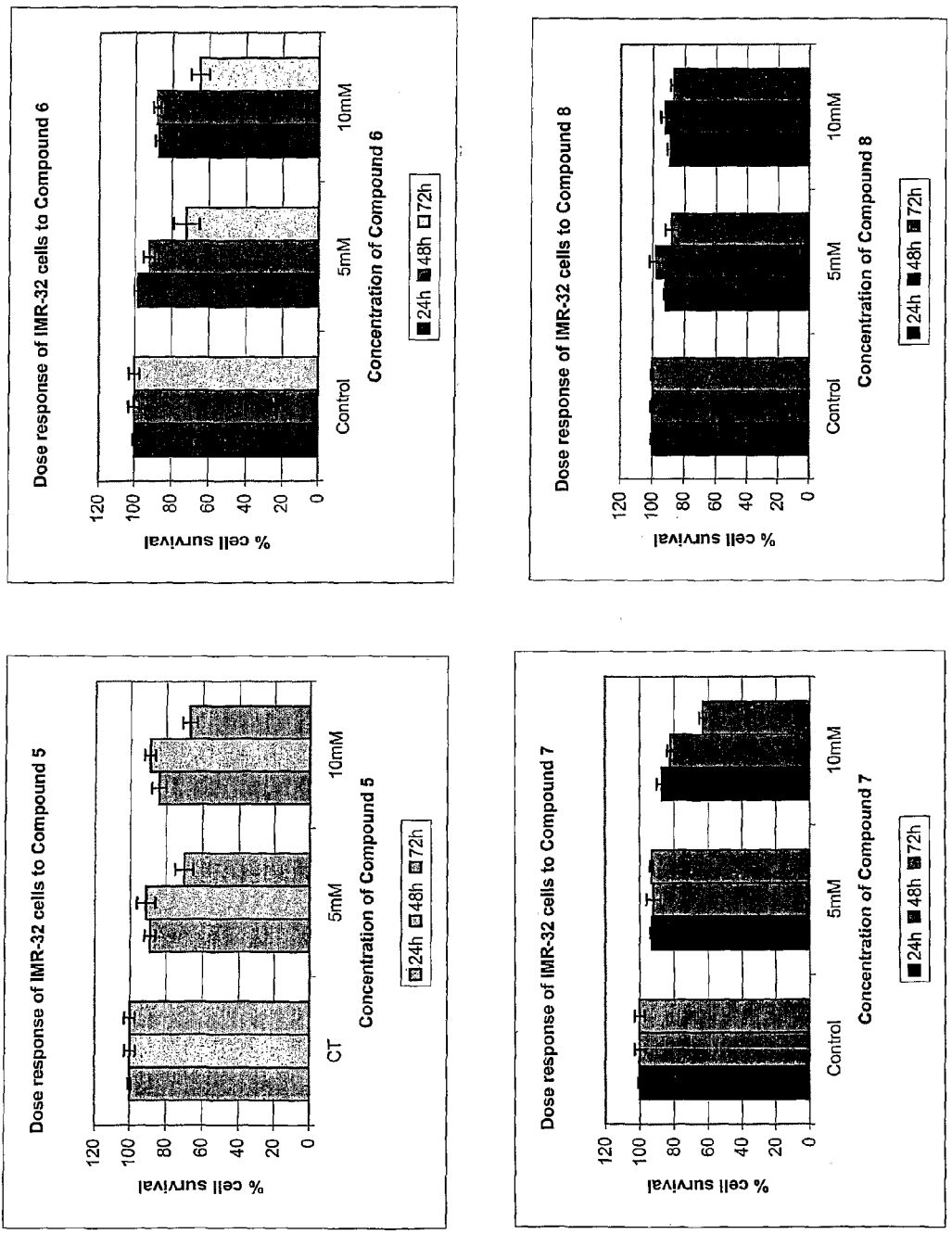
FIG. 9 depicts the effect of compounds 1 to 10 on proliferation of IMR-32 neuroblastoma cells.
Figure 9:
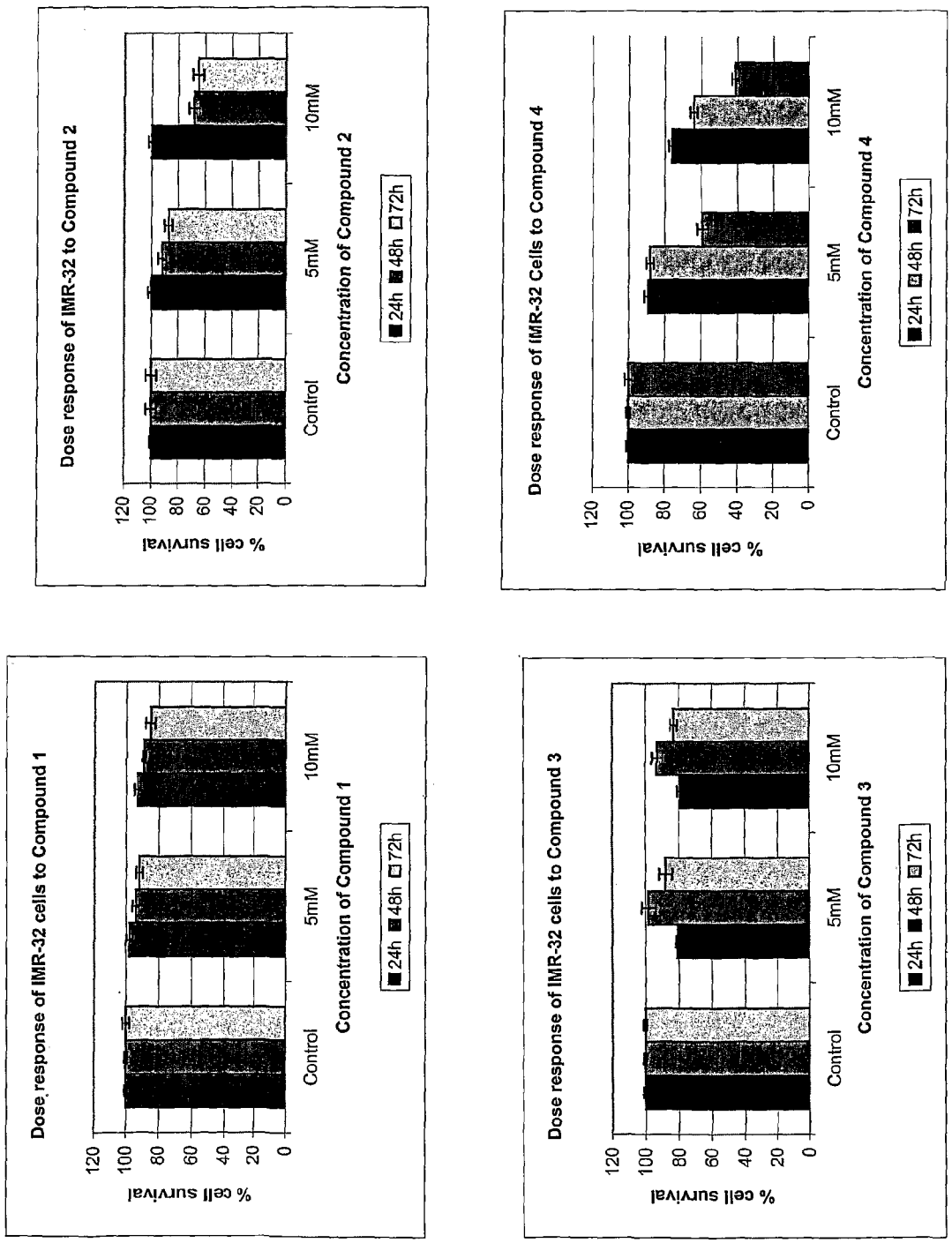
Figure 9:
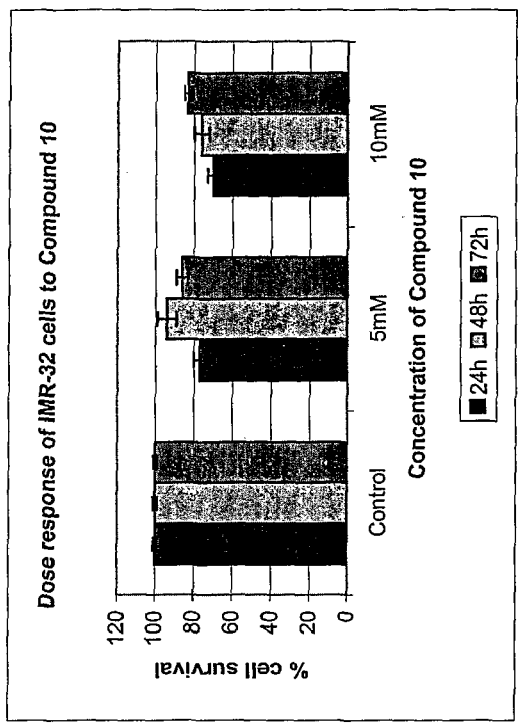
Figure 9:
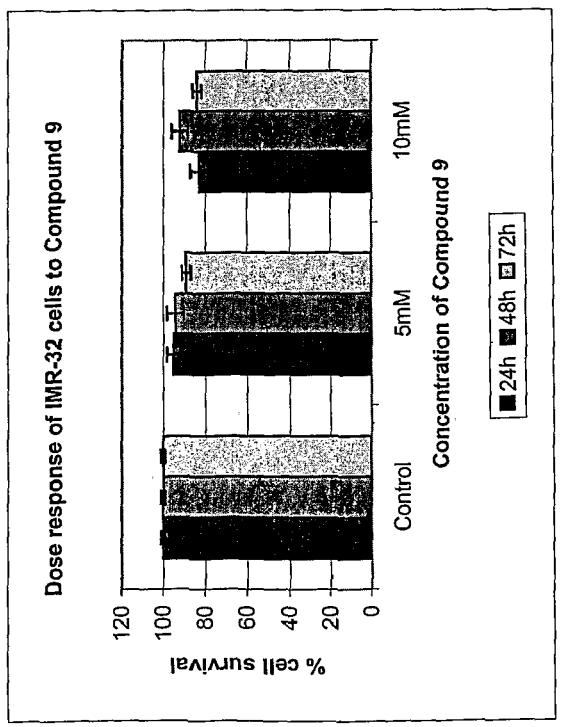
Figure 10:
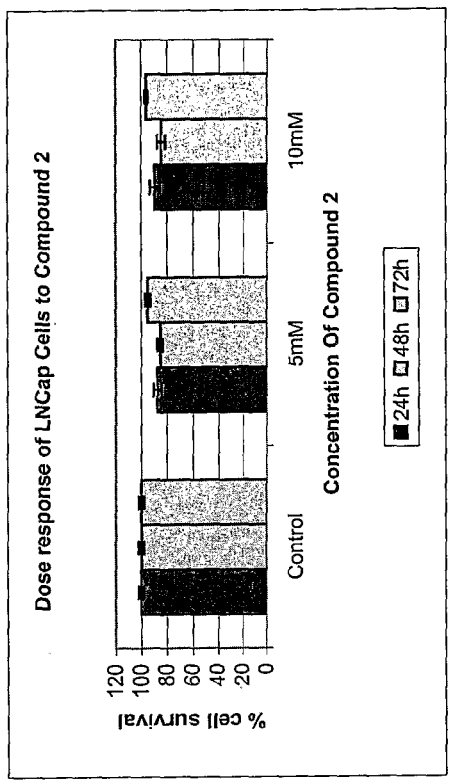
FIG. 10 depicts the effect of compounds 1 to 10 on proliferation of LNCap prostate cancer cells.
Figure 10:
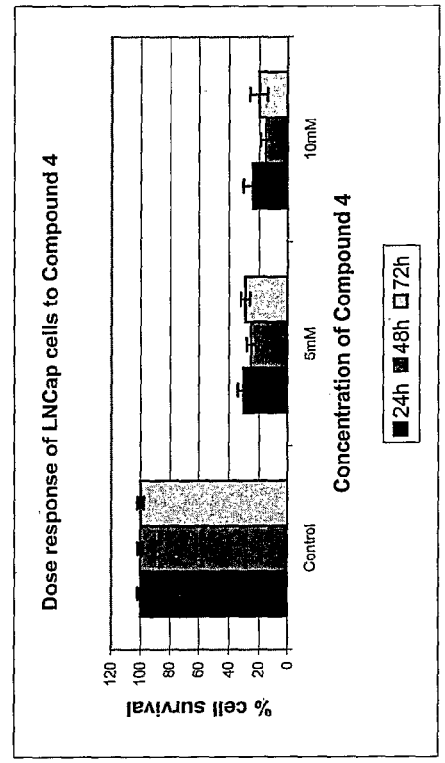
Figure 10:
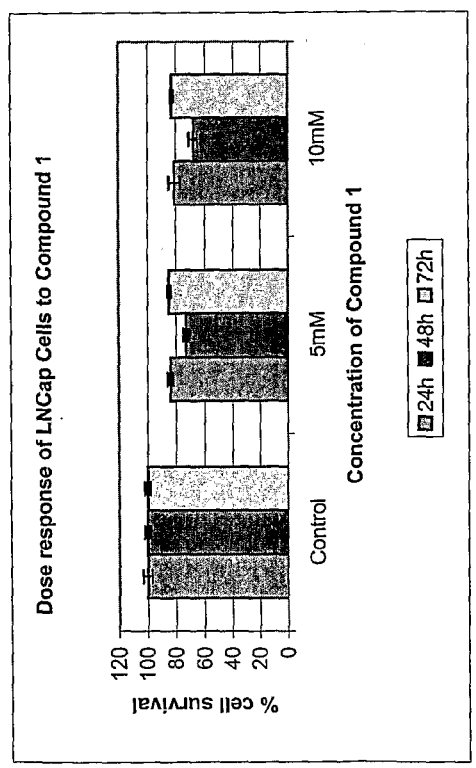
Figure 10:
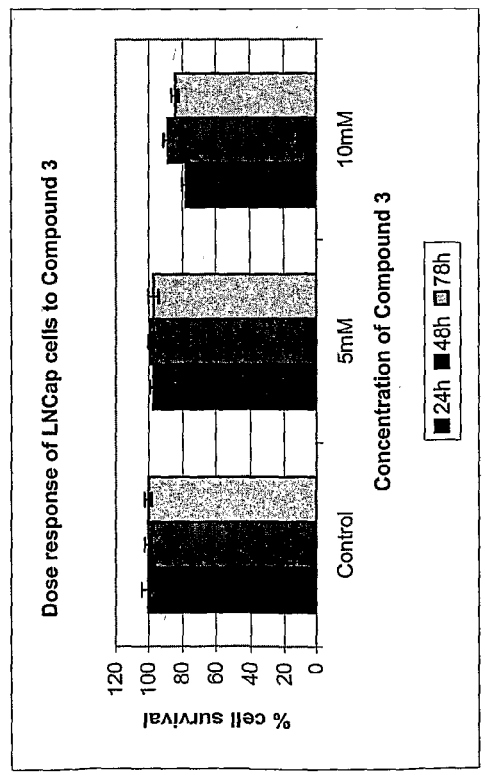
Figure 10:
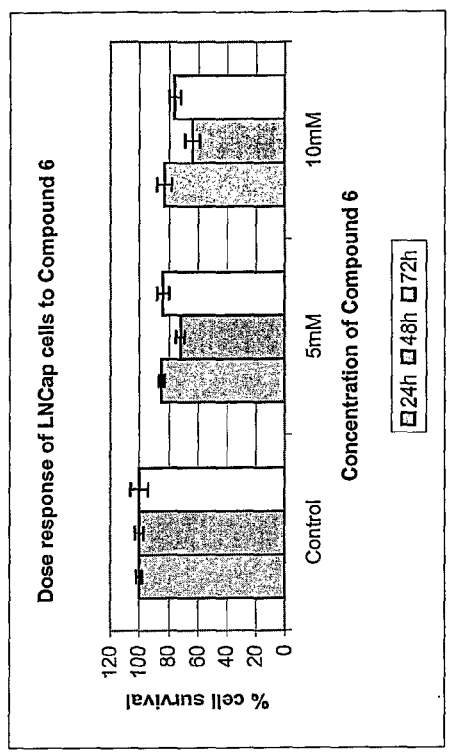
Figure 10:
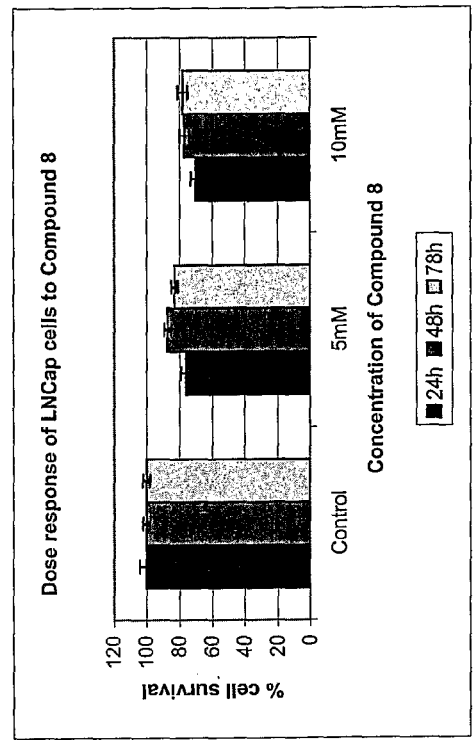
Figure 10:
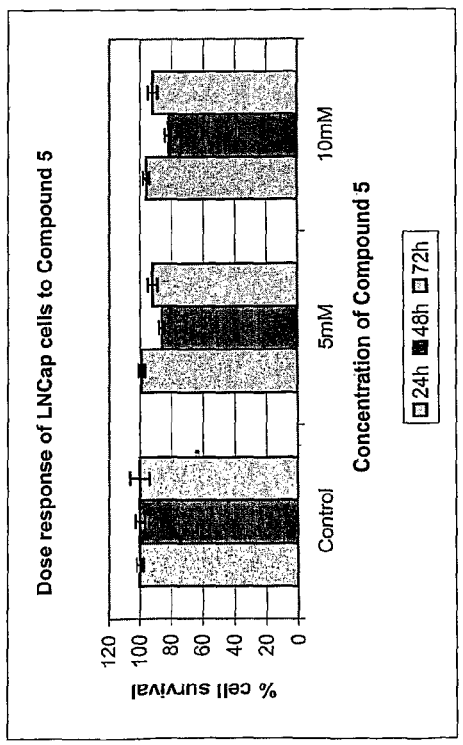
Figure 10:
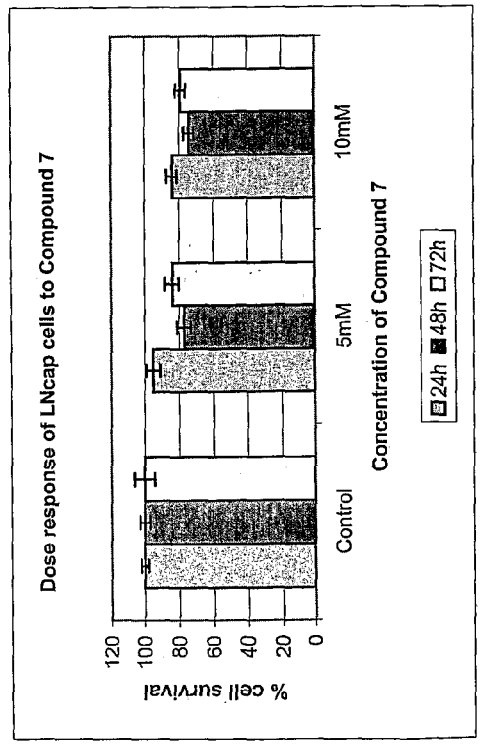
Figure 10:
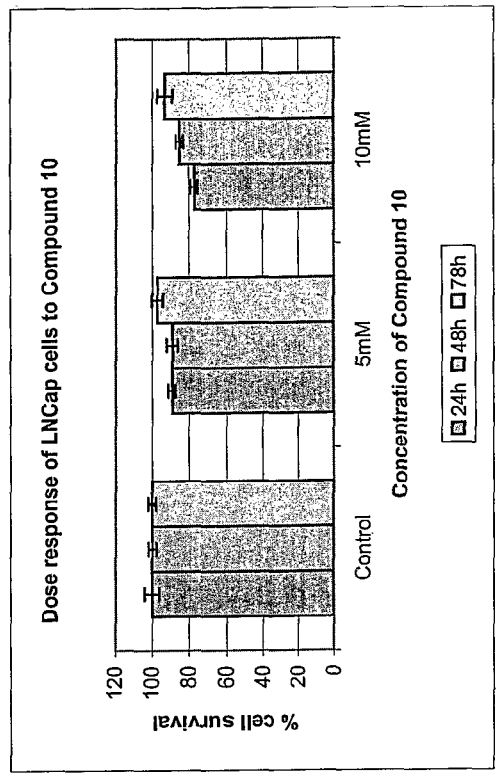
Figure 10:
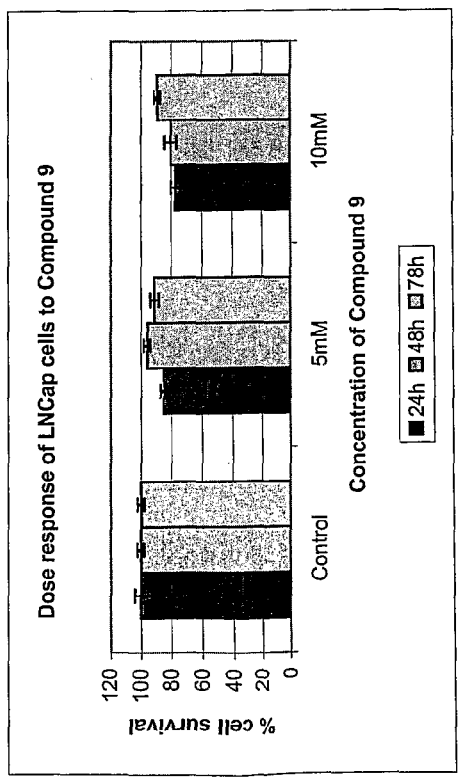
Figure 11:
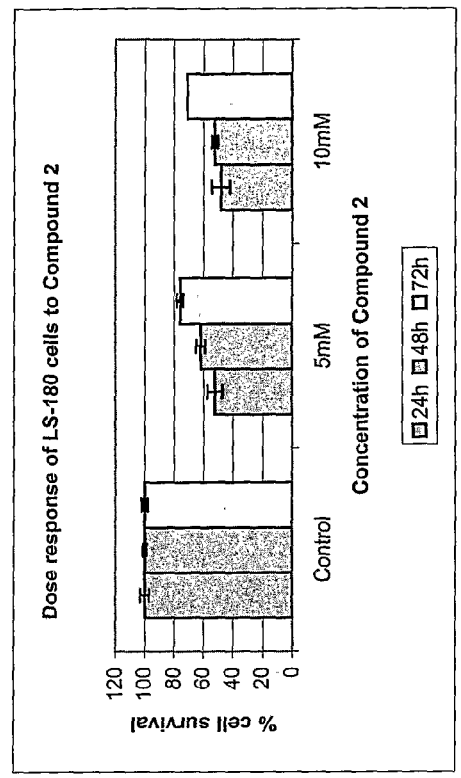
FIG. 11 depicts the effect of compounds 1 to 10 on proliferation of LS-180 colon cancer cells.
Figure 11:
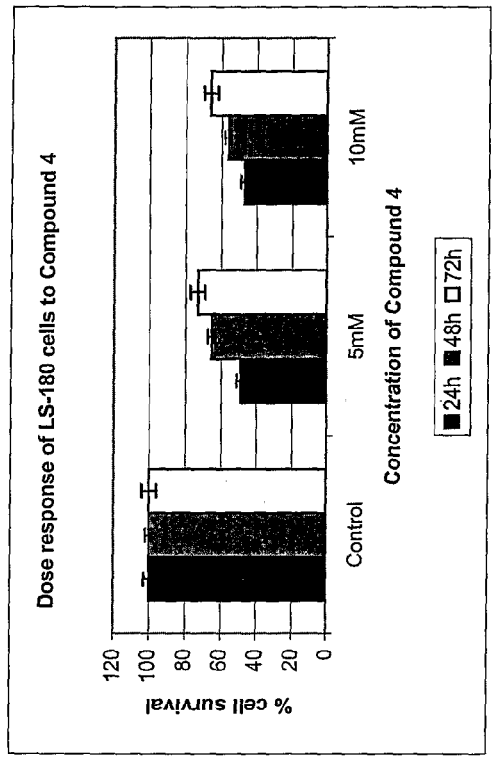
Figure 11:
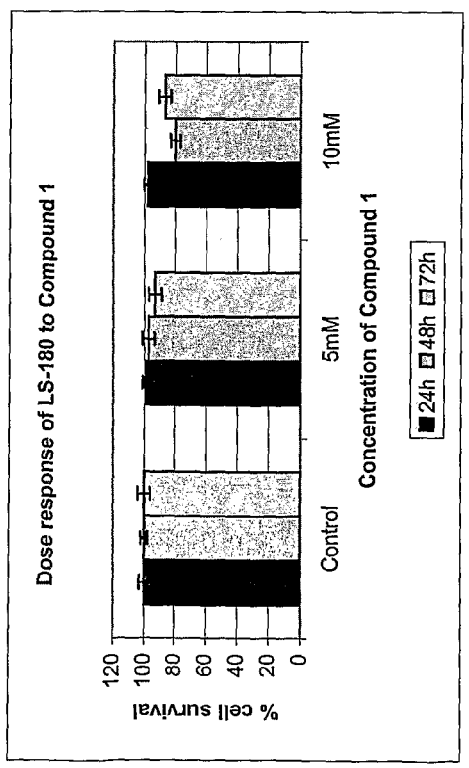
Figure 11:
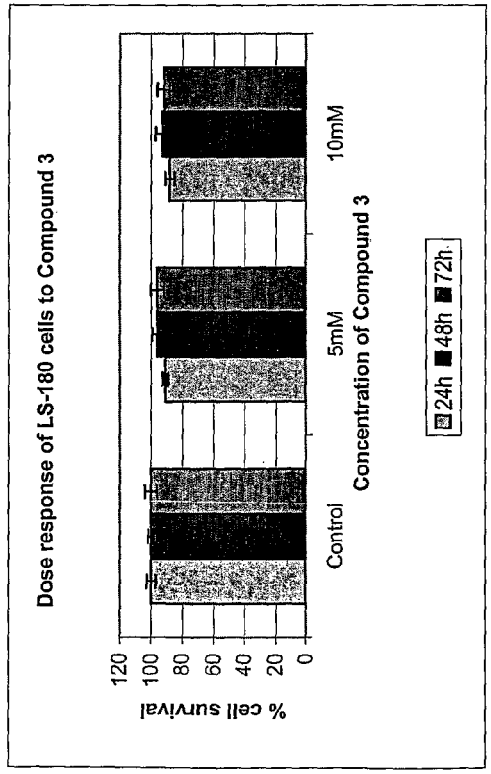
Figure 11:
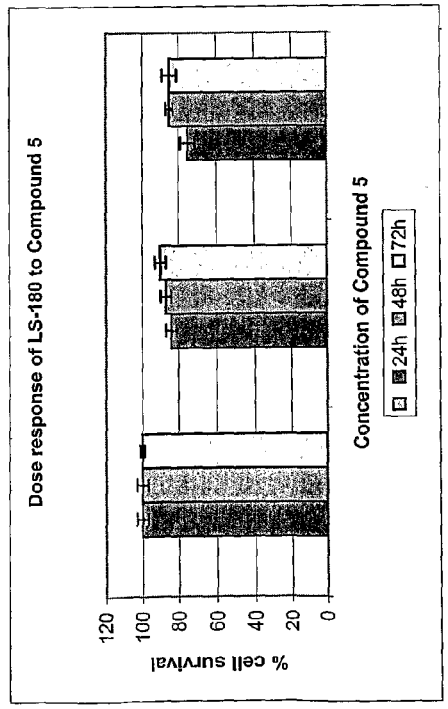
Figure 11:
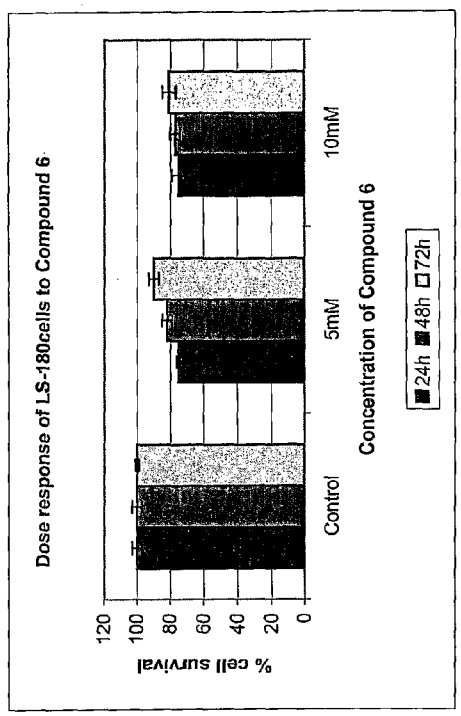
Figure 11:
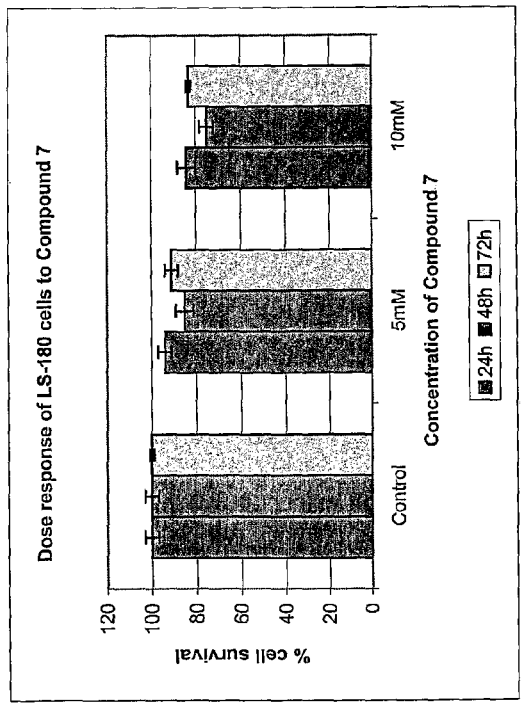
Figure 11:
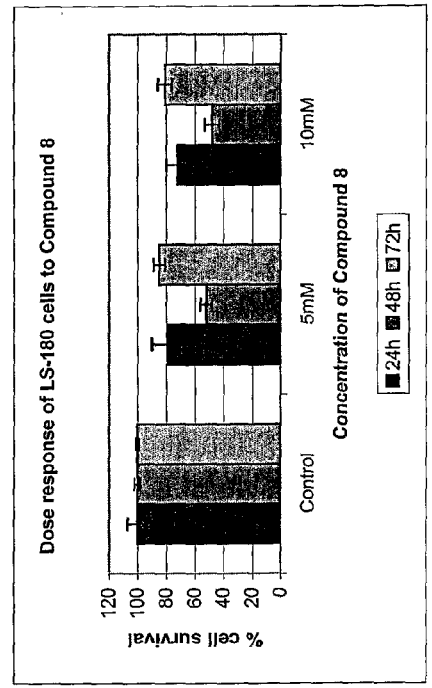
Figure 11:
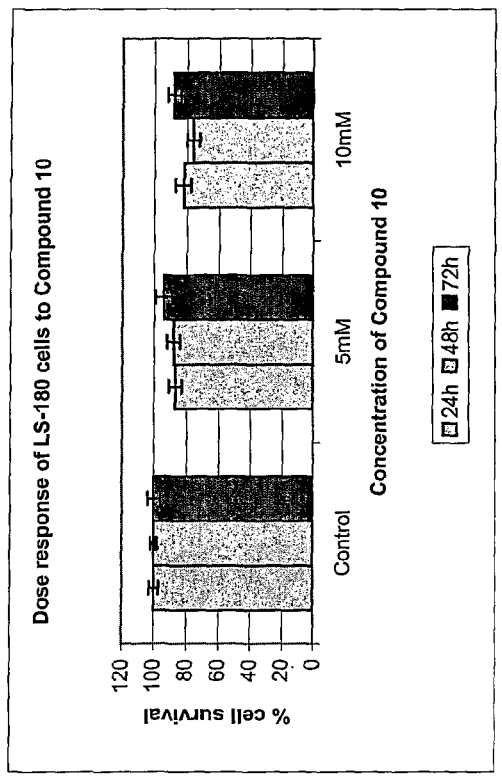
Figure 11:
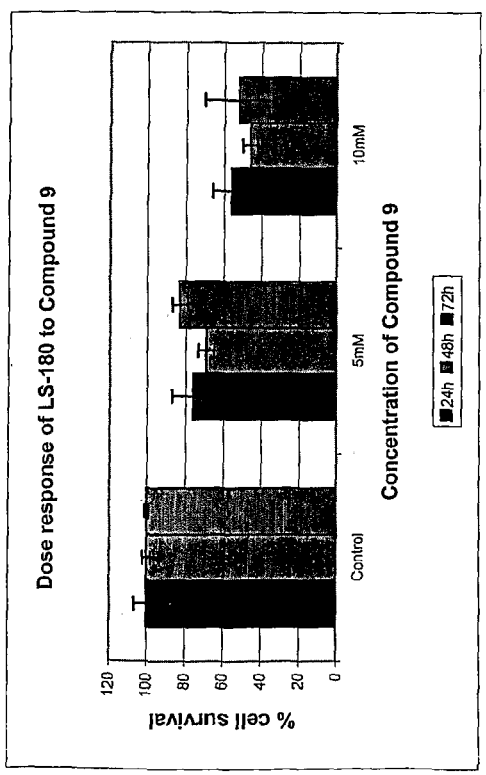
Figure 12:
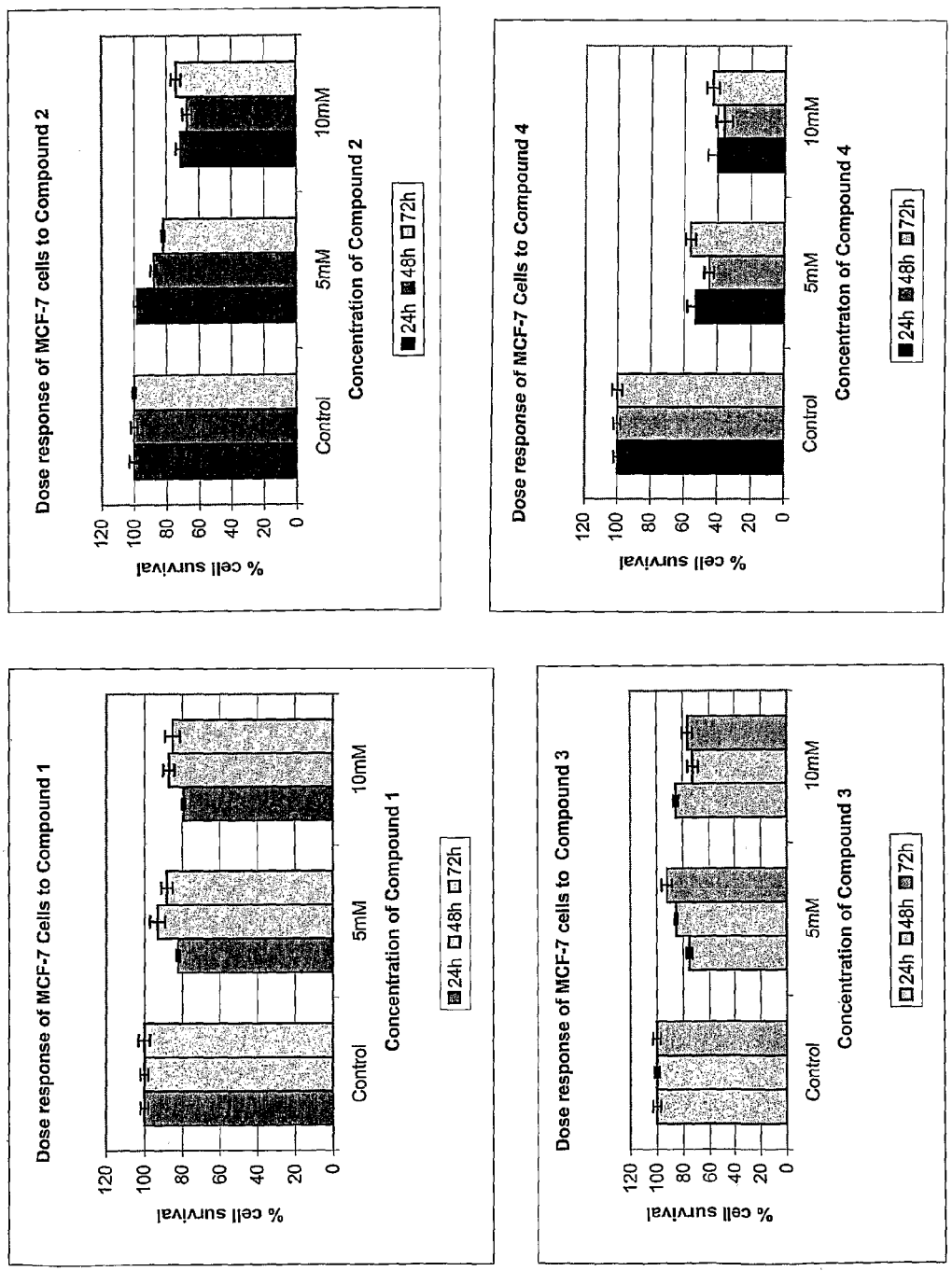
FIG. 12 depicts the effect of compounds 1 to 10 on proliferation of MCF-7 breast cancer cells.
Figure 12:
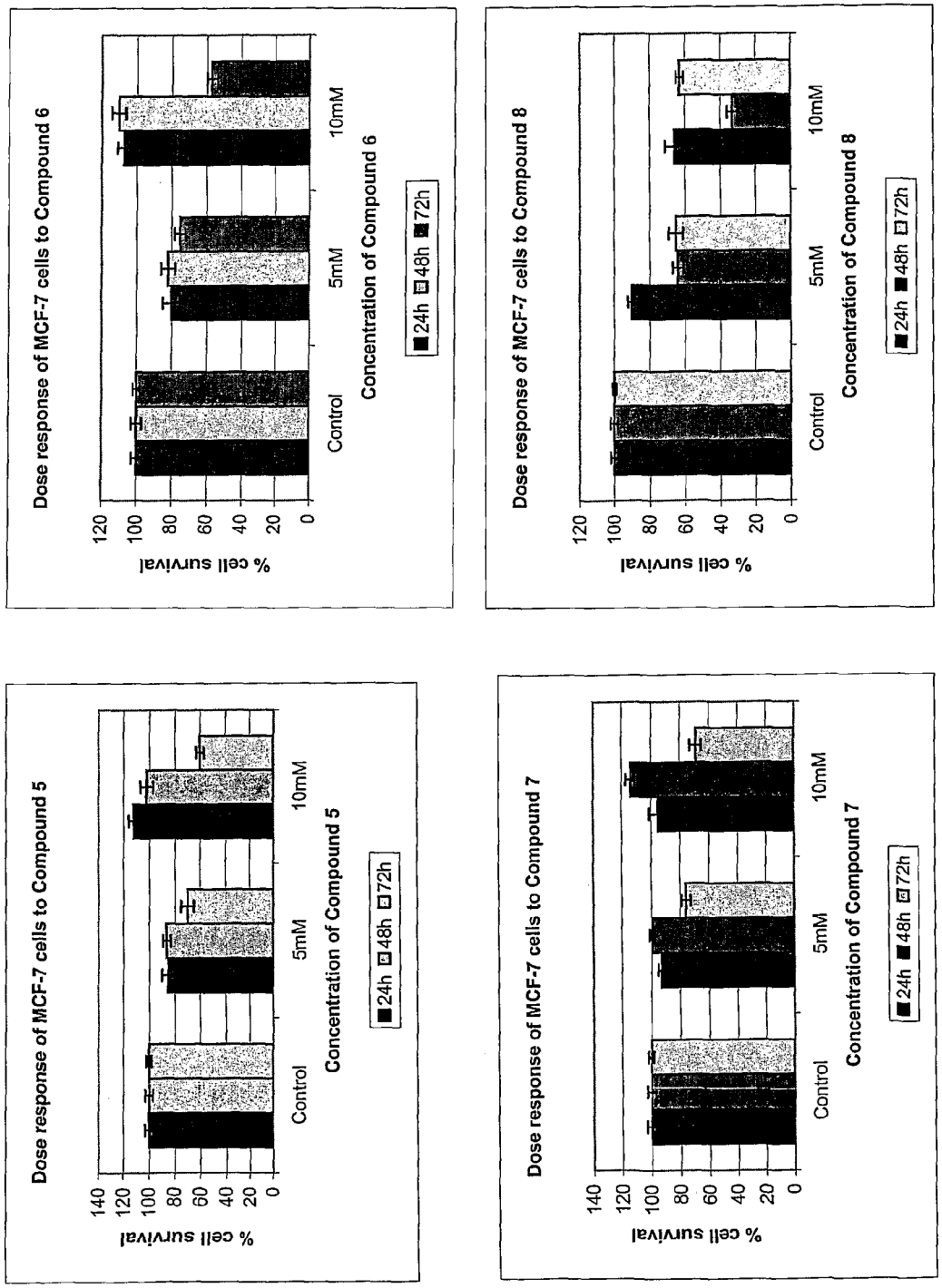
Figure 12:
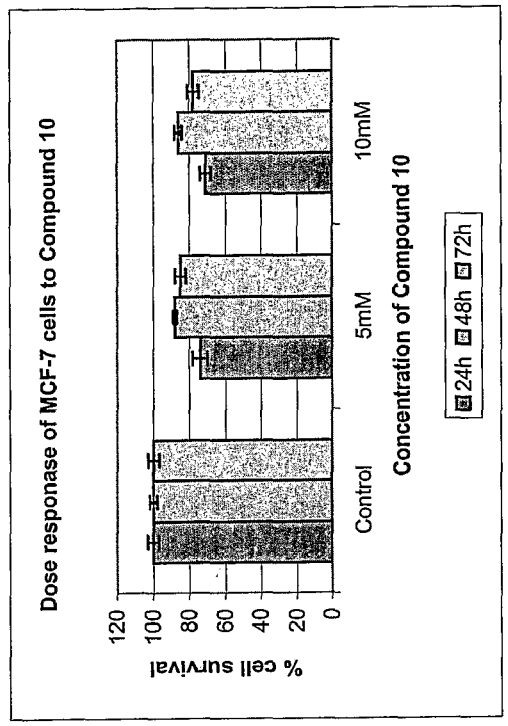
Figure 12:
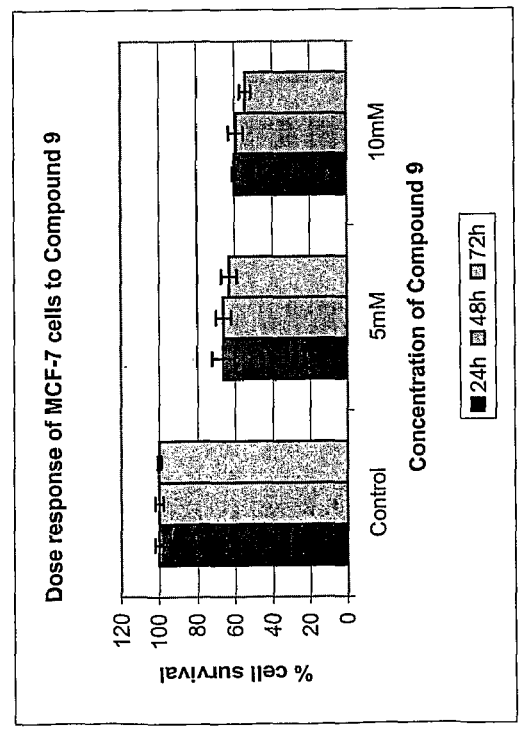
Figure 13:
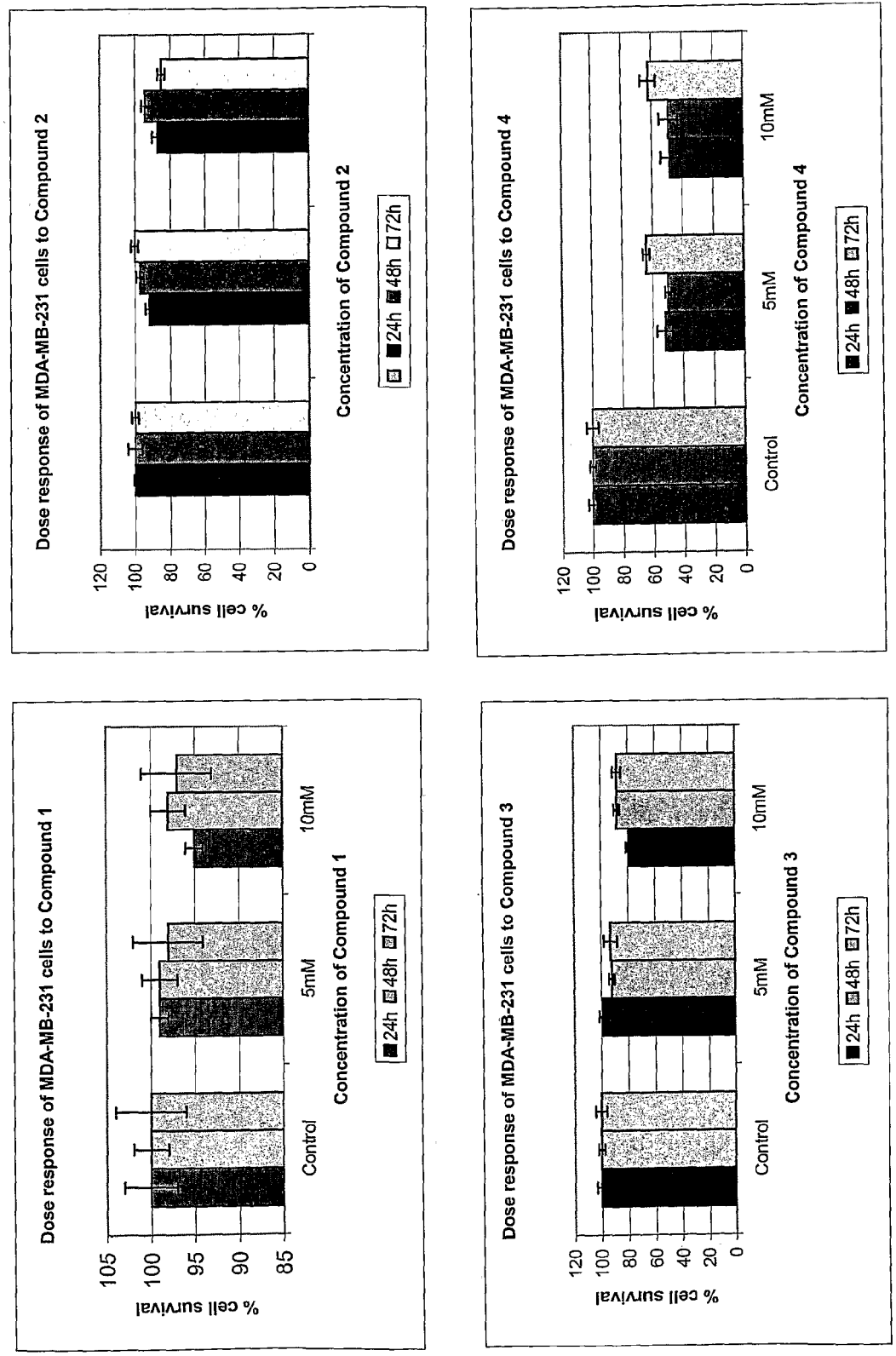
FIG. 13 depicts the effect of compounds 1 to 10 on proliferation of MDA-MB-231 breast cancer cells.
Figure 13:
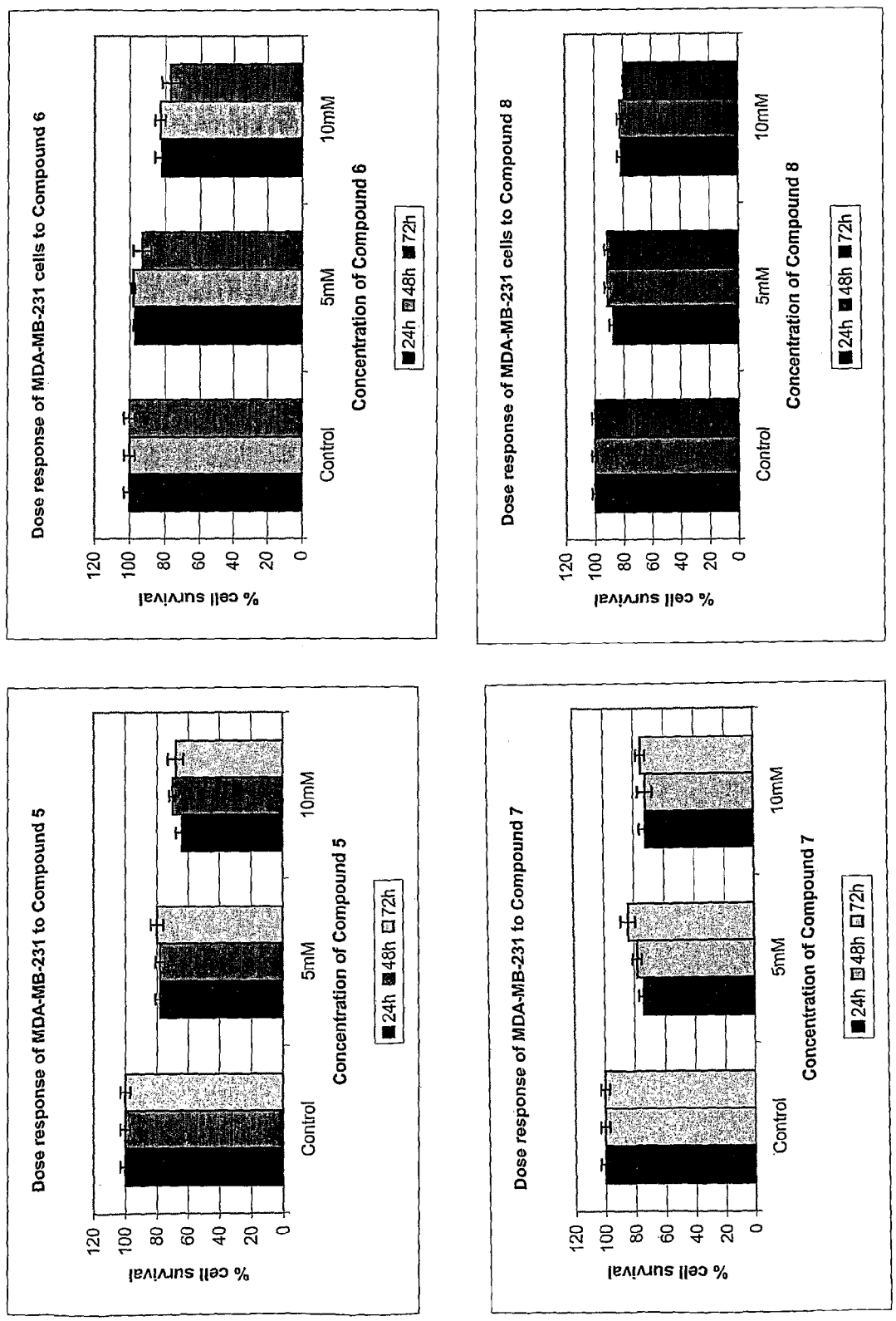
Figure 13:
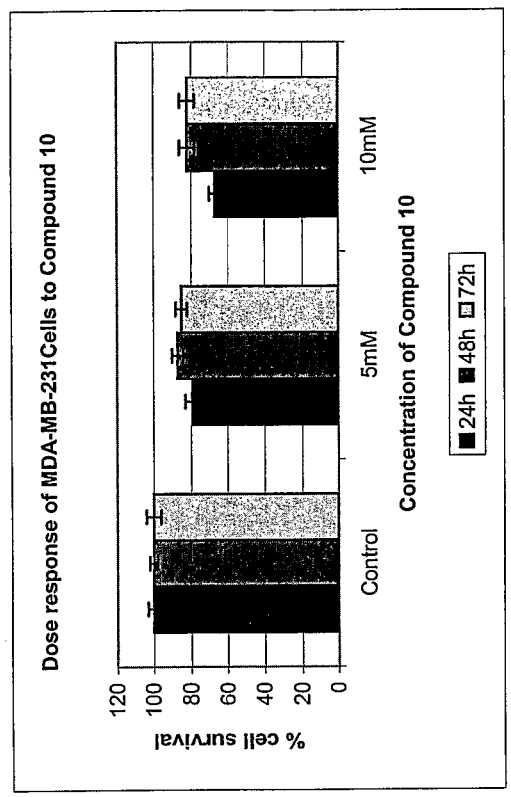
Figure 13:
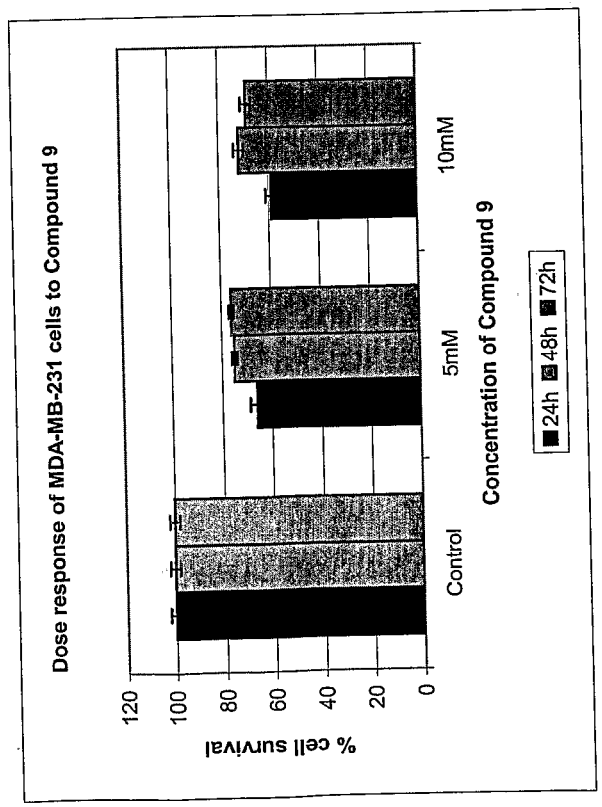
Figure 14:
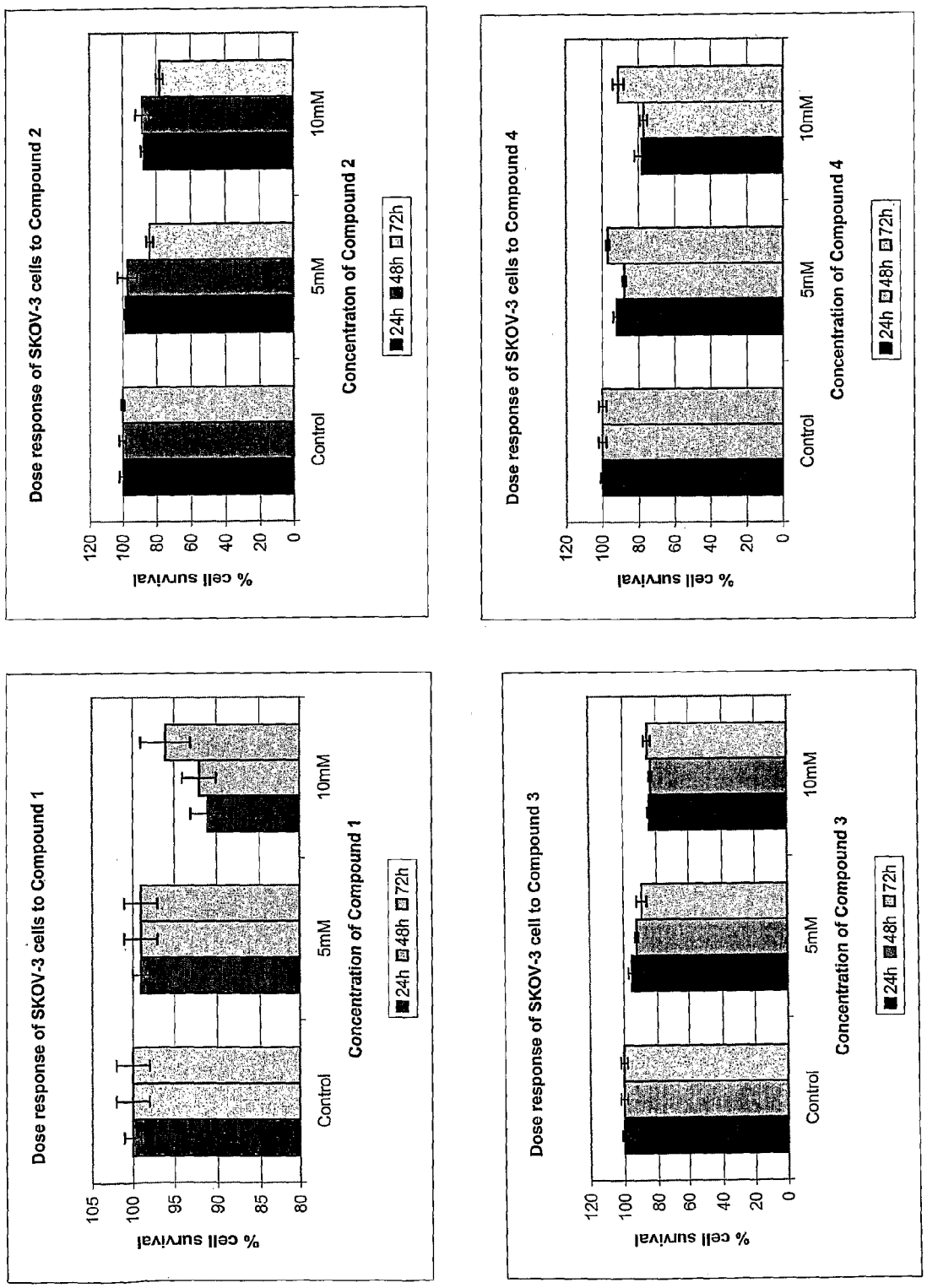
FIG. 14 depicts the effect of compounds 1 to 10 on proliferation of SKOV-3 ovarian cancer cells.
Figure 14:
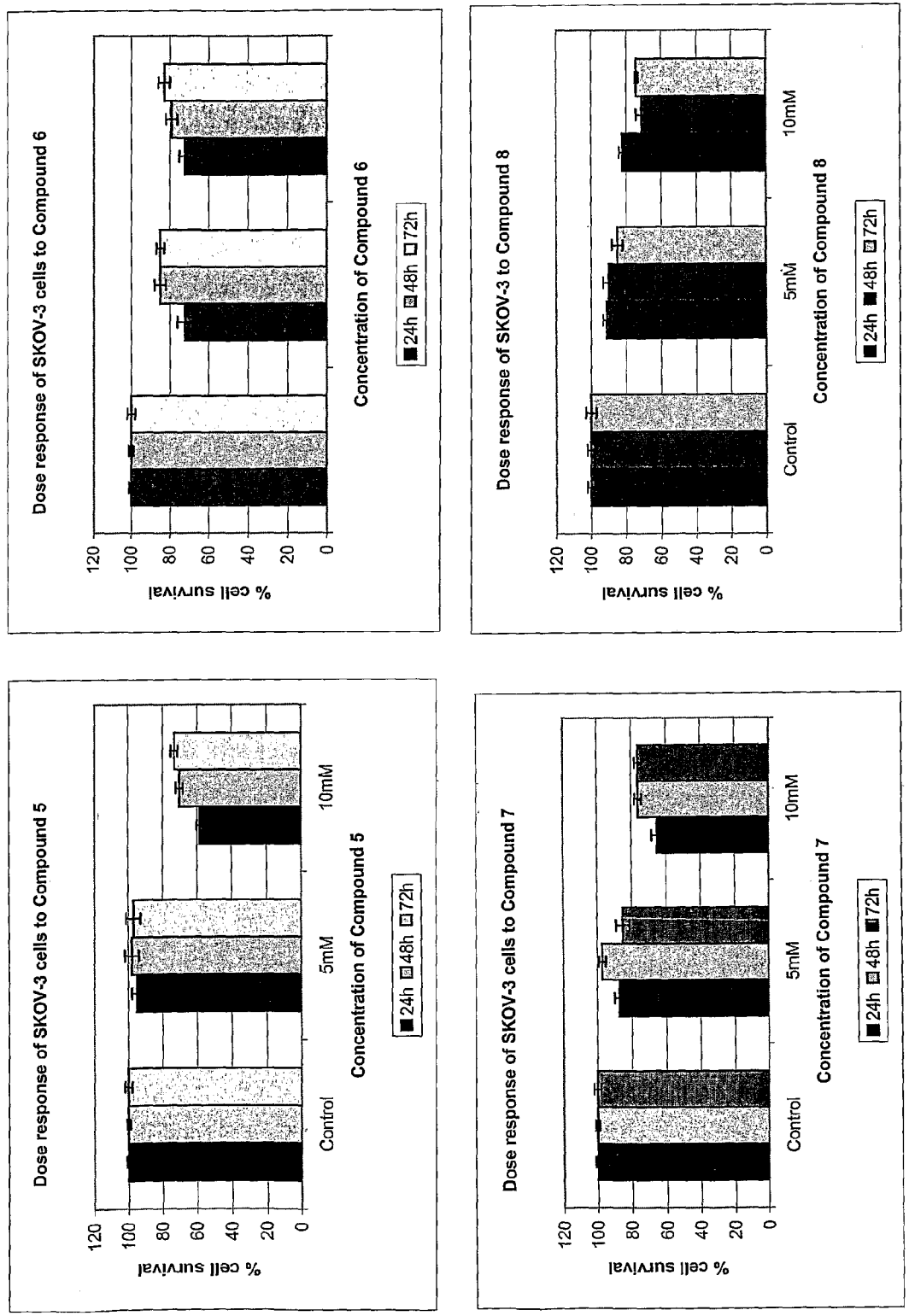
Figure 14:
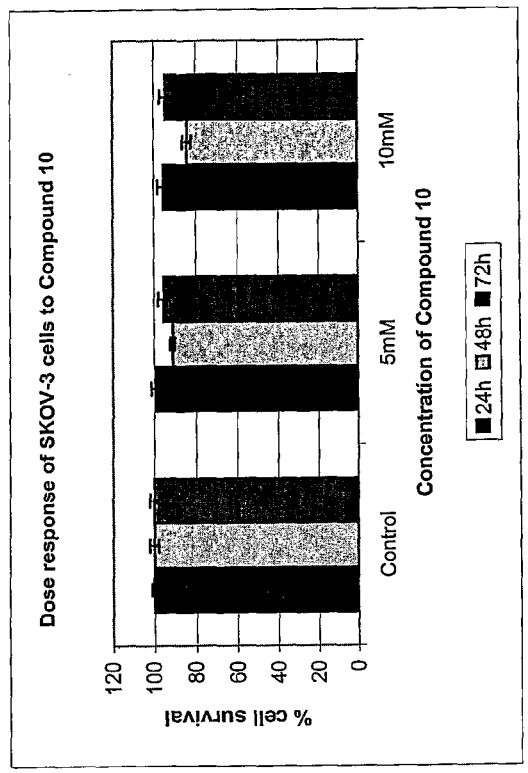
Figure 14:
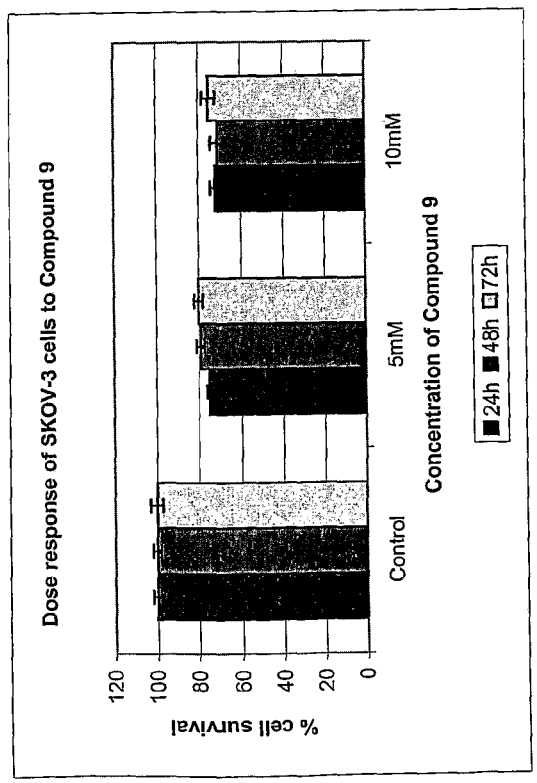
Figure 15:
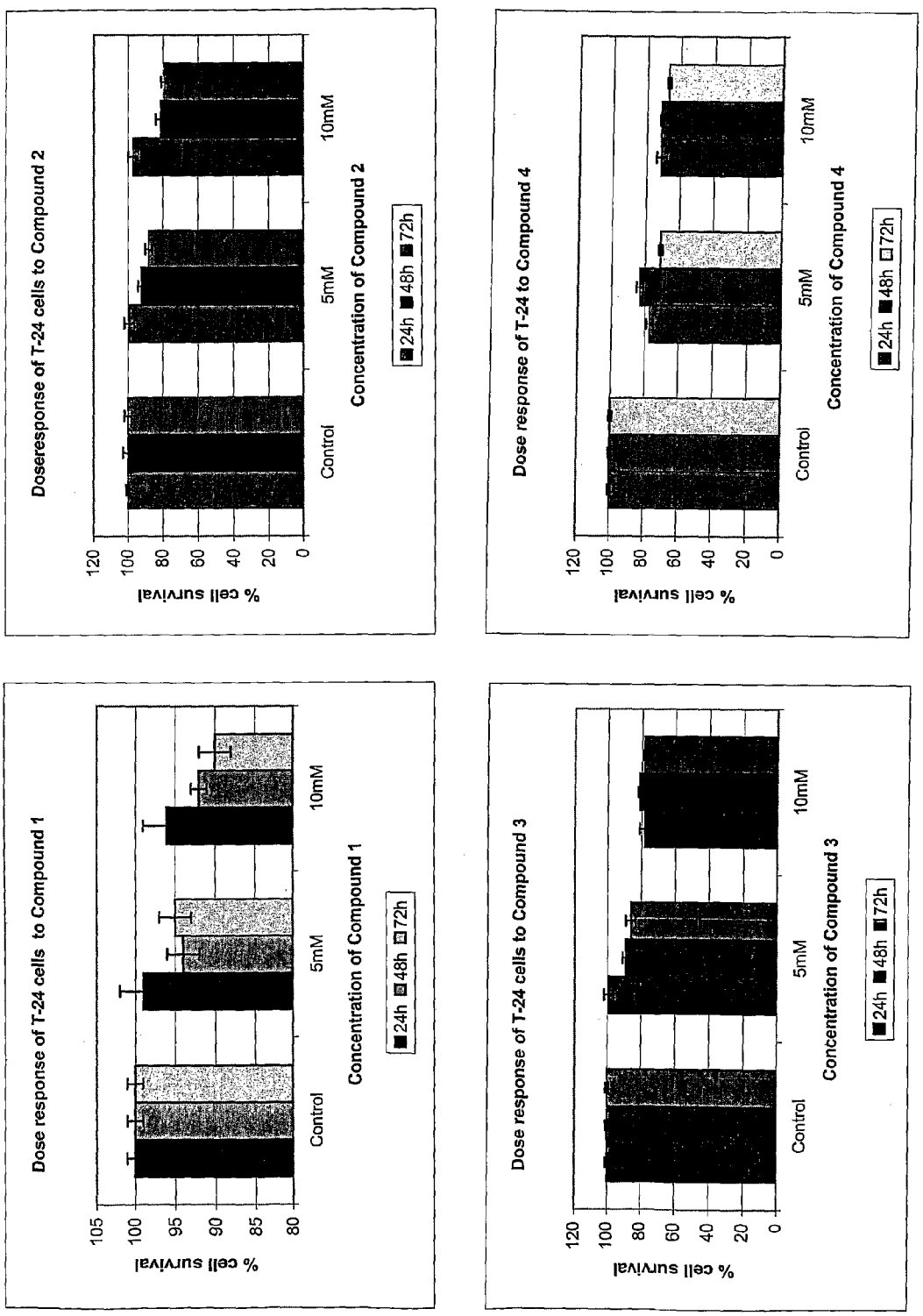
FIG. 15 depicts the effect of compounds 1 to 10 on proliferation of T-24 bladder cancer cells.
Figure 15:
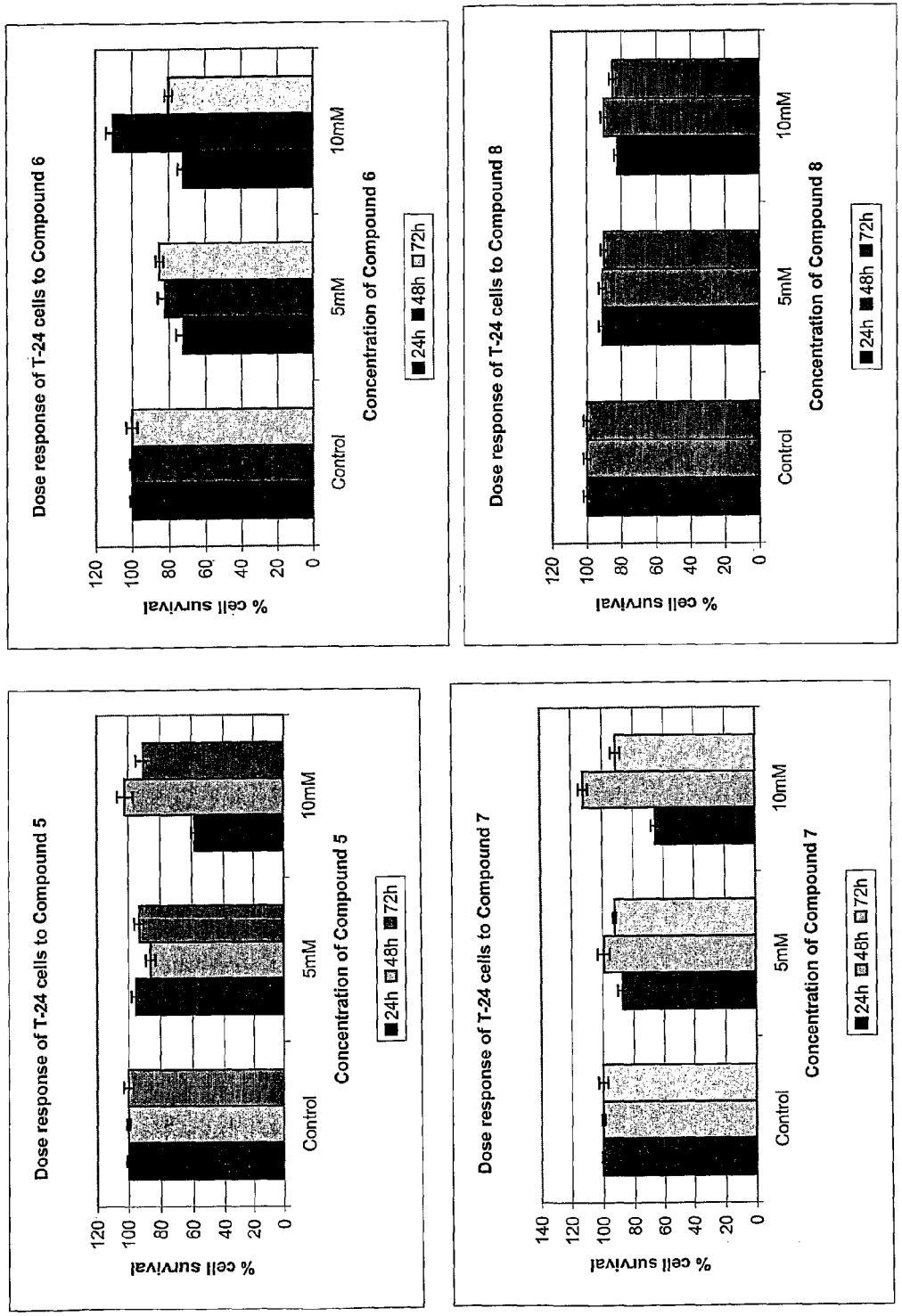
Figure 15:
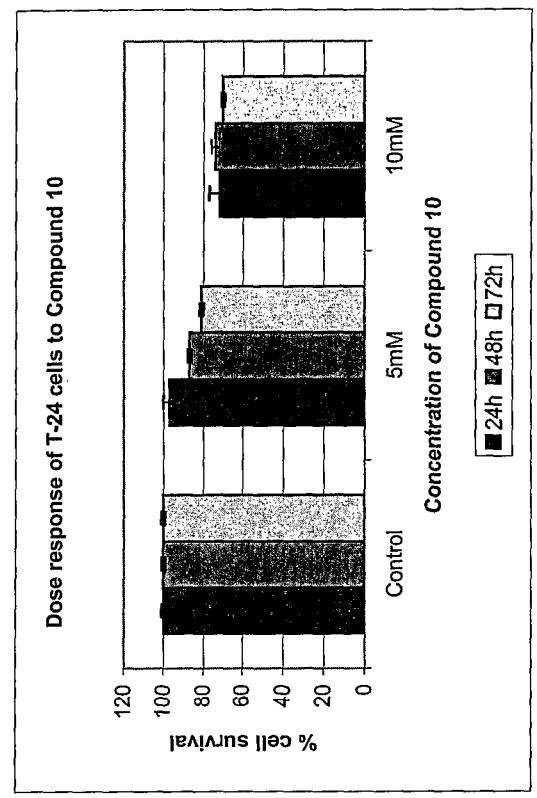
Figure 15:
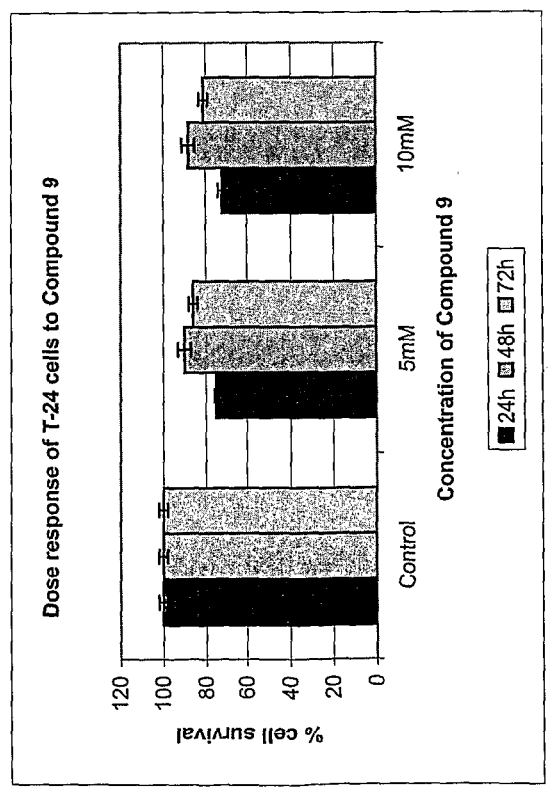
Figure 16:
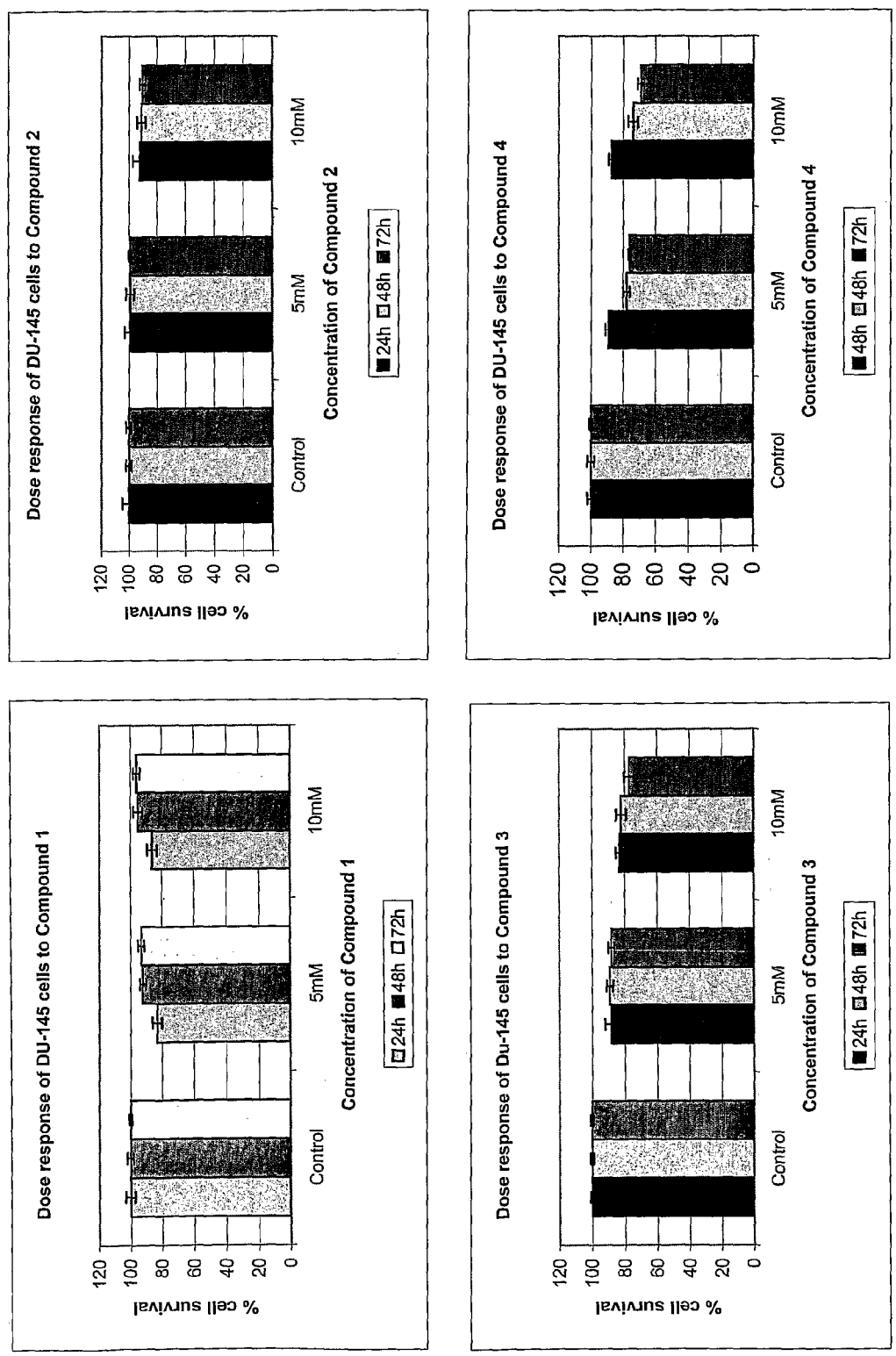
FIG. 16 depicts the effect of compounds 1 to 10 on proliferation of DU-145 prostate cancer cells.
Figure 16:
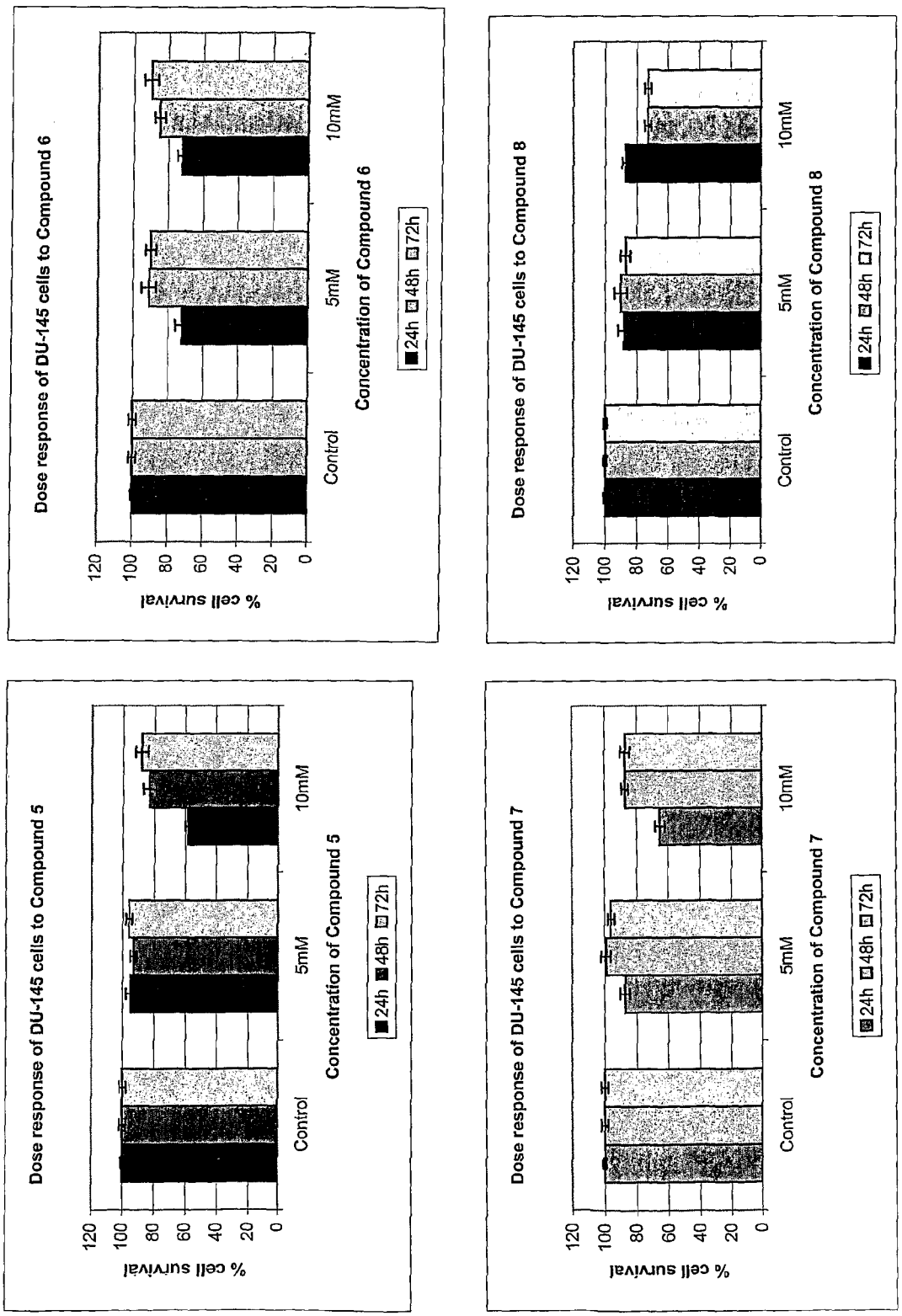
Figure 16:
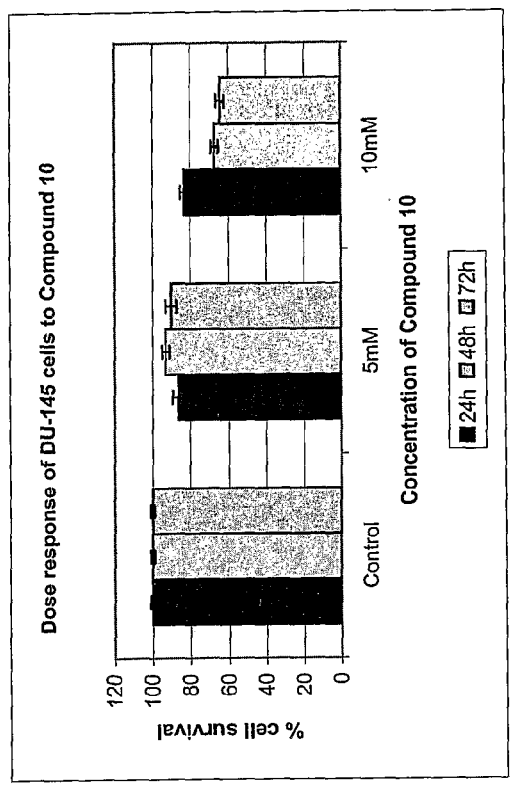
Figure 16:
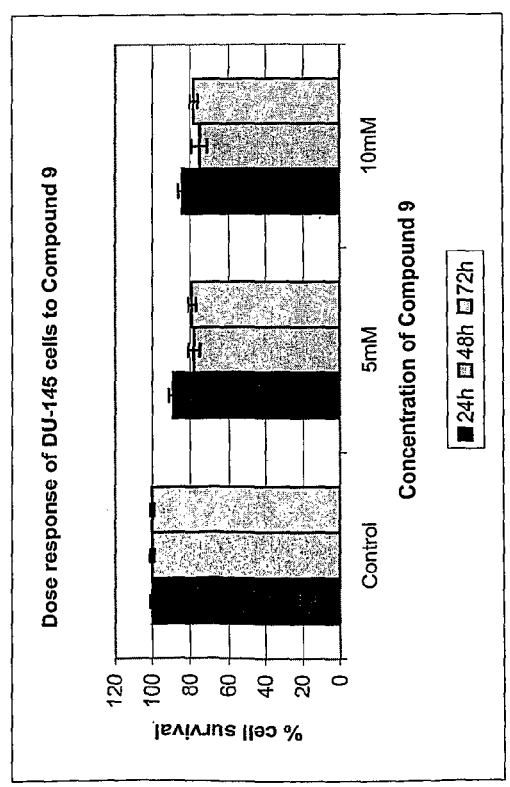

The results at 24 h, 48 h and 72 h are summarised in FIG. 7 (U-251); FIG. 8 (H-661); FIG. 9 (IMR-32); FIG. 10 (LN-Cap); FIG. 11 (LS-80); FIG. 12 (MCF-7); FIG. 13 (MDA-MB-231); FIG. 14 (SKOV-3); FIG. 15 (T-24) and FIG. 16 (DU-145).

All compounds were able to inhibit at least two of the tested cancer cell line by 15% or more at a concentration of 5 mM. While there appears to be a certain amount of specificity of the compounds toward various cell lines, interestingly, the colon cancer cell line LS-180 was very sensitive to cell death induced by the majority of compounds and notably by compounds 5, 6, 7, 4, 9 and 2. Both compounds 4 and 2 exerted a powerful short-term activity on this colon cancer cell line followed by moderate re-growth. The most striking effect of the compounds is on cell death over the first 24 h following incorporation of the compounds. In addition, the stability of the compounds is at least of 72 h based on the general maintenance of the growth at steady state or decreasing proliferation.

Example 15

Effect of Compounds 1 to 10 on Apoptosis

Short-term cell death resulting from the internalisation of compounds 1 to 10 is illustrated in Tables 13 and 14 above. DNA laddering could not, however, be clearly observed as DNA extracts showed up as smears on the gels. Accordingly, the effect of a representative compound, compound 3, was analysed as a dose response in two cancer cell lines in which the compound did not show any short term cell death, MDA-MB-231 breast cancer cell line and NCI H1661 non-small cell lung cancer cell line, using Hoechst reagent to stain the nuclei. Cells were treated with compound 3 at concentrations of 50, 250 and 500 µM. Hoechst staining was performed as follows. Cells were washed 1× with phosphate-buffered saline (PBS) containing $Ca^{2+}$ and $Mg^{2+}$. Cells were then fixed with 1% paraformaldehyde solution prepared in PBS containing $Ca^{2+}$ and $Mg^{2+}$ for 20 min at room temperature and washed 3× with PBS containing $Ca^{2+}$ and $Mg^{2+}$. Cells were stained with 5 µg/mL Hoechst 33258 in PBS for 20 minutes to detect chromatin packing, a marker of apoptosis. Finally the cells were washed 3× with PBS. Images were collected on a Nikon Olympus Microscope using IMT2-DMV filter at an Excitation 405 nm and emission greater than 455 nm and analyzed on Image Pro Software.

Figure 17:
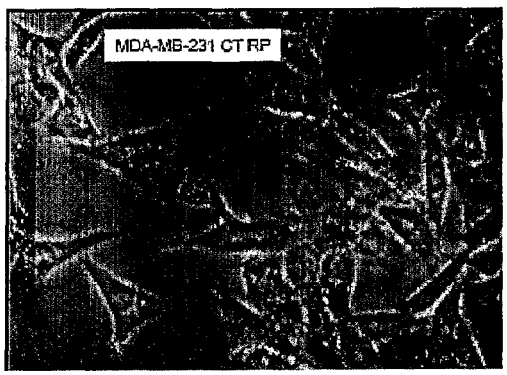
FIG. 17 depicts the effect of compound 3 on apoptosis in MDA-MB-231 breast cancer cells; left hand panels (A, C, E and G) show reverse phase and right hand panels (B, D, F and H) show the nuclei stained with Hoechst reagent.
Figure 17:
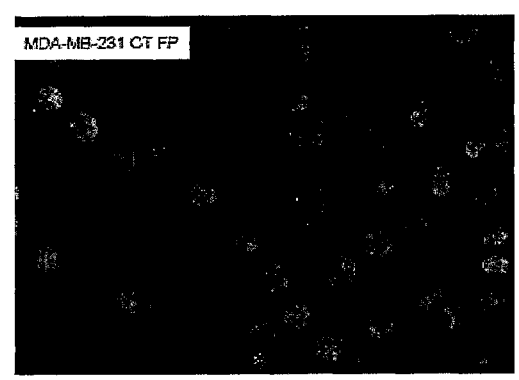
Figure 17:
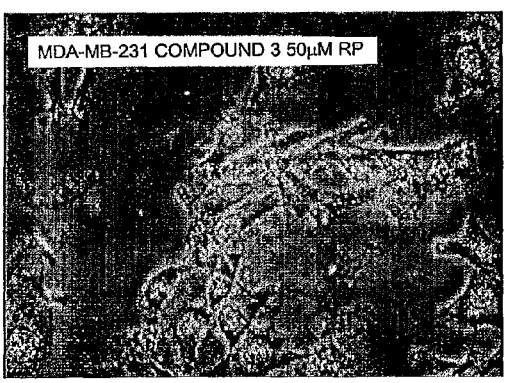
Figure 17:
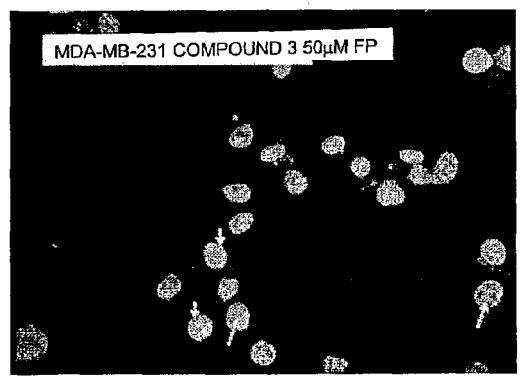
Figure 17:
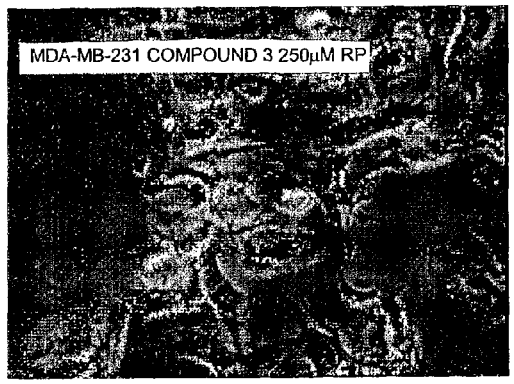
Figure 17:
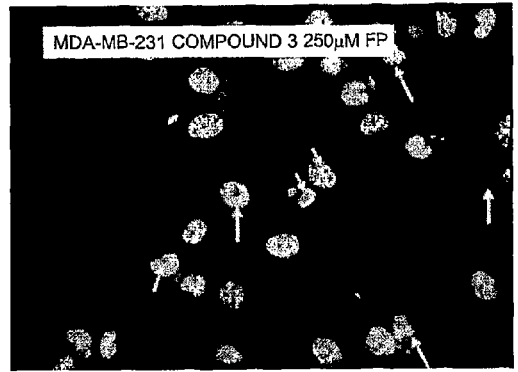
Figure 17:
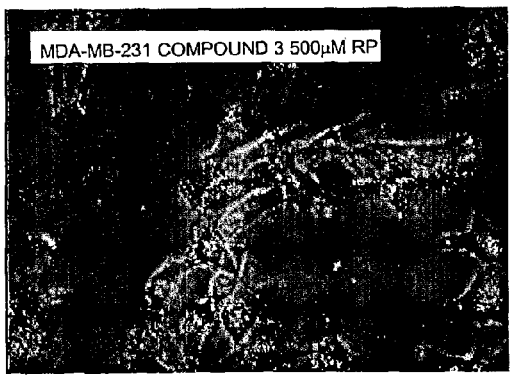
Figure 17:
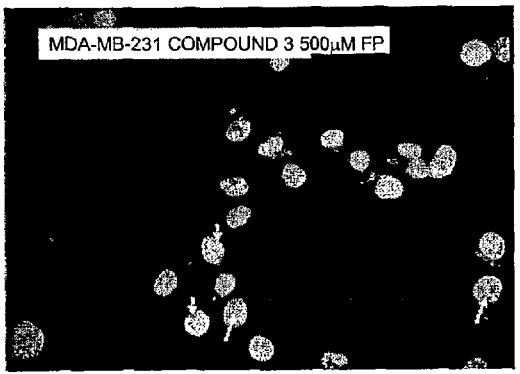
Figure 18:
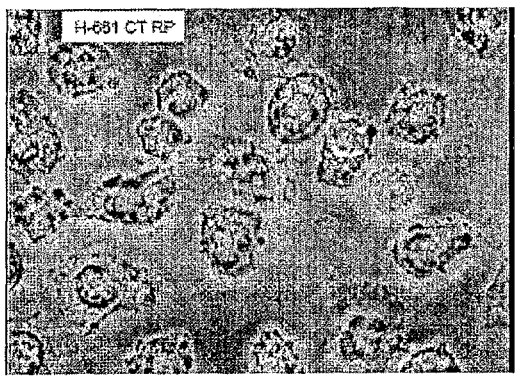
FIG. 18 depicts the effect of compound 3 on apoptosis in H-661 non-small cell lung cancer cells; left hand panels (A, C, E and G) show reverse phase and right hand panels (B, D, F and H) show the nuclei stained with Hoechst reagent.
Figure 18:
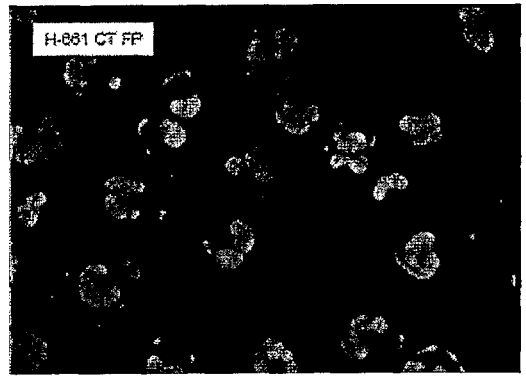
Figure 18:
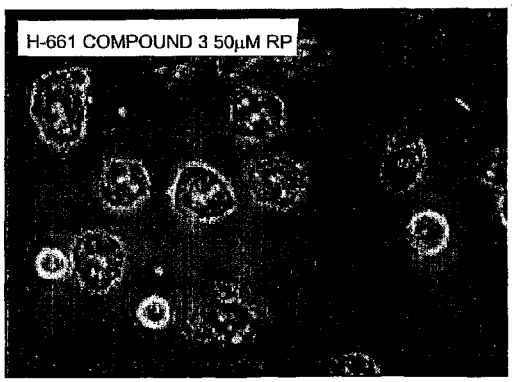
Figure 18:
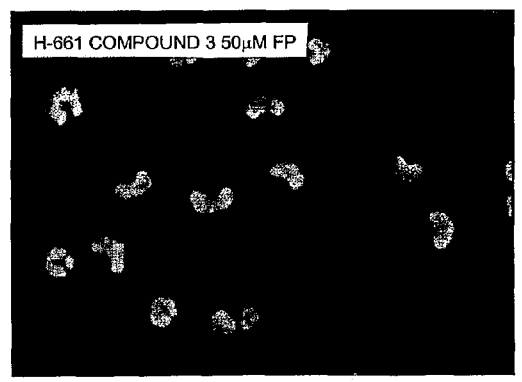
Figure 18:
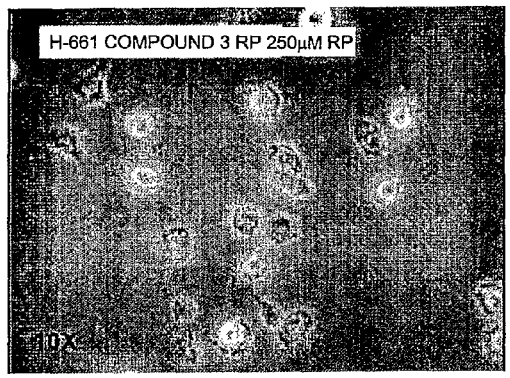
Figure 18:
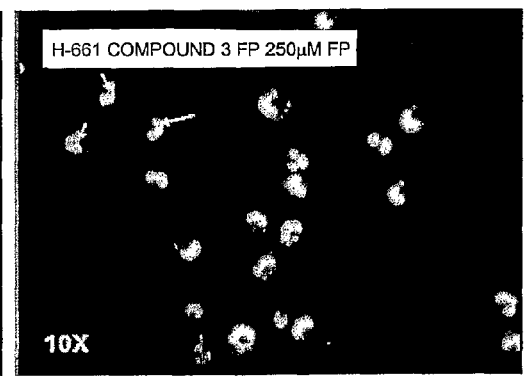
Figure 18:
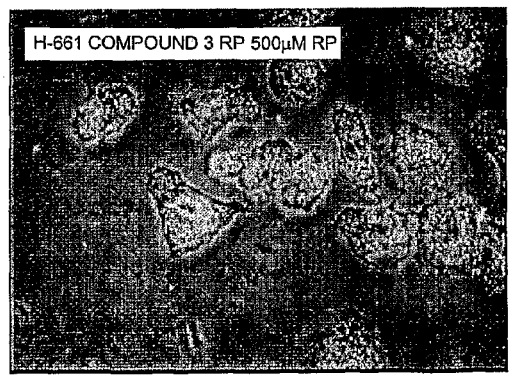
Figure 18:
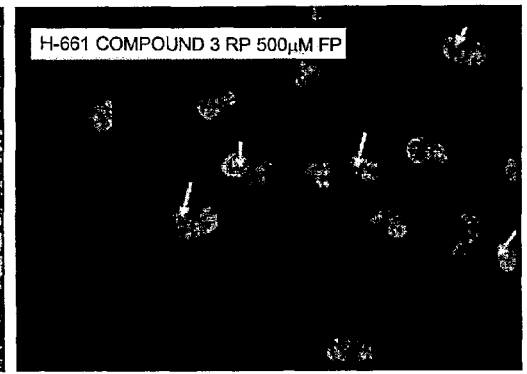

The results are shown in FIG. 17 (MDA-MB-231) and FIG. 18 (H-661). All images are 20× in magnification except for FIG. 18, panel E, which is 10× magnification. The results are shown as matching images: The left side images are reverse phase and the right side images show the nuclei stained with Hoechst reagent. The two cell lines show a clear dose response with increasing cytopathy as shown by extensive vacuolization of the cytoplasm. Cell death is shown as birefringent cells especially in the 10× magnification reverse phase image (FIG. 18, panel E). Although no clear DNA laddering was obtained, chromatin packing and eccentric chromatin location suggest that apoptotic signals were triggered by compound 3.

Example 16

Effect of Compounds 1 to 10 on Cell Migration/Invasion

MDA-MB-231, an invasive breast cancer cell line (Epidermal growth factor positive), was used for measuring the migration inhibition potential of compounds using standard protocols based on migration of cells through a Matrigel matrix. All treatments were made in triplicate. The results are shown in Table 15. Data are expressed as the percent invasion through the Matrigel matrix and membrane related to the migration through the control membrane. % invasion and % invasion inhibition are calculated as follows:

$$\% \text{ Invasion} = \frac{\text{mean \# of cells invading through matrigel insert membrane}}{\text{mean \# of cells migrating through control insert membrane}} \times 100$$

% Invasion inhibition=% Invasion in Control cells–% invasion compound-treated cells

TABLE 15

Inhibition of Invasion of MDA-MB-231 cells by PKI Compounds

| Compound | No. Cells Invading Matrigel Insert | No. Cells Migrating through Control Insert | % Invasion | % Inhibition of Invasion |
|---|---|---|---|---|
| 6 | 50.3 | 179.33 | 28.0 | 8.2 |
| Control | 82.3 | 226.6 | 36.2 | |
| 4 | 18.0 | 230.6 | 7.8 | 29.1 |
| Control | 159.3 | 432.0 | 36.9 | |
| 8 | 84.3 | 96.3 | 87.6 | 1.7 |
| Control | 222.3 | 249.0 | 89.3 | |

TABLE 15-continued

Inhibition of Invasion of MDA-MB-231 cells by PKI Compounds

| Compound | No. Cells Invading Matrigel Insert | No. Cells Migrating through Control Insert | % Invasion | % Inhibition of Invasion |
|---|---|---|---|---|
| 1 | 52.0 | 210 | 35.9 | 5.8 |
| Control | 145.0 | 217.66 | 41.2 | |
| 9 | 40.6 | 101.7 | 39.9 | 6.5 |
| Control | 101.3 | 218.3 | 46.4 | |
| 2 | 34.6 | 63.3 | 62.1 | 2.0 |
| Control | 93.0 | 125.3 | 64.1 | |
| 3 | 20.0 | 210.0 | 9.5 | 29.8 |
| Control | 90.7 | 210.0 | 39.34 | |

Compounds 5, 7 and 10 were tested for their motility by a method described by Zhang W. et al. ((2003) *J. Neurosurgery*, 99(6):1039-46). In brief, MDA-M-231 cells were plated in the centre of round petri dishes 10 cm in diameter at a density of $2 \times 10^4$ cells in 200 µl of RPMI+10% FBS. Prior to plating the control and treated cells, 4 circles were drawn on the outer side of the base of the petri dishes. After 6 h incubation at 37° C. in a humidified 5% $CO_2$ atmosphere, the medium was removed and discarded and a circular zone of adherent cells in the centre of the Petri dish was formed. These cells were washed with medium without serum and were supplemented with fresh medium containing serum. The culture was incubated at 37° C. for a further 6 days.

To determine cell motility, the number of cells at a predetermined distance from the perimeter of the central zone was counted daily in triplicate and % motility was calculated relative to control cells, which were considered as 100% motile.

After 5 days, the inhibition of motility was 3.5%, 3.0% and 5.0% for compounds 10, 7, and 5, respectively. No inhibition was observed at day 3 or 4.

Example 17

Effect of Compounds 1 to 10 on Expression of Protein Kinase C Alpha

The effect of compounds 1 to 10 on doxorubicin-induced expression of PKCα in LS180 colon cancer cells and H-661 NSCLC cells was investigated. Cells were exposed to doxorubicin (50 ng/mL) for 3 days prior to exogenous treatment with the PKI compounds at a concentration of 5 µM. Results were acquired by flow cytometry after labelling of the cells with the PKC-alpha #sc 208 antibody.

The protocol used for fixing the cells for flow cytometry is as follows. A minimum of $1.0 \times 10^6$ cells was used in each instance. Cells were trypsinized and spun down at 1,000/5 min at 4° C. All the medium was removed and the cells resuspended in 500 µl of 1×PBS, pH 7.1. The cell suspension was added into 5 mls of 1% paraformaldehyde/PBS on ice and fixed for 15 min on ice. Cells were then centrifuged at 1,000/5 min and resuspended in 10 mls of 1×PBS. Cells were centrifuged again at 1,000/5 min and resuspended in 2 mls of 70% ETOH and kept at −20° C. until needed (up to 1 week). At which time, 2 mls of 1×PBS containing 1% BSA/0.02% $NaN_3$ was added to each tube and the cells were left on ice for 5 min to give the cells time to rehydrate. Cells were then centrifuged at 1,000/5 min and the ETOH/PBS mix removed. The cells were resuspended in 5 mls of 1×PBS and allowed to sit on ice for 5 min. This step was repeated once, then the cells were centrifuged at 1,000/5 min and resuspended in 1 ml of 1×PBS containing 1% BSA/0.02% $NaN_3$ and 5% serum. Blocking was conducted for 30 min at room temperature with inversion every 10 min, then the primary antibody was added directly to each cell tube at the desired concentration and incubated for 1 hr at room temperature inverting every 10 min. Cells were centrifuged at 1,000/5 min, the primary antibody removed and the cells resuspended in 5 mls of 1×PBS. This step was repeated once. Cells were centrifuged at 1,000/5 min and resuspended in 1 ml of 1×PBS w/1% BSA and 0.02% $NaN_3$ (that contains 5% serum) and the secondary antibody was added. Tubes were protected from the light and incubated for 1 hr at room temperature inverting every 10 min. Cells were then centrifuged at 1,000/5 min, the secondary antibody removed and the cells resuspended in 5 mls of 1×PBS. This step was repeated once and then the cells were centrifuged at 1,000/5 min and resuspended in 1 ml of 1×PBS w/1% BSA and 0.02% $NaN_3$ (with the 5% serum added). Tubes were kept on ice until needed for flow cytometry.

Figure 19:
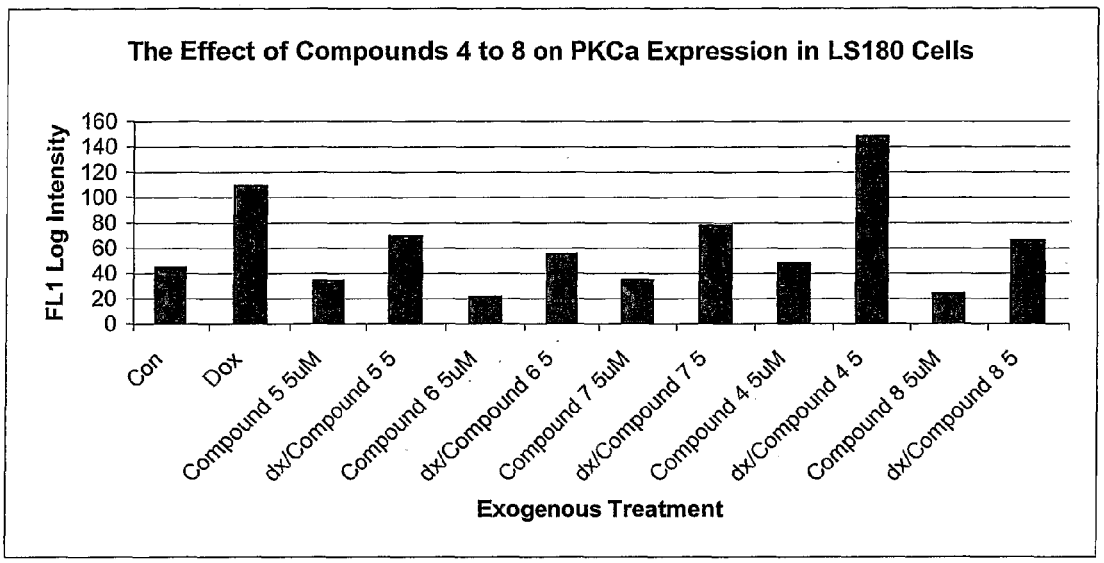
FIG. 19 depicts the effect of compounds 5, 6, 7, 4 and 8 (A), and compounds 1, 9, 2, 3, and 10 (B) on protein kinase C alpha expression in LS180 colon cancer cells in the absence and presence of doxorubicin.
Figure 19:
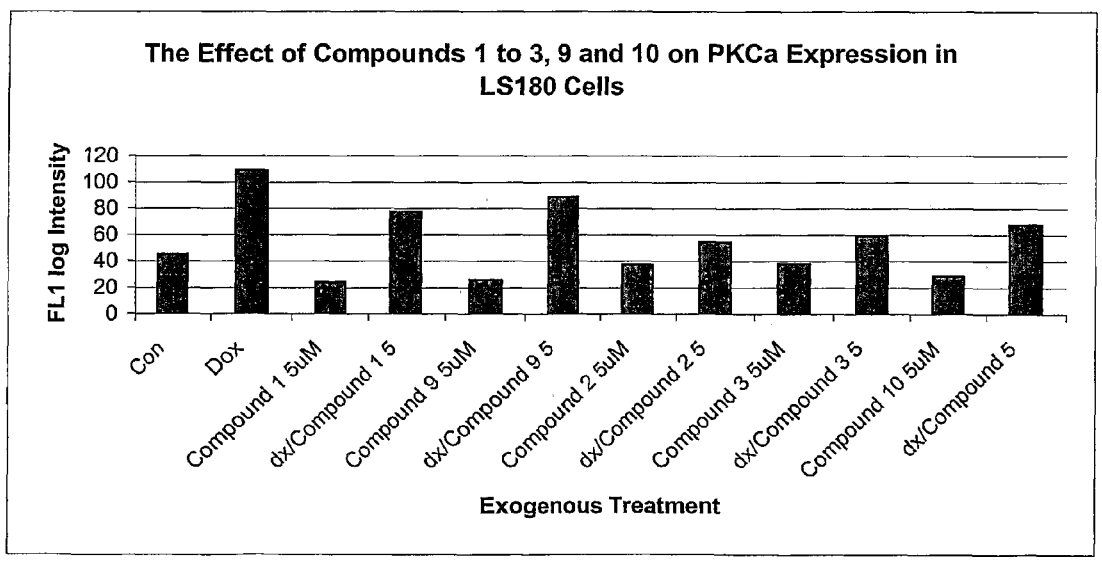

The results of exogenous treatment of LS180 cells with the PKI compounds are summarised in FIG. 19. As can be seen from the figure, in control cells, the increase in log fluorescence relative intensity for cells exposed to doxorubicin for 72 h ranged from 1.30 to 2.43 times (average 1.99). This result was in agreement with the increase in PKCα expression upon treatment with doxorubicin reported in the literature. In cell cultures that were not exposed to doxorubicin, most of the PKI compounds at 5 µM concentration decreased the intracellular level of PKCα. There were indications of a dose response for compounds 4 and 10. The effect of doxorubicin on cells treated with the PKI compounds resulted in approximately a 1.5 times enhancement of PKCα content, with the exception of compounds 4, 1 and 9, which repressed the enzyme expression at the tested concentration, and compound 5, which had no effect at the concentration tested. A dose response was also observed for some of the compounds.

Figure 20:
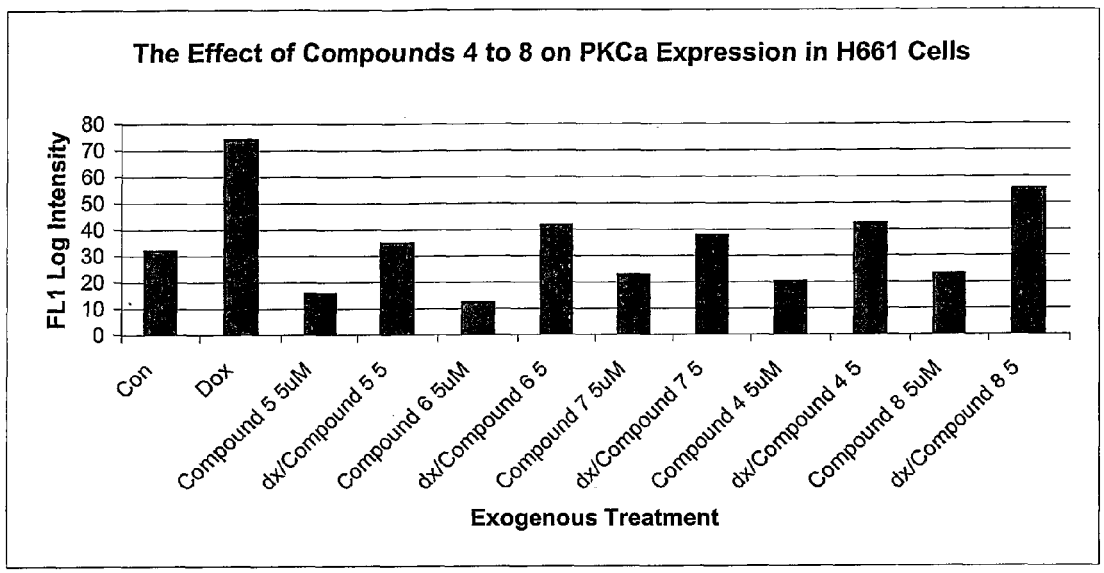
FIG. 20 depicts the effect compounds 5, 6, 7, 4 and 8 (A), and compounds 1, 9, 2, 3, and 10 (B) on protein kinase C alpha expression in H-661 non-small cell lung cancer cells in the absence and presence of doxorubicin.
Figure 20:
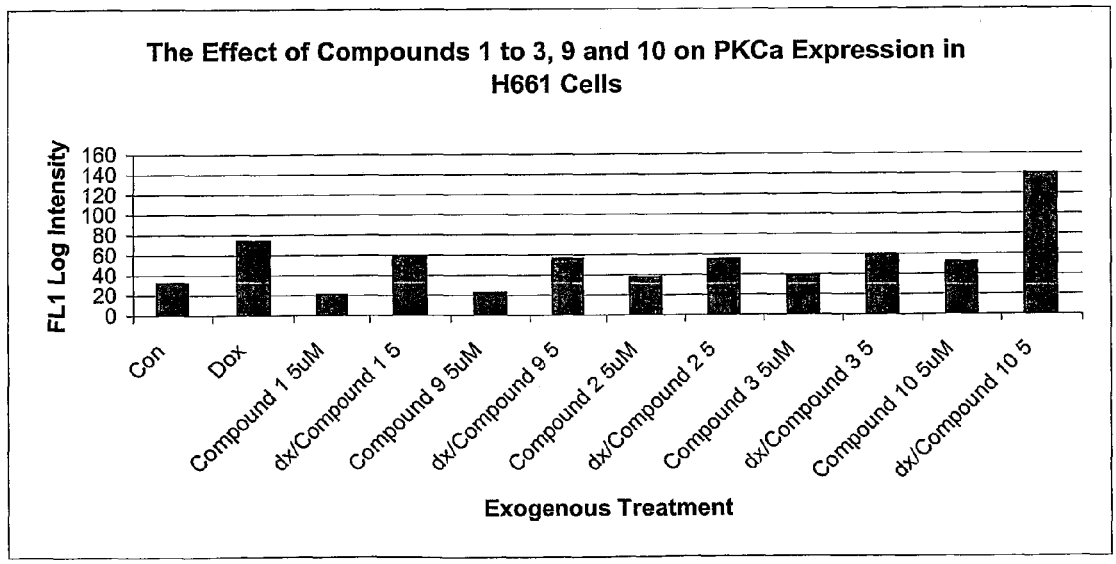

The results of exogenous treatment of H-661 cells with the PKI compounds are summarised in FIG. 20. As can be seen from this figure, in control cells, the increase in log fluorescence relative intensity in cells exposed to doxorubicin for 72 h ranged from 1.61 to 3.59 times (average 2.19). Treatment with 5 µM of compounds 5, 6, 4, 1 and 9 did not have any effect on the expression of PKCα. Compounds 7 and 8 moderately reduced PKCα levels and compounds 2 and 3 were powerful reducers, except when basal expression was low. The effect of doxorubicin on cells treated with compounds 4, 1, 9, 2 and 3 resulted in as high as 50% reduction in PKCα intracellular content. Similar results were obtained with compound 7.

In summary, PKCα expression in untreated cells increases upon exposure to doxorubicin, which is consistent with literature reports. The expression increase resulting from exposure to doxorubicin is around 2-fold over control cells for both cell lines. The effect of the PKI compounds on PKCα basal expression was, to some extent, cell line specific. Compounds 7, 8, 2 and 3 consistently demonstrated a repressive effect.

Example 18

Effect of Compounds 1 to 10 on Multi-Drug Resistance in Cancer Cells #1

Multidrug resistance (MDR) is common to many cancers after a first round of therapy. Typical MDR arises from the expression the mdr-1 gene product P-gp170 that forms a pore in the plasma membrane and acts as an efflux pump. The protein P-gp170 possesses 5 consensus sequences for potential PKC (and PKA) phosphorylation. Non-P-gp170 MDR functions via MRP-1 (the multidrug resistant associated proteins). Like P-gp, the MRP-1 protein forms an ATP-dependent efflux pump that mediates the excretion of toxic agents from the cells.

In view of the key role of the Pgp170 and MRP-1 proteins in MDR, the effect of the PKI compounds on expression of these proteins in LS180 colon cancer cells and H-661 NSCLC cells was investigated. Cells were exposed to doxorubicin (50 ng/mL) for 3 days prior to exogenous treatment with the PKI compounds at a concentration of 5 μM. Results were acquired by flow cytometry, conducted as outlined in Example 17 above, after labelling of the cells with the appropriate antibody (either P-gp #sc 1517 or MRP-1 #sc 7774). The number of cells individually analysed amounted to approximately 50,000 with a statistical error of about 0.08%.

The results are summarised in Tables 16 to 19 below. The increase in the expression of P-gp and MRP-1 was assessed by comparing the % of cells expressing the protein in question in the presence and absence of doxorubicin (i.e. the ratio A/B in the Tables).

TABLE 16

Effect of PKI Compounds on Pgp Expression upon Exposure of LS180 Colon Cancer Cells to Doxorubicin

| | Cells expressing Pgp/% | | |
|---|---|---|---|
| Compound (conc./μM) | No Doxorubicin (B) | +Doxorubicin (A) | Ratio A/B |
| Control | 4.09 | 10.89 | 2.66 |
| 5 (5) | 3.64 | 12.81 | 3.52 |
| 6 (5) | 2.73 | 13.2 | 4.84 |
| Control | 8.54 | 17.9 | 2.10 |
| 5 (5) | 7.43 | 46.28 | 6.23 |
| 6 (5) | 8.55 | 19.12 | 2.24 |
| 7 (5) | 6.55 | 31.24 | 4.77 |
| Control | 8.83 | 12.3 | 1.39 |
| 7 (5) | 7.63 | 13.2 | 1.73 |
| Control | 11.01 | 28.08 | 2.55 |
| 7 (5) | 5.48 | 17.8 | 3.25 |
| Control | 12.59 | 17 | 1.35 |
| 4 (0.5) | 4.44 | 15.86 | 3.57 |
| 4 (1) | 4.38 | 18.89 | 4.31 |
| 4 (5) | 4.40 | 18.19 | 4.13 |
| Control | 5.31 | 19.76 | 3.72 |
| 4 (0.5) | 4.13 | 14.65 | 3.55 |
| 4 (1) | 4.69 | 28.73 | 6.13 |
| 4 (5) | 4.05 | 14.65 | 3.62 |
| Control | 8.54 | 17.9 | 2.10 |
| 8 (5) | 7.2 | 13.42 | 1.86 |
| 1 (5) | 5.37 | 11.3 | 2.10 |
| Control | 11.01 | 28.08 | 2.55 |
| 9 (5) | 4.3 | 18.2 | 4.23 |
| Control | 8.83 | 12.3 | 1.39 |
| 9 (5) | 5.67 | 9.71 | 1.71 |
| Control | 9.45 | 20.5 | 2.17 |
| 2 (5) | 3.58 | 11.36 | 3.17 |
| 3 (5) | 8.85 | 19.47 | 2.20 |
| Control | 5.67 | 17.55 | 3.10 |
| 2 (5) | 3.47 | 21.06 | 6.07 |
| 3 (5) | 2.61 | 10.86 | 4.16 |
| Control | 15.00 | 28.05 | 1.87 |
| 10 (0.5) | 4.62 | 24.52 | 5.31 |
| 10 (1) | 4.41 | 22.44 | 5.09 |
| 10 (5) | 4.45 | 28.36 | 6.37 |

TABLE 17

Effect of PKI Compounds on MRP-1 Expression upon Exposure of LS180 Colon Cancer Cells to Doxorubicin

| | Cells expressing MRP-1/% | | |
|---|---|---|---|
| Compound (conc./μM) | No Doxorubicin (B) | +Doxorubicin (A) | Ratio A/B |
| Control | 4.79 | 13.92 | 2.91 |
| 5 (5) | 4.5 | 15.05 | 3.34 |
| 6 (5) | 3.55 | 10.7 | 3.01 |
| Control | 6.75 | 12.9 | 1.91 |
| 5 (5) | 6.51 | 37.9 | 5.82 |
| 6 (5) | 8.88 | 12.33 | 1.39 |
| 7 (5) | 4.74 | 29.33 | 6.19 |
| Control | 9.91 | 15.73 | 1.59 |
| 7 (5) | 5.69 | 17.06 | 3.00 |
| Control | 10 | 24.46 | 2.45 |
| 7 (5) | 5.78 | 22.42 | 3.88 |
| Control | 5.62 | 26.72 | 4.75 |
| 4 (0.5) | 7.55 | 17.95 | 2.38 |
| 4 (1) | 4.77 | 27.17 | 5.70 |
| 4 (5) | 5.52 | 31.01 | 5.62 |
| Control | 7.62 | 18.82 | 2.47 |
| 4 (0.5) | 6.13 | 17.15 | 2.80 |
| 4 (1) | 7.71 | 14.3 | 1.85 |
| 4 (5) | 5.99 | 20.27 | 3.38 |
| Control | 6.75 | 12.9 | 1.91 |
| 8 (5) | 8.9 | 12.5 | 1.40 |
| 1 (5) | 4.55 | 12.2 | 2.68 |
| Control | 10 | 24.46 | 2.45 |
| 9 (5) | 5.73 | 20.43 | 3.57 |
| Control | 9.91 | 15.73 | 1.59 |
| 9 (5) | 4.98 | 6.57 | 1.32 |
| Control | 3.23 | 18.64 | 5.77 |
| 2 (5) | 5.85 | 18.76 | 3.21 |
| 3 (5) | 3.57 | 25.24 | 7.07 |
| Control | 3.94 | 11.43 | 2.90 |
| 2 (5) | 8.99 | 17.81 | 1.98 |
| 3 (5) | 8.12 | 22.57 | 2.78 |
| Control | 6.44 | 30.03 | 4.66 |
| 10 (0.5) | 3.09 | 6.77 | 2.19 |
| 10 (1) | 3.64 | 6.8 | 1.87 |
| 10 (5) | 3.22 | 7.91 | 2.46 |

TABLE 18

Effect of PKI Compounds on Pgp Expression upon Exposure of H-661 NSCLC Cells to Doxorubicin

| | Cells expressing Pgp/% | | |
|---|---|---|---|
| Compound (conc./μM) | No Doxorubicin (B) | +Doxorubicin (A) | Ratio A/B |
| Control | 2.67 | 23.97 | 9.0 |
| 5 (5) | 1.56 | 21.26 | 13.6 |
| 6 (5) | 1.61 | 35.65 | 22.1 |
| Control | 4.88 | 59.44 | 12.2 |
| 5 (5) | 1.66 | 54.4 | 32.8 |
| 6 (5) | 1.06 | 52.45 | 49.5 |
| Control | 54.64 | 72.38 | 1.3 |
| 7 (5) | 14.38 | 64.75 | 4.5 |
| 8 (5) | 16.15 | 69.43 | 4.3 |
| Control | 19.91 | 61.62 | 3.1 |
| 7 (5) | 2.50 | 75.18 | 30.1 |
| 8 (5) | 2.82 | 70.78 | 25.1 |
| Control | 31.99 | 85.65 | 2.7 |
| 4 (0.5) | 5.51 | 51.12 | 9.3 |
| 4 (1) | 6.68 | 63.71 | 9.5 |
| 4 (5) | 14.24 | 61.68 | 4.3 |
| Control | 49.45 | 68.81 | 1.4 |
| 4 (0.5) | 24.01 | 64.81 | 2.7 |
| 4 (1) | 16.58 | 69.96 | 4.2 |
| 4 (5) | 53.09 | 53.18 | 1.0 |
| Control | 5.10 | 40.98 | 8.0 |
| 1 (5) | 4.72 | 46.27 | 9.8 |
| 9 (5) | 2.78 | 50.48 | 18.2 |

TABLE 18-continued

Effect of PKI Compounds on Pgp Expression upon Exposure of H-661 NSCLC Cells to Doxorubicin

| Compound (conc./μM) | Cells expressing Pgp/% | | Ratio A/B |
|---|---|---|---|
| | No Doxorubicin (B) | +Doxorubicin (A) | |
| Control | 1.08 | 72.7 | 67.3 |
| 1 (5) | 1.78 | 58.89 | 33.1 |
| 9 (5) | 1.26 | 25.28 | 20.1 |
| Control | 5.93 | 64.1 | 10.8 |
| 3 (0.5) | 2.04 | 47.66 | 23.4 |
| 3 (1) | 2.65 | 56.85 | 21.5 |
| 3 (5) | 3.19 | 53.23 | 16.7 |
| Control | 0.67 | 33.57 | 50.1 |
| 2 (5) | 0.79 | 27.84 | 35.2 |
| 3 (5) | 0.59 | 25.92 | 43.9 |
| Control | 15.47 | 78.3 | 5.1 |
| 2 (5) | 10.45 | 71.33 | 6.8 |
| 3 (5) | 16.53 | 75.3 | 4.6 |
| Control | 3.23 | 67.68 | 21.0 |
| 2 (5) | 3.08 | 67.94 | 22.1 |
| 3 (5) | 1.90 | 62.32 | 32.8 |
| Control | 41.83 | 83.99 | 2.0 |
| 10 (0.5) | 4.14 | 62.42 | 15.1 |
| 10 (1) | 8.77 | 61.75 | 7.0 |
| 10 (5) | 6.10 | 56.3 | 9.2 |
| Control | 3.01 | 48.73 | 16.2 |
| 10 (0.5) | 4.13 | 47.55 | 11.5 |
| 10 (1) | 2.54 | 49.06 | 19.3 |
| 10 (5) | 2.53 | 54.21 | 21.4 |

TABLE 19

Effect of PKI Compounds on MRP-1 Expression upon Exposure of H-661 NSCLC Cells to Doxorubicin

| Compound (conc./μM) | Cells expressing MRP-1/% | | Ratio A/B |
|---|---|---|---|
| | No Doxorubicin (B) | +Doxorubicin (A) | |
| Control | 2.76 | 32.86 | 11.9 |
| 5 (5) | 2.25 | 39.7 | 17.6 |
| 6 (5) | 3.34 | 38.07 | 11.4 |
| Control | 7.84 | 63.43 | 8.1 |
| 5 (5) | 2.47 | 55.82 | 22.6 |
| 6 (5) | 1.17 | 61.2 | 52.3 |
| Control | 51.26 | 71.17 | 1.4 |
| 7 (5) | 10.05 | 58.22 | 5.8 |
| 8 (5) | 11.95 | 64.48 | 5.4 |
| Control | 8.65 | 69.75 | 8.1 |
| 7 (5) | 4.04 | 72.58 | 18.0 |
| 8 (5) | 5.32 | 72.09 | 13.6 |
| Control | 28.13 | 80.05 | 2.8 |
| 4 (0.5) | 27.36 | 52.09 | 1.9 |
| 4 (1) | 10.32 | 65.17 | 6.3 |
| 4 (5) | 10.79 | 66.4 | 6.2 |
| Control | 34.31 | 37.63 | 1.1 |
| 4 (0.5) | 39.65 | 72.68 | 1.8 |
| 4 (1) | 40.88 | 61.66 | 1.5 |
| 4 (5) | 34.76 | 70.18 | 2.0 |
| Control | 2.74 | 46.84 | 16.9 |
| 1 (5) | 5.5 | 34.08 | 6.2 |
| 9 (5) | 3.64 | 41.88 | 11.5 |
| Control | 2.42 | 73.28 | 30.3 |
| 1 (5) | 2.84 | 36.13 | 12.7 |
| 9 (5) | 1.93 | 30.3 | 15.7 |
| Control | 5.12 | 71.91 | 14.0 |
| 3 (0.5) | 5.24 | 49.95 | 9.5 |
| 3 (1) | 3.82 | 66.37 | 17.4 |
| 3 (5) | 4.36 | 52.55 | 12.1 |
| Control | 1.31 | 34.07 | 26.0 |
| 2 (5) | 1.18 | 24.36 | 20.6 |
| 3 (5) | 0.64 | 28.42 | 44.4 |

TABLE 19-continued

Effect of PKI Compounds on MRP-1 Expression upon Exposure of H-661 NSCLC Cells to Doxorubicin

| Compound (conc./μM) | Cells expressing MRP-1/% | | Ratio A/B |
|---|---|---|---|
| | No Doxorubicin (B) | +Doxorubicin (A) | |
| Control | 26.44 | 82.31 | 3.1 |
| 2 (5) | 15.40 | 79.51 | 5.2 |
| 3 (5) | 19.01 | 78.67 | 4.1 |
| Control | 5.18 | 65.51 | 12.6 |
| 2 (5) | 5.89 | 62.85 | 10.7 |
| 3 (5) | 3.01 | 59.53 | 19.9 |
| Control | 28.95 | 83.59 | 2.9 |
| 10 (0.5) | 3.91 | 48.62 | 12.4 |
| 10 (1) | 4.82 | 58.75 | 12.2 |
| 10 (5) | 12.93 | 59.26 | 4.6 |
| Control | 2.69 | 79.28 | 29.5 |
| 10 (0.5) | 10.59 | 59.96 | 5.7 |
| 10 (1) | 12.54 | 62.60 | 5.0 |
| 10 (5) | 10.2 | 64.63 | 6.3 |

As can be seen from Table 16, in LS180 cells, the increase in number of P-gp labelled cells in the control cell population exposed to doxorubicin for 72 h ranged from 1.35 to 3.72 times (average 2.38). In PKI compound treated cells (without doxorubicin), none of the PKI compounds enhanced the level of the P-gp basal expression. Cells treated with compounds 5, 6 and 8 showed equal or close to basal expression. Cells treated with compound 4 showed very stable content with 4% of cells labelled (a value lower than that of the control). Compounds 7, 1, 2, 9 and 10, decreased the basal expression to a variable extent with compound 10 altering the Pgp level very efficiently. In cells exposed to doxorubicin, compounds 6, 4, 9 and 10 showed Pgp expression levels similar or slightly lower than that of controls, while there was a moderate decrease when cells were exposed to compounds 8 or 1.

As can be seen from Table 17, in LS180 cells, the increase in number of MRP-1 labelled cells in the control cell population exposed to doxorubicin for 72 h ranged from 1.91 to 6.19 times (average 3.41). In treated cells (without doxorubicin), compounds 5, 6 and 8 did not alter the basal expression of MRP-1. Compounds 7, 9, 1 and 10 showed lower values than that of the controls. In cells exposed to doxorubicin, compound 9 and compound 10 inhibited MRP-1 expression.

In H-661 cells, as shown in Table 18, the increase in number of P-gp labelled cells in the control cell population exposed to doxorubicin for 72 h ranged from 1.3 to 67.3 times (average 15.0). The increase was very variable from experiment to experiment. In treated cells (without doxorubicin), compounds 5, 6, 7 and 8 decreased the basal expression of P-gp, the latter two drastically. In cells exposed to doxorubicin, a moderate decrease with dosage was shown with compound 4, and compound 2 exhibited a clear decrease.

As can be seen from Table 19, in H-661 cells, the increase in number of MRP-1 labelled cells in the control cell population exposed to doxorubicin for 72 h ranged from 1.10 to 29.5 times (average 12.05). In treated cells (without doxorubicin), compounds 6, 8, 2, 3 and 10 decreased MRP-1 expression. In cells exposed to doxorubicin, compounds 5 and 6 give values similar to that of controls. All the other compounds tested negatively altered MRP-1 expression at different levels up to ~60%. The decrease in expression resulting from exposure to compound 4 exhibited a dose response; the higher the dose, the greater the decrease in expression.

Example 19

Effect of Compounds 1 to 10 on Multi-Drug Resistance in Cancer Cells #2

The amount of rhodamine influx and efflux following treatment of LS180 colon cancer cells and H-661 NSCLC cells with the PKI compounds was also investigated. The measurement of rhodamine efflux and influx is a common procedure that provides a quantitative estimation of the level of multi-drug resistance due to typical MDR and non-P-gp MDR. Both exogenous treatment using 5 µg/mL of the PKI compounds provided at the same time as doxorubicin, and endogenous incorporation, in which a single dose of 5 mM was used with the standard pinocytic endocytosis protocol, were investigated.

The MDR-1 pump functions only as an efflux pump, however, it modulates the cell entry of rhodamine (that can diffuse through the membrane). Upon toxicant exposure, rhodamine accumulates in the cells. Ratios of rhodamine fluorescence in doxorubicin exposed versus untreated controls (CT) are lower if the pump is inhibited.

Figure 21:
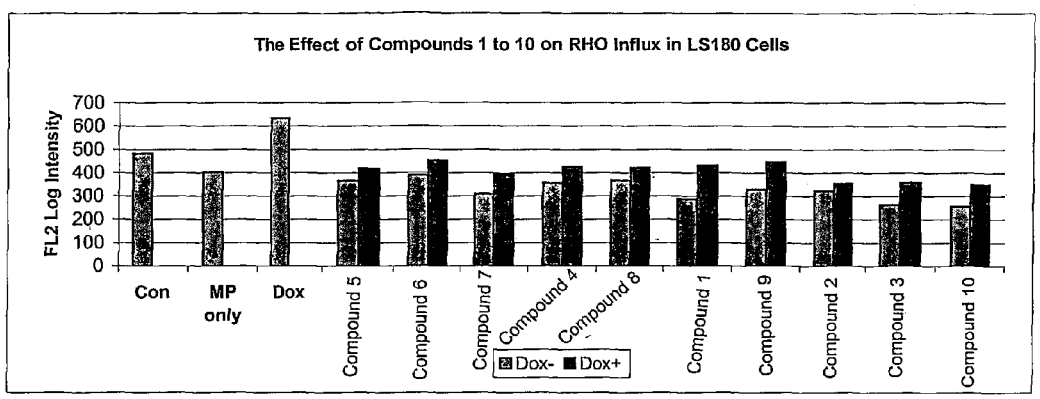
FIG. 21 depicts the effect of endogenous treatment of LS180 colon cancer cells with compounds 1 to 10 on the influx of rhodamine (A), the effect of endogenous treatment of LS180 colon cancer cells with compounds 4 to 8 (B), and the effect of endogenous treatment of LS180 colon cancer cells with compounds 1, 2, 3, 9 and 10 (C).
Figure 21:
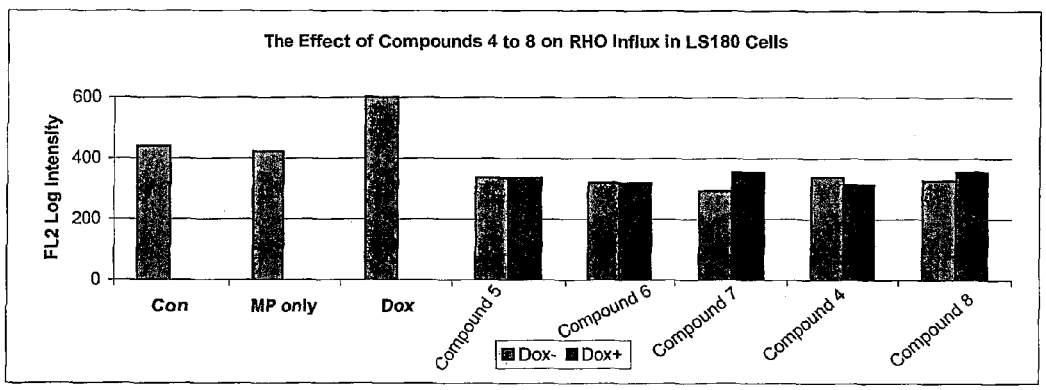
Figure 21:
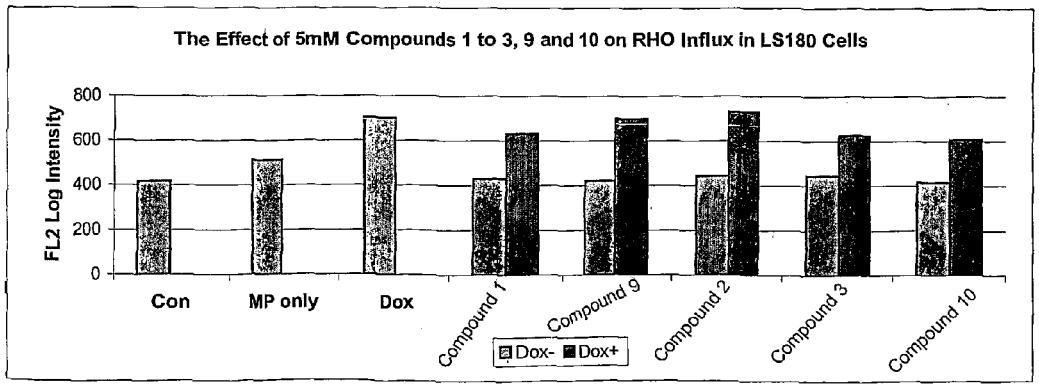
Figure 23:
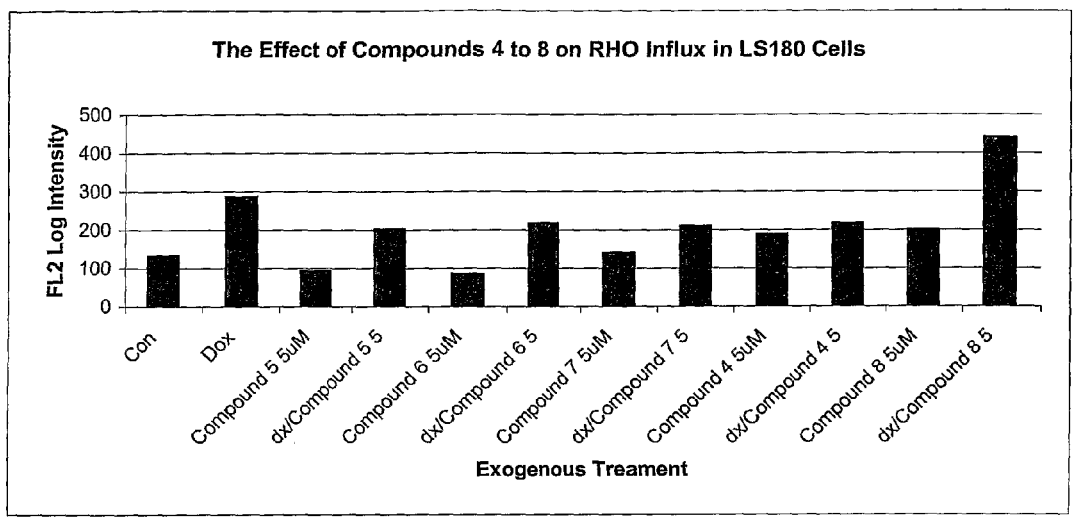
FIG. 23 depicts the effect of exogenous treatment of LS180 colon cancer cells with compounds 1 to 5 (A) and 6 to 10 (B) on the influx of rhodamine.
Figure 23:
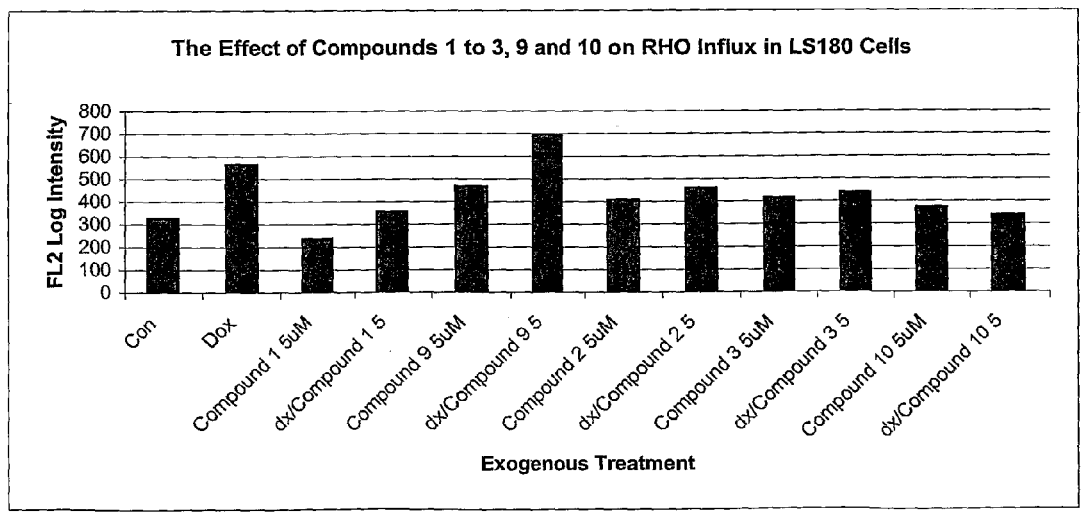

For LS180 colon cancer cells, rhodamine accumulates at 1.58, 1.43 and 1.37 times in doxorubicin exposed controls, however, the rate at which rhodamine accumulation increases in the cell populations treated endogenously with the PKI compounds remained lower in most cases (FIG. 21A; B & C depict a duplicate experiment). Exogenous treatment of the cells with the PKI compounds was less effective (FIGS. 23A & B).

Figure 22:
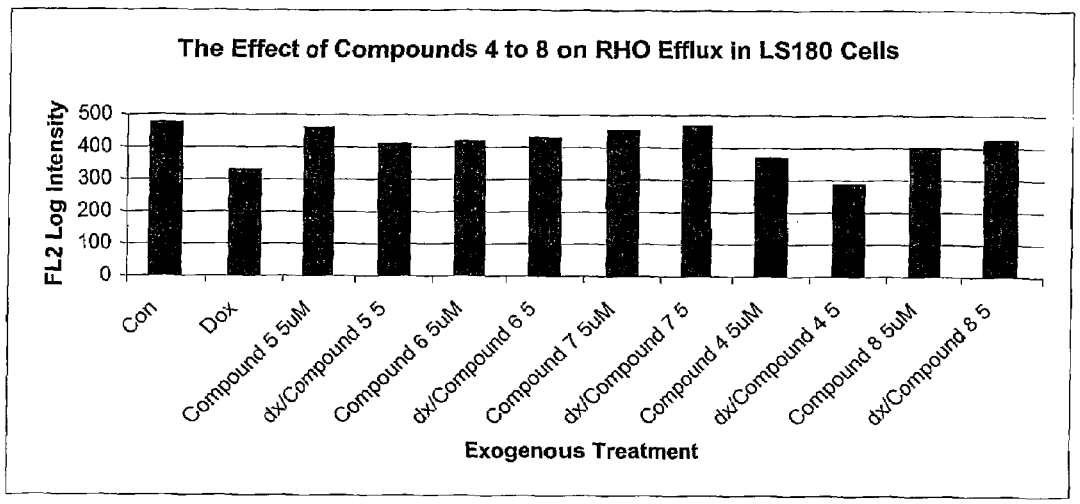
FIG. 22 depicts the effect of exogenous treatment of LS180 colon cancer cells with compounds 1 to 5 (A) and 6 to 10 (B) on the efflux of rhodamine.
Figure 22:
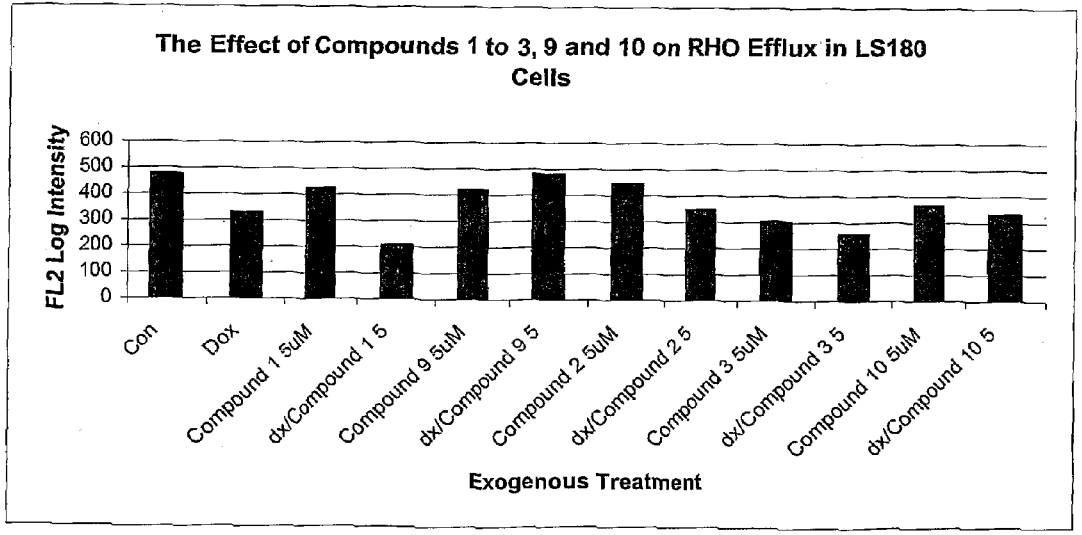

Measurement of rhodamine efflux in LS180 cells treated exogenously with the PKI compounds clearly showed that upon doxorubicin exposure the intracellular accumulation of rhodamine diminished in control cells, as expected. Compounds 6, 8 and 9 were effective in limiting the pump activity (FIGS. 22A & B).

Figure 24:
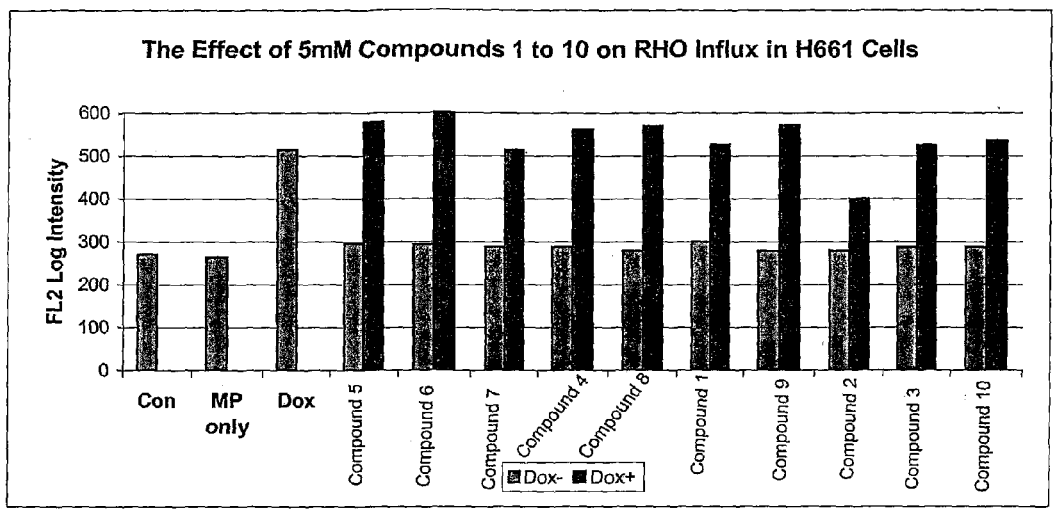
FIG. 24 depicts the effect of endogenous treatment of H-661 non-small cell lung cancer cells with compound 1 to 10 on the influx of rhodamine. (A) and (B) are duplicative experiments.
Figure 24:
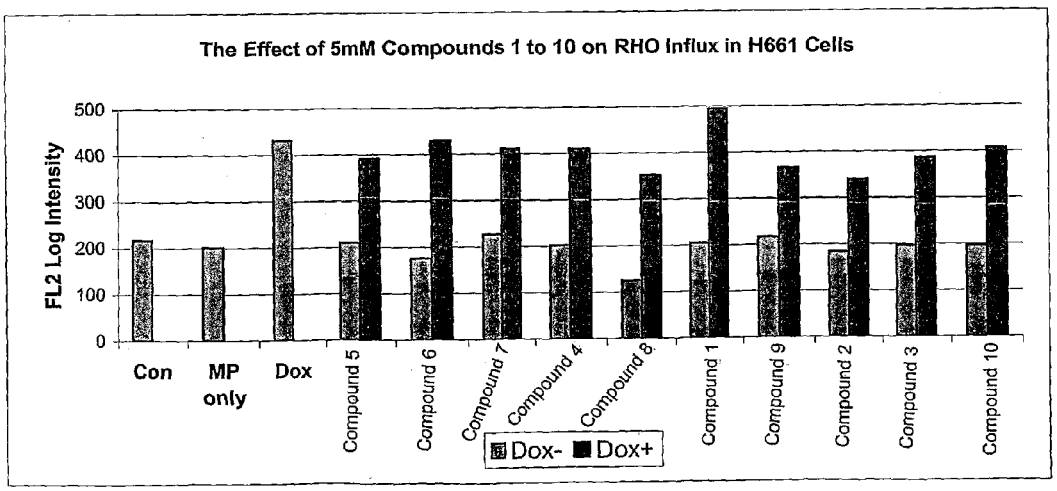
Figure 25:
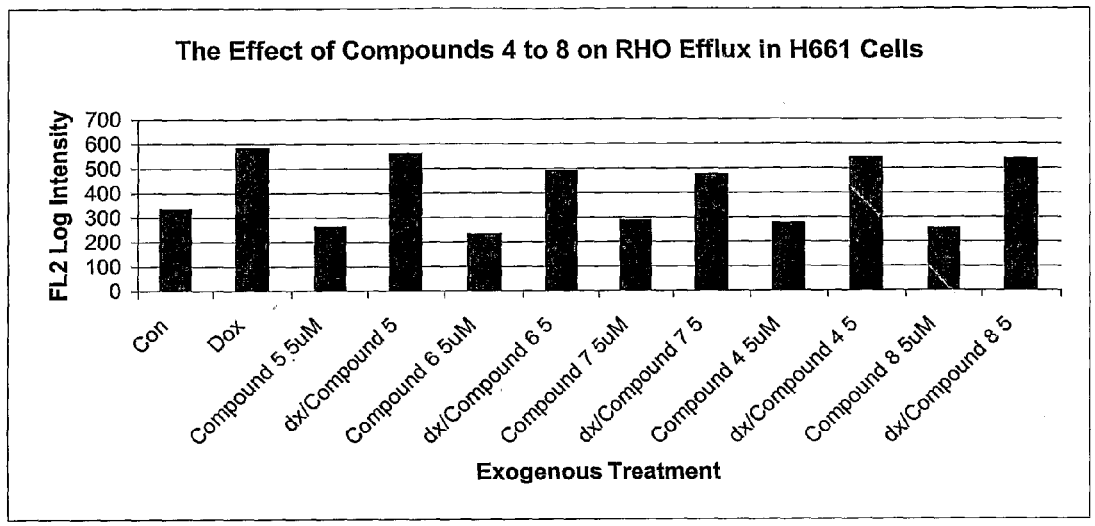
FIG. 25 depicts the effect of exogenous treatment of H-661 non-small cell lung cancer cells with compounds 1 to 5 (A) and 6 to 10 (B) on the efflux of rhodamine.
Figure 25:
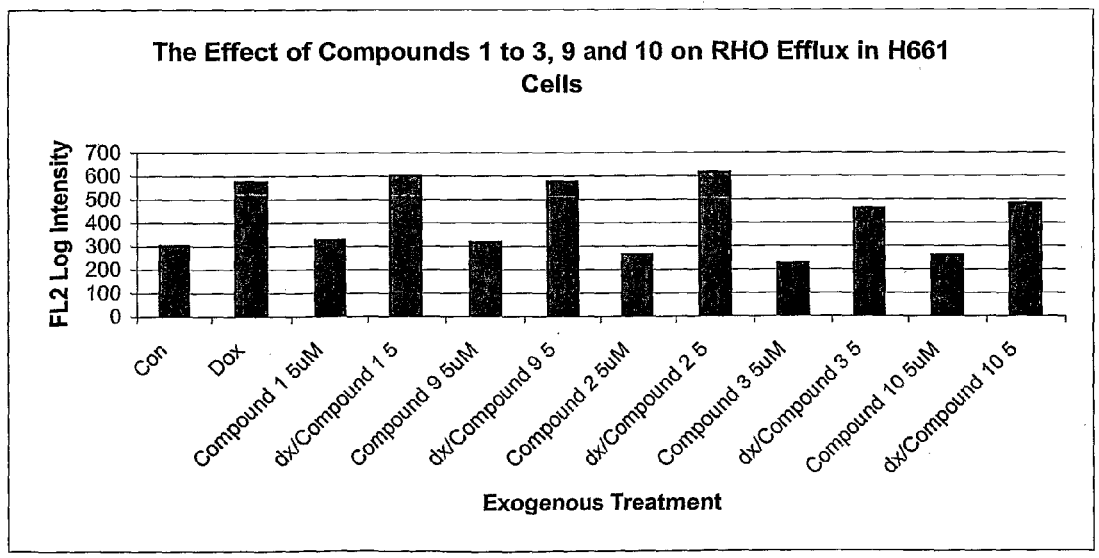

For H-661 NSCLC cells, exposure of control cells to doxorubicin resulted in a large increase in rhodamine retention (~2.00 times). The accumulation of rhodamine was reduced by 22% in comparison to the control by compound 2 when the cells were treated endogenously with this compound (FIG. 24A; B depicts a duplicate experiment). Exogenous treatment with compounds 9 and 3 resulted in a reduction of 27% and 22% of rhodamine influx at the lowest concentration and highest concentrations, respectively (FIG. 25).

The disclosure of all patents, publications, including published patent applications, and database entries referenced in this specification are specifically incorporated by reference in their entirety to the same extent as if each such individual patent, publication, and database entry were specifically and individually indicated to be incorporated by reference.

Although the invention has been described with reference to certain specific embodiments, various modifications thereof will be apparent to those skilled in the art without departing from the spirit and scope of the invention as outlined in the claims appended hereto.

---

The Embodiments of the invention in which an exclusive property or privilege is claimed are defined as follows:

1. A peptidic compound comprising between about 5 and about 20 amino acids and having the Formula (III):

$$(C2)J(M)\text{-}N_y B_z A_x B_y N_y \quad (III)$$

wherein:

C2 is $B_y(A/N)_x B_y N_y$ and is attached to J by a peptide bond from the N- or C-terminus of C2;

J comprises two Cys residues and optionally 1-2 residues selected from His and Lys, the Cys residues are linked by a disulphide bond and the compound of Formula (III) thereby comprises a first peptide chain comprising a first of said two Cys residues and C2, and a second peptide chain comprising a second of said two Cys residues and the sequence $N_y B_z A_x B_y N_y$;

M is an ATP mimetic moiety optionally linked to an amino acid selected from the group of Ile, Leu, Val or Gly and is attached to J via the N-terminus of one of the Cys residues;

each N is independently Ala, Ile, Leu, Val or Gly;

each B is independently Arg, Lys or Tyr; and each A is independently Phe, His or Trp;

each x is independently 0-1;

each y is independently 0-2; z=0-3; and the sequence $\text{-}N_y B_z A_x B_y N_y$ is 2 or more amino acids in length, wherein said peptidic compound is capable of inhibiting one or more protein kinases.

2. The peptidic compound according to claim 1, wherein said peptidic compound comprises a modified N-terminus and/or C-terminus.

3. The peptidic compound according to claim 1, wherein one of said protein kinases is protein kinase C alpha.

4. A peptidic compound comprising between about 5 and about 20 amino acids and having the Formula (IV):

$$N_xB_y(A/N)_xB_yN_y\text{-}J(M)\text{-}N_yB_zA_xB_yN_yB_x \quad (IV)$$

wherein:

J is 1-2 Lys residues or a Cys residue;

M is an ATP mimetic moiety optionally linked to an amino acid selected from the group of Ile, Leu, Val or Gly and is attached to J via the side chain of one of the Lys residues or the N-terminus of the cysteine residue;

each N is independently Ala, Ile, Leu, Val or Gly;

each B is independently Arg, Lys or Tyr; and each A is independently Phe, His or Trp;

each x is independently 0-1;

each y is independently 0-2;

z=0-3; and the sequence $-N_yB_zA_xB_yN_yB_x$ is 2 or more amino acids in length, and wherein said peptidic compound is capable of inhibiting one or more protein kinases.

5. A peptidic compound selected from the group consisting of:

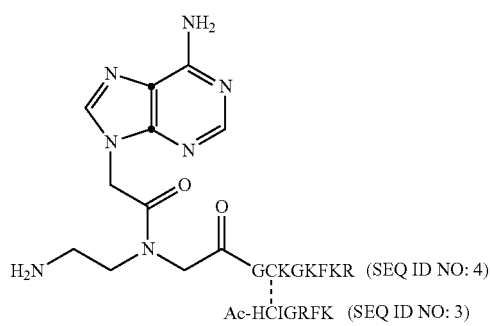

Ac-HCIGRFK (SEQ ID NO: 3)
GCKGKFKR (SEQ ID NO: 4)

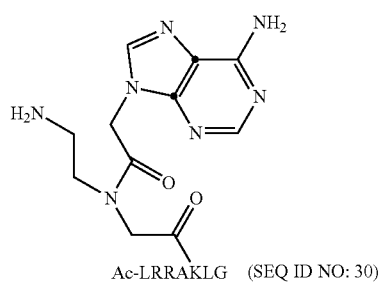

Ac-LRRAKLG (SEQ ID NO: 30)

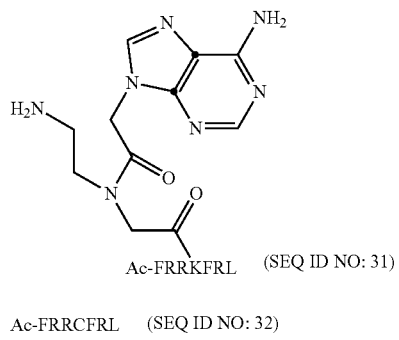

Ac-FRRKFRL (SEQ ID NO: 31)

Ac-FRRCFRL (SEQ ID NO: 32)

-continued

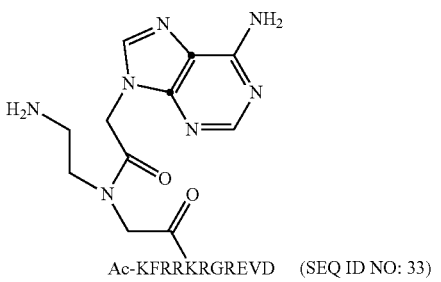

Ac-KFRRKRGREVD (SEQ ID NO: 33)

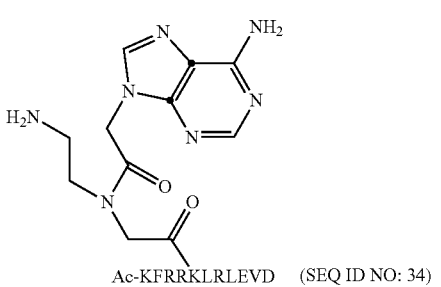

Ac-KFRRKLRLEVD (SEQ ID NO: 34)

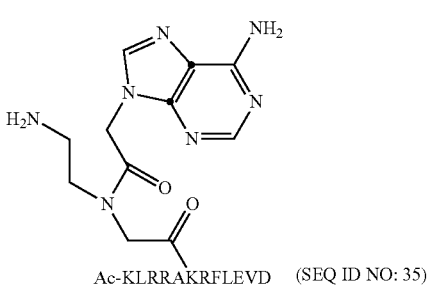

Ac-KLRRAKRFLEVD (SEQ ID NO: 35)

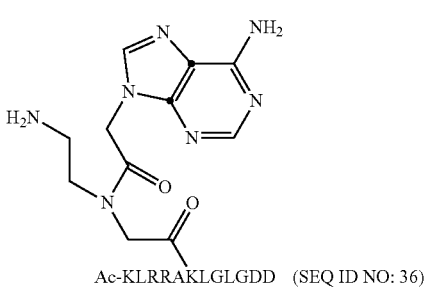

Ac-KLRRAKLGLGDD (SEQ ID NO: 36)

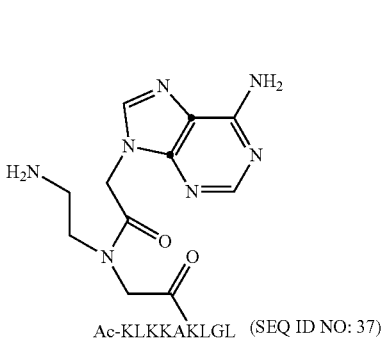

Ac-KLKKAKLGL (SEQ ID NO: 37)

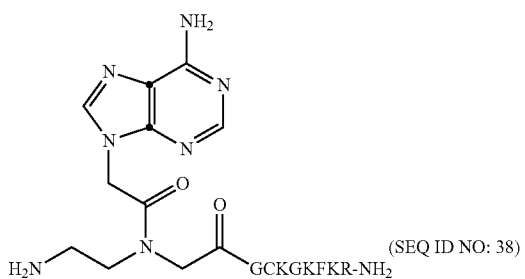
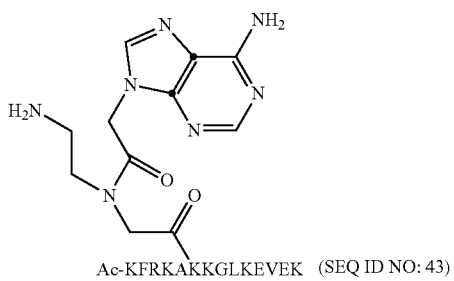
wherein said peptidic compound is capable of inhibiting one or more protein kinases.

6. A composition comprising the peptidic compound according to any one of claims 1, 4 or 5, and a pharmaceutically acceptable diluent or carrier.

7. A method of inhibiting a protein kinase in a subject comprising administering to said subject an effective amount of the peptidic compound according to any one of claims 1, 4 or 5.

8. The method according to claim 7, wherein said protein kinase is selected from the group of: a PKCα isoform, MAPKp38, protein kinase B and protein kinase A.

9. A method of inhibiting the proliferation of cancer cells comprising contacting said cancer cells with an effective amount of the peptidic compound according to any one of claims 1, 4 or 5.

10. The method according to claim 9, wherein said cancer cells are in vitro.

11. The method according to claim 9, wherein said cancer cells are in vivo.

12. A method of treating a protein kinase mediated disease or disorder in a subject comprising administering to said subject an effective amount of the peptidic compound according to any one of claims 1, 4 or 5.

13. The method according to claim 12, wherein said protein kinase mediated disease or disorder is cancer, psoriasis, angiogenesis, restenosis, atherosclerosis, cardiovascular disease, hypertension, diabetes, a neurological disorder, rheumatoid arthritis, a kidney disorder, an inflammatory disorder or an autoimmune disorder.

14. The method according to claim 12, wherein said protein kinase mediated disease or disorder is cancer.

15. The peptidic compound according to claim 4, wherein J is 1-2 Lys residues and M is an ATP mimetic moiety attached to J via the side chain of one of the Lys residues.

16. The peptidic compound according to claim 15, wherein said ATP mimetic is a compound of Formula (XXXIII):

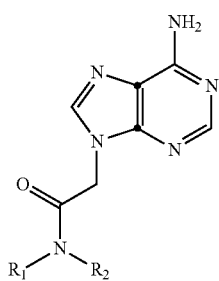

(XXXIII)

wherein:
R₁ and R₂ are independently alkyl substituted with a carboxyl, carbonyl, alcohol or primary amino.

17. The peptidic compound according to claim 15, wherein said peptidic compound comprises between about 5 and 16 amino acids.

18. The peptidic compound according to claim 15, wherein:
each B is independently Arg or Lys; and
each A is independently Phe or His.

19. The peptidic compound according to claim 15, wherein said peptidic compound further comprises at the C-terminus an additional sequence of up to 4 amino acids in length comprising a sequence selected from the group consisting of Glu-Val-Glu, Asp-Asp, Glu-Gly-Glu, Glu-Ile-Glu, Glu-Val-Glu-Lys (SEQ ID NO:47), and Glu-Val-Asp.

20. The peptidic compound according to claim 15, wherein said peptidic compound comprises a modified C-terminus and/or N-terminus.

21. The peptidic compound according to claim 20, wherein said peptidic compound comprises an acetylated N-terminus.

22. The peptidic compound according to claim 15, wherein said peptidic compound is selected from:

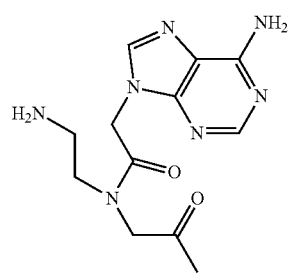

Ac-LRRAKLG
(SEQ ID NO: 30)
2

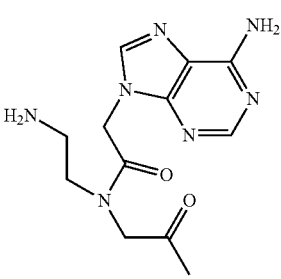

Ac-FRRKFRL
(SEQ ID NO: 31)
3

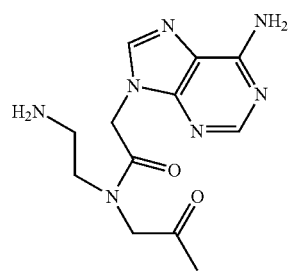

Ac-KFRRKRGREVD
(SEQ ID NO: 33)
5

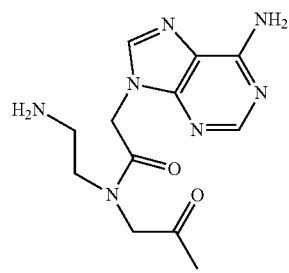

Ac-KFRRKLRLEVD
(SEQ ID NO: 34)
6

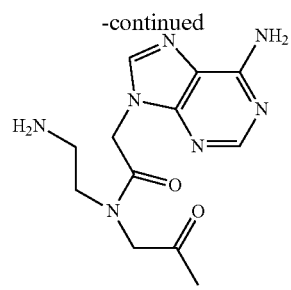

Ac-KLRRAKRLEVD
(SEQ ID NO: 35)

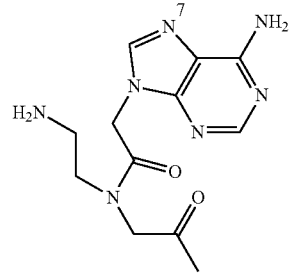

Ac-KLRRAKLGLGDD
(SEQ ID NO: 36)

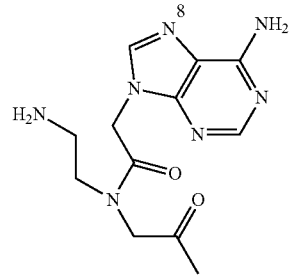

Ac-KLKKAKLGL
(SEQ ID NO: 37)

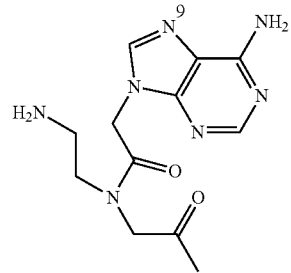

Ac-KAKKKKAKEGE
(SEQ ID NO: 39)

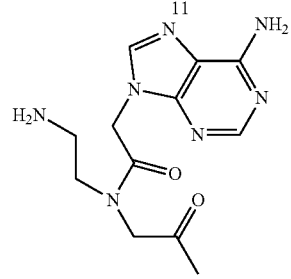

Ac-KLKKLKLVI
(SEQ ID NO: 40)

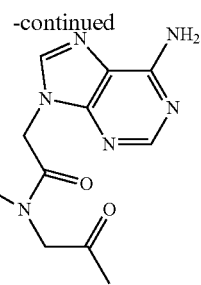

Ac-RFRKAKKGGHEIE
(SEQ ID NO: 41)

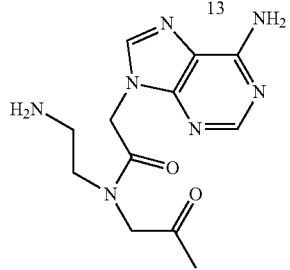

and

Ac-FRRKLI
(SEQ ID NO: 42)

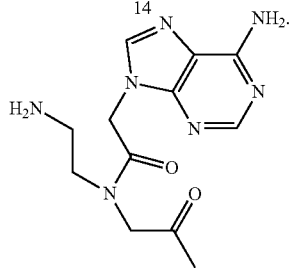

Ac-KFRKAKKGLKEVEK
(SEQ ID NO: 43)

23. The peptidic compound according to claim 15, wherein said peptidic compound is of Formula (V):

$$N_xB_{y'}(A/N)_xB_yN_{y'}\text{-J(M)-}N_yB_zA_xB_yN_{y'} \qquad (V).$$

24. The peptidic compound according to claim 23, wherein said ATP mimetic is a compound of Formula (XXXIII):

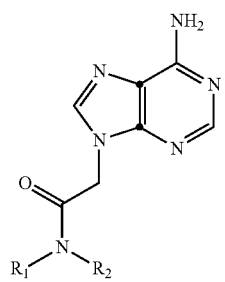

(XXXIII)

wherein:
$R_1$ and $R_2$ are independently alkyl substituted with a carboxyl, carbonyl, alcohol or primary amino.

25. The peptidic compound according to claim 23, wherein said peptidic compound comprises between about 5 and 16 amino acids.

26. The peptidic compound according to claim 23, wherein:
   each B is independently Arg or Lys; and
   each A is independently Phe or His.

27. The peptidic compound according to claim 23, wherein said peptidic compound further comprises at the C-terminus an additional sequence of up to 4 amino acids in length comprising a sequence selected from the group consisting of Glu-Val-Glu, Asp-Asp, Glu-Gly-Glu, Glu-Ile-Glu, Glu-Val-Glu-Lys (SEQ ID NO:47), and Glu-Val-Asp.

28. The peptidic compound according to claim 23, wherein said peptidic compound comprises a modified C-terminus and/or N-terminus.

29. The peptidic compound according to claim 28, wherein said peptidic compound comprises an acetylated N-terminus.

30. The peptidic compound according to claim 23, wherein said peptidic compound is selected from the group consisting of:

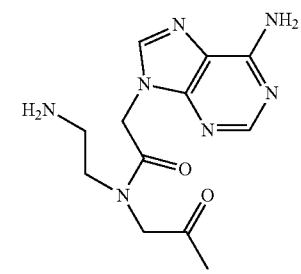

Ac-LRRAKLG
(SEQ ID NO: 30)
2

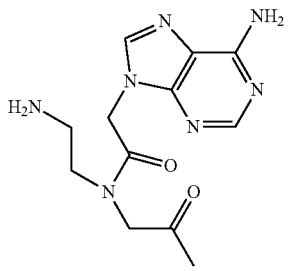

Ac-FRRKFRL
(SEQ ID NO: 31)
3

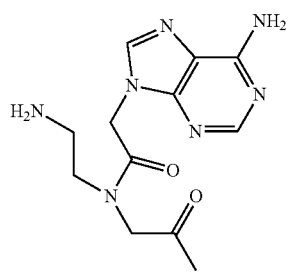

Ac-KFRRKLRLEVD
(SEQ ID NO: 34)
6

-continued

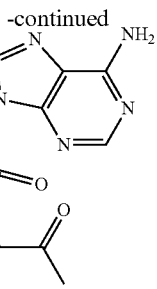

Ac-KLRRAKRLEVD
(SEQ ID NO: 35)
7

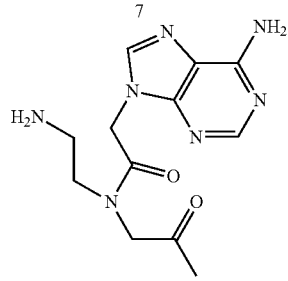

Ac-KLRRAKLGLGDD
(SEQ ID NO: 36)
8

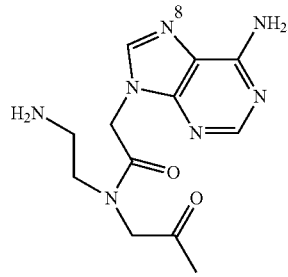

Ac-KLKKAKLGL
(SEQ ID NO: 37)
9

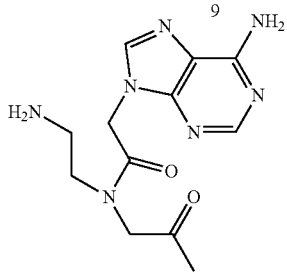

Ac-KAKKKKAKEGE
(SEQ ID NO: 39)
11

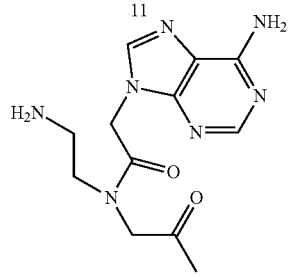

Ac-KLKKLKLVI
(SEQ ID NO: 40)
12

-continued

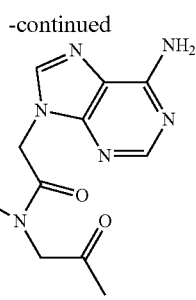

Ac-RFRKAKKGGHEIE
(SEQ ID NO: 41)
13

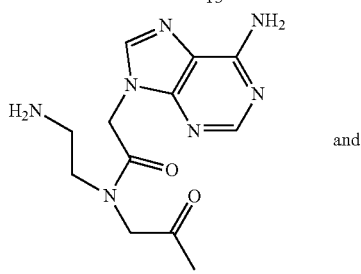

and

Ac-FRRKLI
(SEQ ID NO: 42)
14

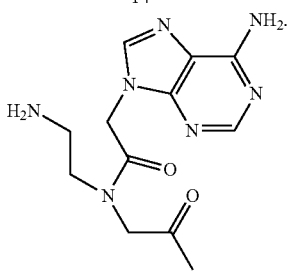

Ac-KFRKAKKGLKEVEK
(SEQ ID NO: 43)
15

31. The peptidic compound according to claim 1, wherein said ATP mimetic is a compound of Formula (XXXIII):

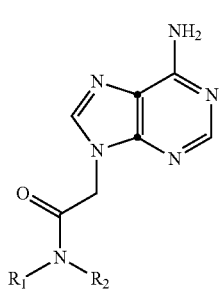

(XXXIII)

wherein:
$R_1$ and $R_2$ are independently alkyl substituted with a carboxyl, carbonyl, alcohol or primary amino.

32. The peptidic compound according to claim 1, wherein said peptidic compound comprises between about 5 and 16 amino acids.

33. The peptidic compound according to claim 1, wherein:
each B is independently Arg or Lys; and
each A is independently Phe or His.

34. The peptidic compound according to claim 1, wherein said peptidic compound further comprises at the C-terminus an additional sequence of up to 4 amino acids in length comprising a sequence selected from the group consisting of Glu-Val-Glu, Asp-Asp, Glu-Gly-Glu, Glu-Ile-Glu, Glu-Val-Glu-Lys (SEQ ID NO:47), and Glu-Val-Asp.

35. The peptidic compound according to claim 4, wherein said peptidic compound comprises a modified C-terminus and/or N-terminus.

36. The peptidic compound according to claim 35, wherein said peptidic compound comprises an acetylated N-terminus.

37. A pharmaceutical composition comprising the peptidic compound according to claim 15 and a pharmaceutically acceptable diluent or carrier.

38. The pharmaceutical composition according to claim 37, wherein said peptidic compound is of Formula (V):

$$N_xB_y(A/N)_xB_yN_y\text{-}J(M)\text{-}N_yB_zA_xB_yN_y \qquad (V).$$

39. The pharmaceutical composition according to claim 38, wherein said ATP mimetic is a compound of Formula (XXXIII):

(XXXIII)

wherein:
$R_1$ and $R_2$ are independently alkyl substituted with a carboxyl, carbonyl, alcohol or primary amino.

40. The pharmaceutical composition according to claim 38, wherein said peptidic compound comprises between about 5 and 16 amino acids.

41. The pharmaceutical composition according to claim 38, wherein:
each B is independently Arg or Lys; and
each A is independently Phe or His.

42. The pharmaceutical composition according to claim 38, wherein said peptidic compound further comprises at the C-terminus an additional sequence of up to 4 amino acids in length comprising a sequence selected from the group consisting of Glu-Val-Glu, Asp-Asp, Glu-Gly-Glu, Glu-Ile-Glu, Glu-Val-Glu-Lys (SEQ ID NO:47), and Glu-Val-Asp.

43. The pharmaceutical composition according to claim 38, wherein said peptidic compound comprises a modified C-terminus and/or N-terminus.

44. The pharmaceutical composition according to claim 43, wherein said peptidic compound comprises an acetylated N-terminus.

45. The pharmaceutical composition according to claim 38, wherein said peptidic compound is selected from the group consisting of:
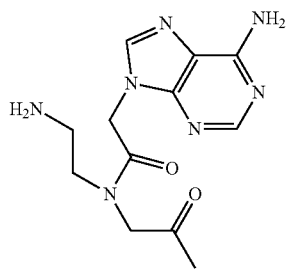
Ac-LRRAKLG
(SEQ ID NO: 30)
2
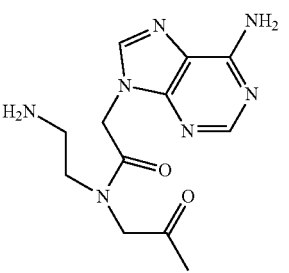
Ac-FRRKFRL
(SEQ ID NO: 31)
3
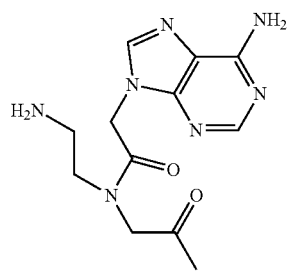
Ac-KFRRKLRLEVD
(SEQ ID NO: 34)
6
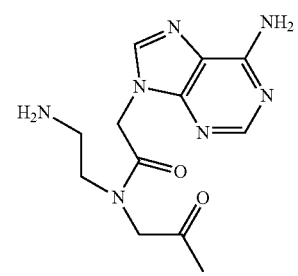
Ac-KLRRAKRLEVD
(SEQ ID NO: 35)
7
-continued
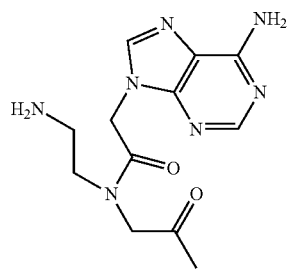
Ac-KLRRAKLGLGDD
(SEQ ID NO: 36)
8
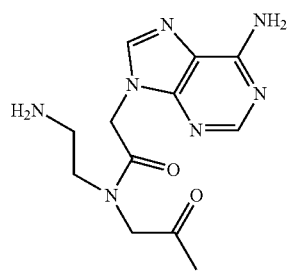
Ac-KLKKAKLGL
(SEQ ID NO: 37)
9
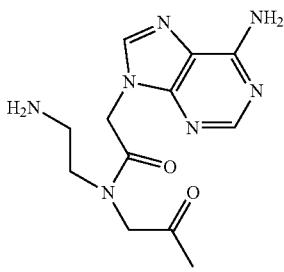
Ac-KAKKKKAKEGE
(SEQ ID NO: 39)
11
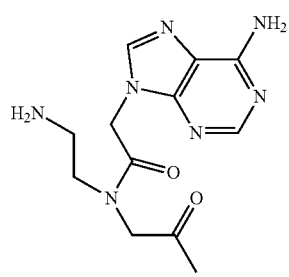
Ac-KLKKLKLVI
(SEQ ID NO: 40)
12

-continued

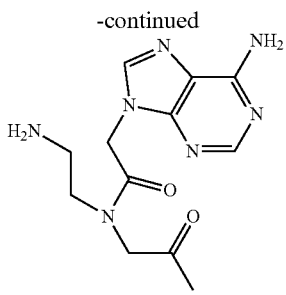

Ac-RFRKAKKGGHEIE
(SEQ ID NO: 41)
13

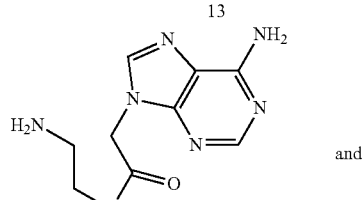

and

Ac-FRRKLI
(SEQ ID NO: 42)
14

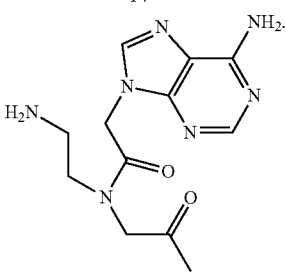

Ac-KFRKAKKGLKEVEK
(SEQ ID NO: 43)
15

46. The pharmaceutical composition according to claim 38, wherein the peptidic compound is:

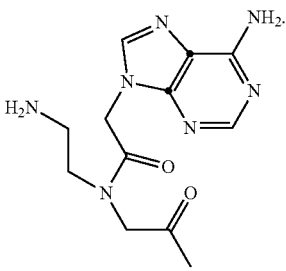

Ac-FRRKFRL
(SEQ ID NO:31)
3

47. A method of inhibiting the proliferation of cancer cells comprising contacting said cancer cells with an effective amount of the peptidic compound according to claim 15.

48. The method according to claim 47, wherein said peptidic compound is of Formula (V):

$$N_xB_y(A/N)_xB_yN_y-J(M)-N_yB_zA_xB_yN_y \qquad (V).$$

49. The method according to claim 48, wherein said ATP mimetic is a compound of Formula (XXXIII):

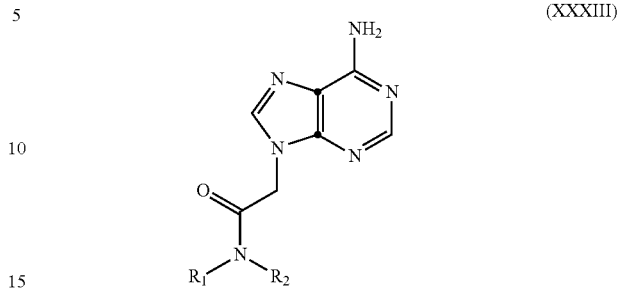

(XXXIII)

wherein:
R$_1$ and R$_2$ are independently alkyl substituted with a carboxyl, carbonyl, alcohol or primary amino.

50. The method according to claim 48, wherein said peptidic compound comprises between about 5 and 16 amino acids.

51. The method according to claim 48, wherein:
each B is independently Arg or Lys; and
each A is independently Phe or His.

52. The method according to claim 48, wherein said peptidic compound further comprises at the C-terminus an additional sequence of up to 4 amino acids in length comprising a sequence selected from the group consisting of Glu-Val-Glu, Asp-Asp, Glu-Gly-Glu, Glu-Ile-Glu, Glu-Val-Glu-Lys (SEQ ID NO:47), and Glu-Val-Asp.

53. The method according to claim 48, wherein said peptidic compound comprises a modified C-terminus and/or N-terminus.

54. The method according to claim 53, wherein said peptidic compound comprises an acetylated N-terminus.

55. The method according to claim 48, wherein said peptidic compound is selected from the group consisting of:

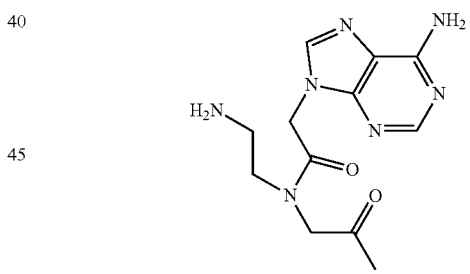

Ac-LRRAKLG
(SEQ ID NO: 30)
2

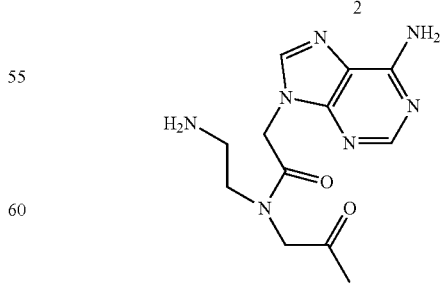

Ac-FRRKFRL
(SEQ ID NO: 31)
3

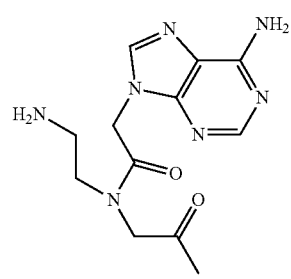
Ac-KFRRKLRLEVD
(SEQ ID NO: 34)
6
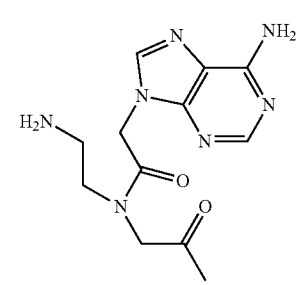
Ac-KLRRAKRLEVD
(SEQ ID NO: 35)
7
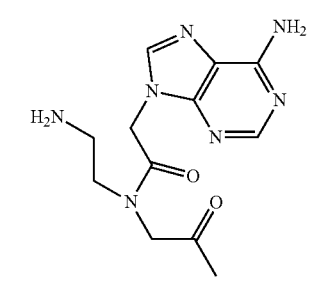
Ac-KLRRAKLGLGDD
(SEQ ID NO: 36)
8
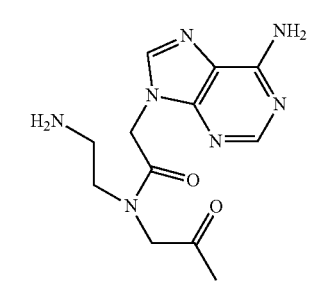
Ac-KLKKAKLGL
(SEQ ID NO: 37)
9
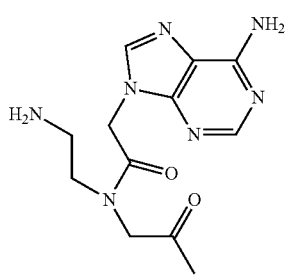
Ac-KAKKKKAKEGE
(SEQ ID NO: 39)
11
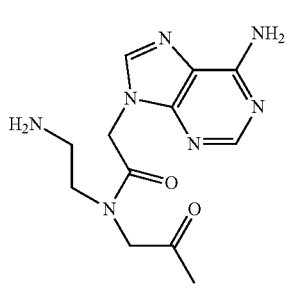
Ac-KLKKLKLVI
(SEQ ID NO: 40)
12
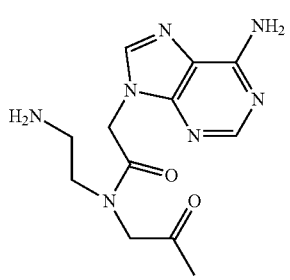
Ac-RFRKAKKGGHEIE
(SEQ ID NO: 41)
13
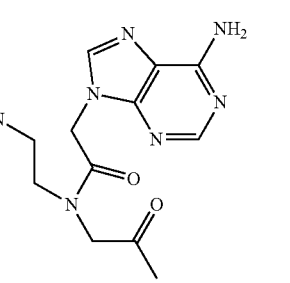
and
Ac-FRRKLI
(SEQ ID NO: 42)
14

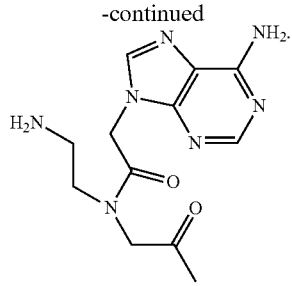
Ac-KFRKAKKGLKEVEK
(SEQ ID NO: 43)
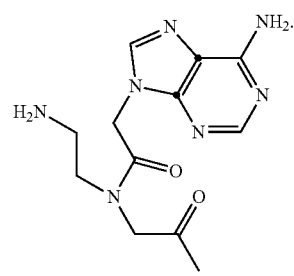
Ac-FRRKFRL
(SEQ ID NO:31)
57. The method according to claim 48, wherein the cancer cells are in vivo.
56. The method according to claim 48, wherein the peptidic compound is:
* * * * *

SEQUENCE LISTING

```
<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Leu Arg Arg Ala Lys Leu Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide

<400> SEQUENCE: 2

Phe Arg Arg Lys Phe Arg Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

His Cys Ile Gly Arg Phe Lys
1               5
```

```
<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Gly Cys Lys Gly Lys Phe Lys Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Lys Phe Arg Arg Lys Arg Gly Arg
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Lys Phe Arg Arg Lys Leu Arg Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic peptide

<400> SEQUENCE: 7

Lys Leu Arg Arg Ala Lys Arg Phe Leu
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Phe Arg Arg Cys Phe Arg Leu
1               5

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Lys Leu Arg Arg Ala Lys Leu Gly Leu Gly
1               5                   10

<210> SEQ ID NO 10
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 10

Lys Leu Lys Lys Ala Lys Leu Gly Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Gly Cys Lys Gly Lys Phe Lys Arg
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Lys Ala Lys Lys Lys Lys Ala Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Lys Leu Lys Lys Leu Lys Leu Val Ile
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Arg Phe Arg Lys Ala Lys Lys Gly Gly His
1               5                   10

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Phe Arg Arg Lys Leu Ile
1               5

<210> SEQ ID NO 16
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 16

Lys Phe Arg Lys Ala Lys Lys Gly Leu Lys
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Synthetic peptide

<400> SEQUENCE: 17

Gly Cys Arg Gly Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Lys Lys Cys Gly Gly Lys Lys Lys
1               5

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Lys Phe Arg Arg Lys Arg Gly Arg Glu Val Asp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Lys Phe Arg Arg Lys Leu Arg Leu Glu Val Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide

<400> SEQUENCE: 21

Lys Leu Arg Arg Ala Lys Arg Phe Leu Glu Val Asp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
```

```
<400> SEQUENCE: 22

Lys Leu Arg Arg Ala Lys Leu Gly Leu Gly Asp Asp
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Lys Ala Lys Lys Lys Lys Ala Lys Glu Gly Glu
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Arg Phe Arg Lys Ala Lys Lys Gly Gly His Glu Ile Glu
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic peptide

<400> SEQUENCE: 25

Lys Phe Arg Lys Ala Lys Lys Gly Leu Lys Glu Val Glu Lys
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Gly Cys Arg Gly Arg Glu Val Asp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Arg Lys Arg Cys Leu Arg Arg Leu
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28
```

```
Arg Arg Arg Cys Leu Arg Arg Leu
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Leu Arg Arg Ala Ser Leu Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (5)..(5)
<223> OTHER INFORMATION: Xaa is lysine bound to adenine PNA via the
      amino group of the lysine side chain

<400> SEQUENCE: 30

Leu Arg Arg Ala Xaa Leu Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (4)..(4)
<223> OTHER INFORMATION: Xaa is lysine bound to adenine PNA via the
      amino group of the lysine side chain

<400> SEQUENCE: 31

Phe Arg Arg Xaa Phe Arg Leu
1               5

<210> SEQ ID NO 32
<211> LENGTH: 7
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation

<400> SEQUENCE: 32

Phe Arg Arg Cys Phe Arg Leu
1               5

<210> SEQ ID NO 33
```

```
<211> LENGTH: 11
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (5)..(5)
<223> OTHER INFORMATION: Xaa is lysine bound to adenine PNA via the
      amino group of the lysine side chain

<400> SEQUENCE: 33

Lys Phe Arg Arg Xaa Arg Gly Arg Glu Val Asp
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (5)..(5)
<223> OTHER INFORMATION: Xaa is lysine bound to adenine PNA via the
      amino group of the lysine side chain

<400> SEQUENCE: 34

Lys Phe Arg Arg Xaa Leu Arg Leu Glu Val Asp
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain

<400> SEQUENCE: 35

Lys Leu Arg Arg Ala Xaa Arg Phe Leu Glu Val Asp
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain
```

```
<400> SEQUENCE: 36

Lys Leu Arg Arg Ala Xaa Leu Gly Leu Gly Asp Asp
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain

<400> SEQUENCE: 37

Lys Leu Lys Lys Ala Xaa Leu Gly Leu
1               5

<210> SEQ ID NO 38
<211> LENGTH: 8
<212> TYPE: PRT
<213> ORGANISM: Artificial Sequence
<220> FEATURE:
<223> OTHER INFORMATION: Modified synthetic peptide
<220> FEATURE:
<221> NAME/KEY: SITE
<222> LOCATION: (1)..(1)
<223> OTHER INFORMATION: Xaa is glycine bound to adenine PNA via the
      N-terminus of the glycine
<220> FEATURE:
<221> NAME/KEY: AMIDATION
<222> LOCATION: (8)..(8)
<223> OTHER INFORMATION: C-terminal amidation

<400> SEQUENCE: 38

Xaa Cys Lys Gly Lys Phe Lys Arg
1               5

<210> SEQ ID NO 39
<211> LENGTH: 11
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (5)..(5)
<223> OTHER INFORMATION: Xaa is lysine bound to adenine PNA via the
      amino group of the lysine side chain

<400> SEQUENCE: 39

Lys Ala Lys Lys Xaa Lys Ala Lys Glu Gly Glu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Modified synthetic peptide
<220> FEATURE:
```

```
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain

<400> SEQUENCE: 40

Lys Leu Lys Lys Leu Xaa Leu Val Ile
1               5

<210> SEQ ID NO 41
<211> LENGTH: 13
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain

<400> SEQUENCE: 41

Arg Phe Arg Lys Ala Xaa Lys Gly Gly His Glu Ile Glu
1               5                   10

<210> SEQ ID NO 42
<211> LENGTH: 6
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (4)..(4)
<223> OTHER INFORMATION: Xaa is lysine bound to adenine PNA via the
      amino group of the lysine side chain

<400> SEQUENCE: 42

Phe Arg Arg Xaa Leu Ile
1               5

<210> SEQ ID NO 43
<211> LENGTH: 14
<212> TYPE: PRT
<213> ORGANISM: Artificial Sequence
<220> FEATURE:
<223> OTHER INFORMATION: Modified synthetic peptide
<220> FEATURE:
<221> NAME/KEY: ACETYLATION
<222> LOCATION: (1)..(1)
<223> OTHER INFORMATION: N-terminal acetylation
<220> FEATURE:
<221> NAME/KEY: SITE
<222> LOCATION: (6)..(6)
<223> OTHER INFORMATION: Xaa is lysine bound to adenine PNA via the
      amino group of the lysine side chain

<400> SEQUENCE: 43

Lys Phe Arg Lys Ala Xaa Lys Gly Leu Lys Glu Val Glu Lys
1               5                   10
```

```
<210> SEQ ID NO 44
<211> LENGTH: 8
<212> TYPE: PRT
<213> ORGANISM: Artificial Sequence
<220> FEATURE:
<223> OTHER INFORMATION: Modified synthetic peptide
<220> FEATURE:
<221> NAME/KEY: SITE
<222> LOCATION: (1)..(1)
<223> OTHER INFORMATION: Xaa is glycine bound to adenine PNA via the
      N-terminus of the glycine

<400> SEQUENCE: 44

Xaa Cys Arg Gly Arg Glu Val Asp
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Ala Thr Pro Lys Leu
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Leu Lys Pro Thr Ala
1               5

<210> SEQ ID NO 47
<211> LENGTH: 4
<212> TYPE: PRT
<213> ORGANISM: Artificial Sequence
<220> FEATURE:
<223> OTHER INFORMATION: Synthetic peptide

<400> SEQUENCE: 47

Glu Val Glu Lys
1
```